US011266686B2

(12) United States Patent
Warner et al.

(10) Patent No.: US 11,266,686 B2
(45) Date of Patent: Mar. 8, 2022

(54) METAL COMPLEXES AND METHODS OF TREATMENT

(71) Applicant: PROCYPRA THERAPEUTICS LLC, Sausalito, CA (US)

(72) Inventors: John C. Warner, Sausalito, CA (US); Srinivasa R. Cheruku, Sausalito, CA (US); Anitha Hari, Sausalito, CA (US); James J. Norman, Sausalito, CA (US)

( * ) Notice: Subject to any disclaimer, the term of this patent is extended or adjusted under 35 U.S.C. 154(b) by 0 days.

(21) Appl. No.: 15/035,911

(22) PCT Filed: Nov. 10, 2014

(86) PCT No.: PCT/US2014/064879
§ 371 (c)(1),
(2) Date: May 11, 2016

(87) PCT Pub. No.: WO2015/070177
PCT Pub. Date: May 14, 2015

(65) Prior Publication Data
US 2016/0271175 A1    Sep. 22, 2016

Related U.S. Application Data

(60) Provisional application No. 61/902,682, filed on Nov. 11, 2013, provisional application No. 61/932,348, filed on Jan. 28, 2014.

(51) Int. Cl.
| | | |
|---|---|---|
| *A61K 33/34* | (2006.01) | |
| *A61K 51/04* | (2006.01) | |
| *C07C 229/36* | (2006.01) | |
| *C07C 337/08* | (2006.01) | |
| *G01N 33/53* | (2006.01) | |
| *A61K 47/54* | (2017.01) | |
| *C07C 59/105* | (2006.01) | |
| *C07C 59/265* | (2006.01) | |
| *C07C 323/58* | (2006.01) | |
| *C07D 275/06* | (2006.01) | |

(52) U.S. Cl.
CPC ............ *A61K 33/34* (2013.01); *A61K 47/547* (2017.08); *A61K 51/0478* (2013.01); *C07C 59/105* (2013.01); *C07C 59/265* (2013.01); *C07C 229/36* (2013.01); *C07C 323/58* (2013.01); *C07C 337/08* (2013.01); *C07D 275/06* (2013.01); *G01N 33/53* (2013.01); *C07B 2200/13* (2013.01); *Y02A 50/30* (2018.01)

(58) Field of Classification Search
CPC ........................... A61K 33/34; A61K 51/0478
See application file for complete search history.

(56) References Cited

U.S. PATENT DOCUMENTS

| | | | | |
|---|---|---|---|---|
| 4,477,387 A | * | 10/1984 | Kidani ................ | C07F 15/0093 556/26 |
| 5,707,604 A | * | 1/1998 | Ranney .................... | B82Y 5/00 424/9.35 |
| 2012/0270850 A1 | * | 10/2012 | Barnham ............. | A61K 31/315 514/184 |

FOREIGN PATENT DOCUMENTS

| | | |
|---|---|---|
| CA | 2881928 A1 | 10/2013 |
| WO | WO2004/078163 A2 | 9/2004 |
| WO | WO2008/061306 A1 | 5/2008 |
| WO | WO2008/061306 A1 | 9/2008 |
| WO | WO2010/066010 A1 | 6/2010 |

OTHER PUBLICATIONS

Graciela M. Escandar, Complexs of Cu(II) with D-alsonic and D-alduronic acids in aqueous solution, Can. J. Chem, 70, 2053 (Year: 1991).*
Inna Miroshnyk et al., Pharmaceutical co-crystals-an opportunity for drug product enhancement, Expert Opin. Drug Deliv, 6(4), 333-341. (Year: 2009).*
Graceila M Escandar, Complexes of Cu(II) with D-aldonic and D-alduronic acids in aqueous solution, Can. J Chem. 70, 2053-2057. (Year: 1992).*
McQuade, P., et al., "Investigation into <64>CU-labeled Bis-(selenosemicarbazone) and Bis(thiosemicarbazone) complexes as hypoxia imaging agents," Nuclear Medicine and Biology, Elsevier, NY, US, vol. 32, No. 2, Feb. 1, 2005, pp. 147-156.
Holland, J. P., et al., "Functionalized Bis(thiosemicarbazonato) Complexes of Zinc and Copper: Synthetic Platforms Toward Site-Specific Radiopharmaceuticals," Inorganic Chemistry, vol. 46, No. 2, Jan. 1, 2007, pp. 465-485.
Blower, P.J., et al., "Structural trends in copper(ii) bis(thiosemicarbazone) radiopharmaceuticals," Dalton Transactions, No. 23, Jan. 1, 2003, p. 4416-4425.
International Search Report for PCT Patent App. No. PCT/US/2014/064879 (dated Aug. 25, 2015).
Written Opinion for PCT Patent App. No. PCT/US/2014/064879 (dated Aug. 25, 2015).
Blower, P. J., et al., "Structural trends in copper(II) bis(thiosemicarbazone) radiopharmaceuticals," Dalton Trans. 2003;23:4416-4425.

(Continued)

*Primary Examiner* — Michael G. Hartley
*Assistant Examiner* — Jagadishwar R Samala
(74) *Attorney, Agent, or Firm* — Cermak Nakajima & McGowan LLP; Malcolm K. McGowan

(57) ABSTRACT

In one embodiment, the present application discloses compounds that are selective neuroactive agents for the treatment of diseases of the central nervous system (CNS). In one aspect, the neuroactive agents are NCDs of metal chelates, including complexes of iron, copper or zinc.

4 Claims, 11 Drawing Sheets

(56) References Cited

OTHER PUBLICATIONS

Palanimuthu, D., et al., "In Vitro and in Vivo Anticancer Activity of Copper Bis(thiosemicarbazone) Complexes," J. Med. Chem. 2013;56:722-734.

Paterson, B. M., et al., "Versatile New Bis(thiosemicarbazone) Bifunctional Chelators: Synthesis, Conjugation to Bombesin(7-14)-NH2, and Copper-64 Radiolabeling," Inorg. Chem. 2010;49:1884-1893.

Holland, J. P., et al., "Functionalized Bis(thiosemicarbazonato) Complexes of Zinc and Copper: Synthetic Platforms Toward Site-Specific Radiopharmaceuticals," Inorg. Chem. 2007;46:465-485.

English translation of Notice of Reasons for Rejection for Japanese Patent App. No. 2016-553260 (dated Aug. 23, 2018).

Office Action from Canadian Patent App. No. 2,930,290 (dated Jan. 14, 2021).

\* cited by examiner

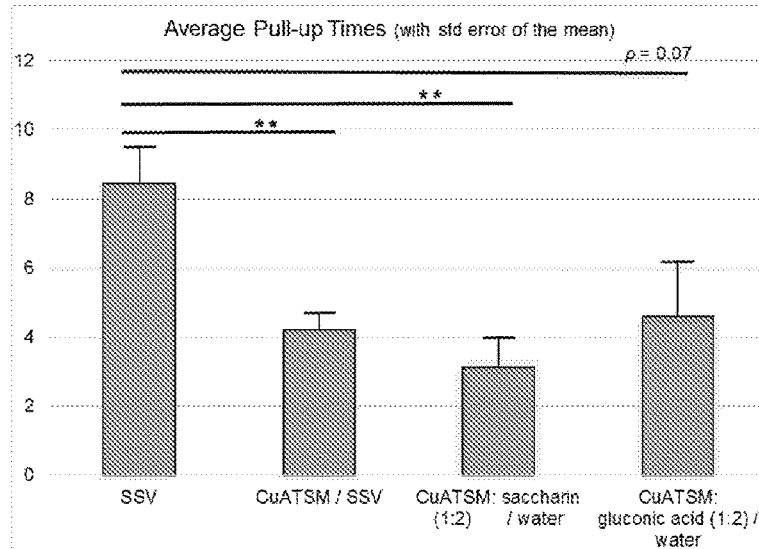
Figure 9. Average wire pull-up times of treated, MPTP-lesioned mice, showing standard error of the mean of the samples in each treatment population; **, $p < 0.01$.
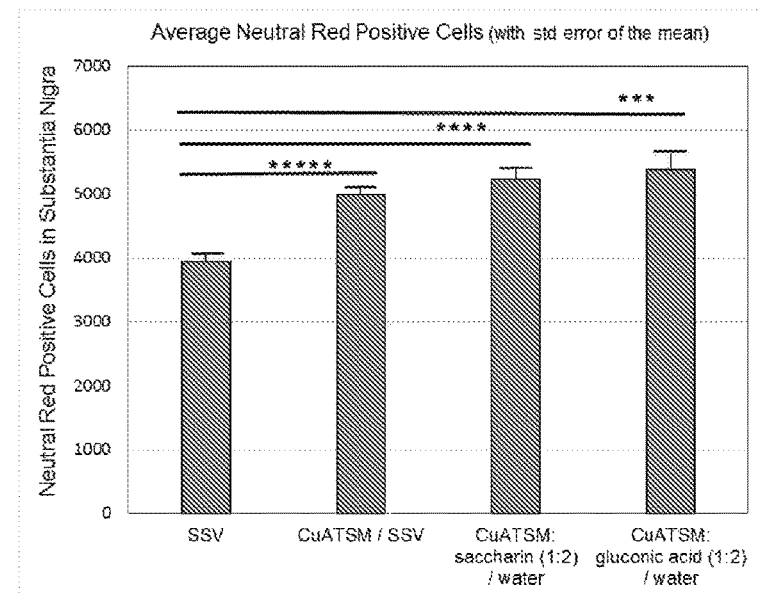
Figure 10. Neutral Red positive cell count in substantia nigra of treated, MPTP-lesioned mice, showing standard error of the mean of the samples in each treatment population; *, $p < 0.001$; , $p < 0.0001$; ***, $p < 0.00001$.

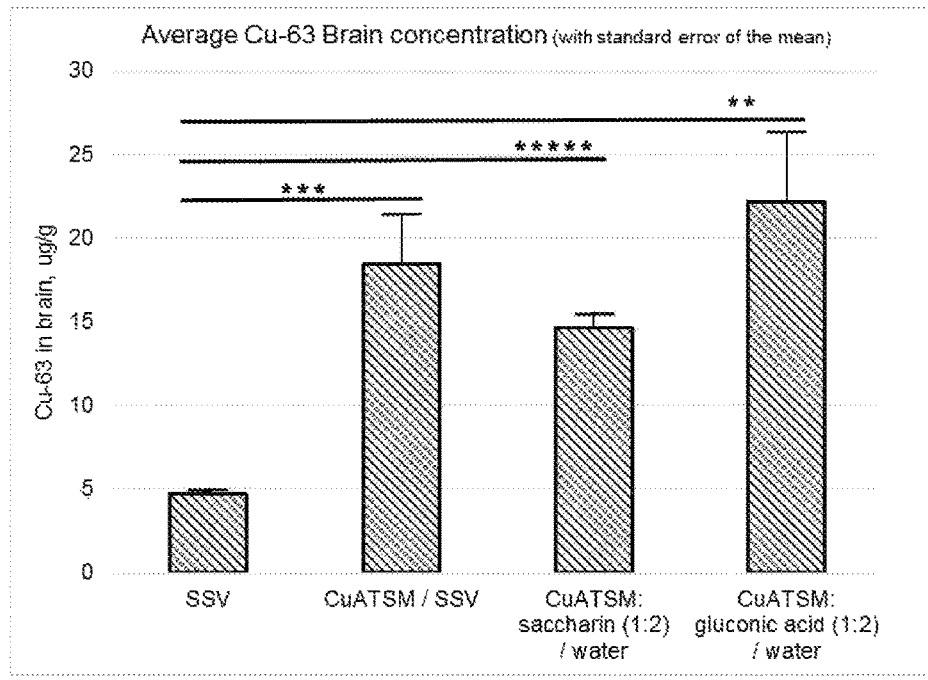
Figure 11. Average Cu-63 Brain concentration in treated, MPTP-lesioned mice; , $p < 0.01$ *, $p < 0.001$; *****, $p < 0.00001$.
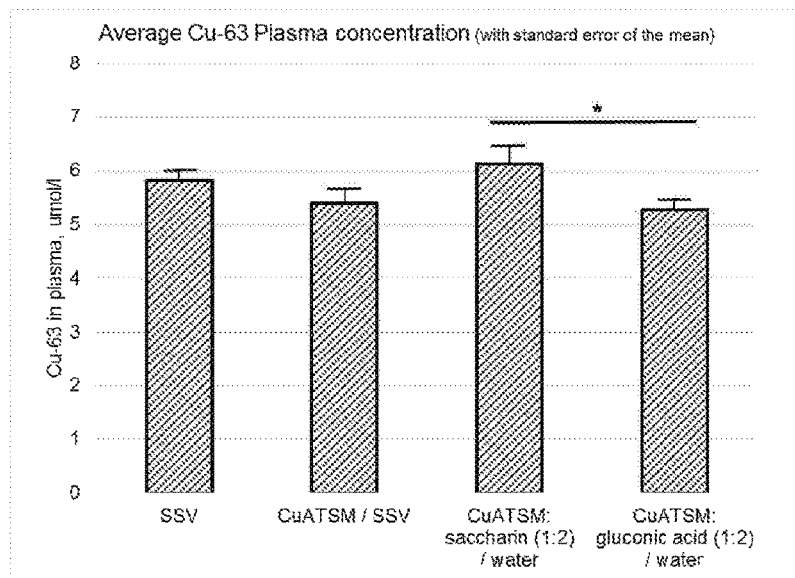
Figure 12. Average Cu-63 Plasma concentration in treated, MPTP-lesioned mice; *, $p < 0.05$.

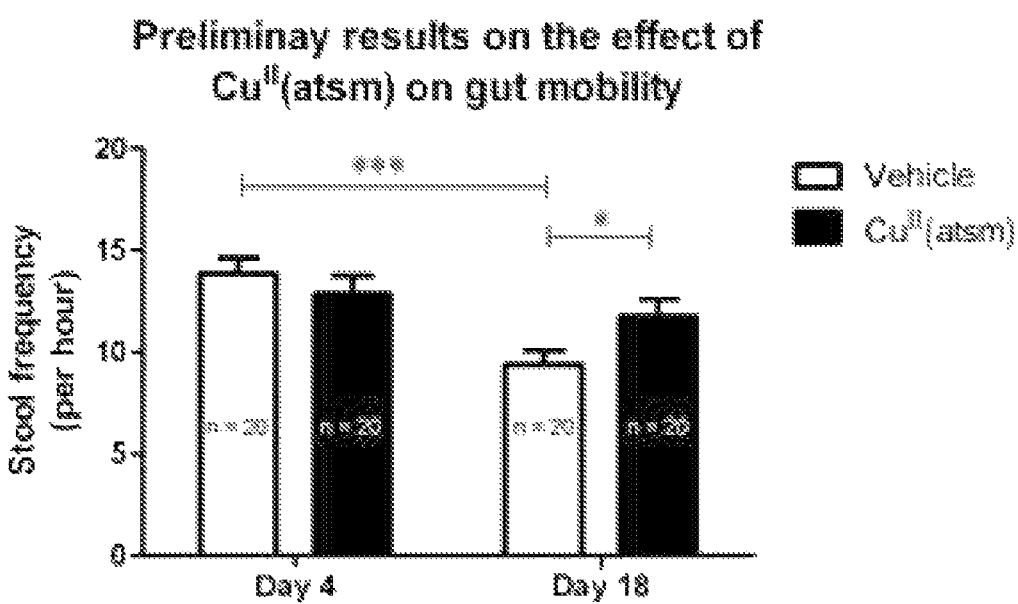
Figure 13: A representative results for a comparison of stool frequency between vehicle and treatment with Cu-ATSM.

METAL COMPLEXES AND METHODS OF TREATMENT

RELATED APPLICATIONS

This application is a national stage entry under 35 USC 371 of PCT Patent Application No. PCT/US2014/064879, filed on Nov. 10, 2014, which claims priority under 35 USC 119 to U.S. Provisional Application No. 61/902,682, filed Nov. 11, 2013 and U.S. Provisional Application No. 61/932,348, filed Jan. 28, 2014. Each of these priority applications are incorporated by reference in their entireties.

BACKGROUND OF THE APPLICATION

The present invention relates to the use of metal complexes as pharmaceutical agents, in particular for the treatment of conditions in which metal delivery can prevent, alleviate or ameliorate the condition. There are a number of clinical conditions which are caused by or associated with abnormal levels of metals (typically low metal levels). Conditions of this type include cancer and conditions characterized by or associated with oxidative damage, more specifically neurodegenerative conditions or diseases such as Alzheimer's disease (AD), Parkinson's disease (PD), Huntington's disease, hypoxia and prion diseases (PrDs).

Bio-available metals have significant impact on the working of biological systems. It is known that metals play a significant role in enzyme systems and in the signaling mechanisms within biological systems. For example, Zn plays an important role in the β-amyloid plaques of Alzheimer's disease; the effect of the (Cu, Zn) superoxide dismutase enzyme in mediating reactive oxygen species damage associated with amyotrophic lateral sclerosis; the participation of the heme enzymes NO synthase and guanylyl cyclase in the production and sensing, respectively, of nitric oxide (NO), and the discovery of a "zinc-finger" motif in the breast and ovarian cancer susceptibility gene, BRCA1 for example. In addition, it has been demonstrated that an aberrant protein has a propensity to misfold in the presence of certain concentrations of metal ions.

A number of cardiovascular conditions have been identified that are the result of oxidative stress (OS). Other conditions associated with OS include cancer, cataracts, neurodegenerative disorders such as Alzheimer's disease and heart diseases. There is also evidence that OS plays a prominent role in three types of neuromuscular disorders: amyotrophic lateral sclerosis (ALS), mitochondrial/metabolic disease and Friedreich's ataxia. Common features of these diseases include the deposition of misfolded protein and substantial cellular damage as a result of OS. Data suggests that OS is the primary cause of physical damage in a wide range of disease states, including amyloidogenic neurological disorders such as Alzheimer's disease (AD), amyotrophic lateral sclerosis (ALS), prion diseases—including Creutzfeldt-Jakob Disease (CJD), transmissible spongioform encephalopathies (TSE), cataracts, mitochondrial disorders, Menkes disease, Parkinson's disease (PD) and Huntington's disease (HD). The effect of OS is not limited to any one part of the human body, with examples of the negative effects of OS being observed for almost all organs. For example, the human brain is an organ that concentrates metal ions and recent evidence suggests that a breakdown in metal homeostasis plays a critical role in a variety of age-related neurodegenerative diseases.

A number of therapeutic agents have been developed as potential therapies for the conditions caused by or associated with OS. However, agents such as vitamin E and vitamin C were found to be ineffective, as they do not cross the blood brain barrier and accordingly, cannot be used effectively for the treatment of neurodegenerative diseases of central origin.

Copper metal ion deficiency has been reported as a condition associated with AD. One consequence of copper deficiency is that the protective enzymes responsible for detoxifying reactive oxygen species (ROS) are inadequately loaded with copper and therefore do not effectively carry out normal enzyme function. The inadequate loading of such protective enzymes, for example in the brain, leads to a general increase in OS (as is observed in AD) which will be reflected in increased protein oxidation, such as increased protein carbonyls.

Accordingly, there is a need for highly effective agents for the treatment of disease associated with oxidative damage and particularly central nervous system neurodegenerative disorders such as PD, AD and CJD. In addition, there is a need for novel agents for the treatment of conditions associated with peripheral tissues, gastrointestinal dysfunction such as constipation, and acute respiratory distress syndrome, ALS, atherosclerotic cardiovascular disease and multiple organ dysfunction.

In addition to motor dysfunction experienced by patients with certain neurological diseases, such as Parkinson's Disease, non-motor symptoms including gastrointestinal ailments, such as constipation, are commonly experienced by patients with neurological diseases. These symptoms have a significant and adverse impact on the quality of the patient's life. In one aspect of the present application, there is provided a method for treating or reducing gastrointestinal diseases or ailments associated with patients with neurological diseases, the method includes the administration of a therapeutically effective amount of the NCD of the metal complex as disclosed herein.

Patients with certain neurodegenerative diseases, such as PD for example, also suffer from non-motor aspects of the disease in which disturbances within the autonomic nervous system are noted, and controls of these automatic bodily functions, such as heart rate, blood pressure, sweating and both gastrointestinal and urinary function are adversely affected. Gastrointestinal dysfunction associated with neurodegenerative diseases such as PD, may include constipation.

The foregoing examples of the related art and limitations are intended to be illustrative and not exclusive. Other limitations of the related art will become apparent to those of skill in the art upon a reading of the specification and a study of the drawings or figures as provided herein.

SUMMARY OF THE APPLICATION

There is a continuing need for novel and effective agents that are selective neuroactive agents for the treatment of diseases of the central nervous system (CNS). In one aspect, the neuroactive agents are ion chelators, including copper and zinc, etc. The following embodiments, aspects and variations thereof are exemplary and illustrative are not intended to be limiting in scope.

In a first embodiment, the present invention is based on the discovery that non-covalent derivatives (NCDs) of certain metal complexes are effective in delivering bio-available metal and may be used in the treatment of conditions which can be prevented, treated or ameliorated by metal delivery. In particular these NCD of metal complexes are found to be effective in delivering metal to the cells in a form which lead to a significant anti-oxidant effect being observed in the cell. In one aspect, certain NCD of metal complexes demonstrated an ability to mediate OS. In another embodiment, the NCD of metal complexes and their derivatives may also be used for in vivo diagnostic tools involving copper(II) and other divalent metals.

In a second embodiment, the present application discloses a non-covalent derivative (NCD) of a compound of Formula I with a Ligand:

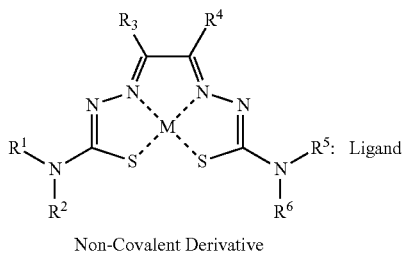

Non-Covalent Derivative wherein:

M is Fe, Zn or Cu;

$R^1$ and $R^2$ are each independently selected from the group consisting of H, substituted or unsubstituted $C_1$-$C_6$ alkyl, substituted or unsubstituted $C_2$-$C_6$ alkenyl, substituted or unsubstituted $C_2$-$C_6$ alkynyl, substituted or unsubstituted $C_5$-$C_{10}$ aryl, substituted or unsubstituted $C_5$-$C_{10}$ heteroaryl, substituted or unsubstituted heteroalkyl, substituted or unsubstituted cycloalkyl, substituted or unsubstituted —$C_1$-$C_6$ alkyl-$C_6$-$C_{10}$ aryl, substituted or unsubstituted heteroaryl, substituted or unsubstituted heterocyclyl, —$C_1$-$C_6$ alkylheterocyclyl, substituted or unsubstituted $C_1$-$C_6$ alkylC(O)—, substituted or unsubstituted $C_1$-$C_6$ alkylS(O)$_{1-2}$—, substituted or unsubstituted $C_1$-$C_6$ alkylNR'C(O)— and substituted or unsubstituted $C_1$-$C_6$ alkoxyC(NR")—, hydroxy, hydroxyalkyl, alkoxy, —NH($R^7$), —N($R^7$)$_2$, —COOH, —COR$^7$, —COOR$^7$, —CONHR$^7$, —CSNHR$^7$, —S(O)R$^7$, —S(O)$_2$R$^7$, —C(O)N($R^7$)$_2$, —SO$_2$N($R^7$)$_2$ and —(CH$_2$)$_m$R$^8$, each of which may be optionally substituted; or $R^1$ and $R^2$ when taken together with the nitrogen atom to which they are attached form an optionally substituted heterocycloalkyl or heteroaryl group;

$R^3$ and $R^4$ are each independently H, substituted or unsubstituted $C_1$-$C_6$ alkyl, substituted or unsubstituted $C_2$-$C_6$ alkenyl, substituted or unsubstituted $C_1$-$C_6$ alkynyl, substituted or unsubstituted $C_1$-$C_6$ heteroalkyl, substituted or unsubstituted $C_3$-$C_{10}$ cycloalkyl, substituted or unsubstituted $C_3$-$C_{10}$ heterocycloalkyl, substituted or unsubstituted $C_5$-$C_{10}$ aryl, substituted or unsubstituted $C_5$-$C_{10}$ heteroaryl, substituted or unsubstituted —$C_1$-$C_6$ alkyl-$C_{6-10}$ aryl, substituted or unsubstituted $C_1$-$C_6$ alkylC(O)—, substituted or unsubstituted $C_1$-$C_6$ alkylS(O)$_{1-2}$—, substituted or unsubstituted $C_1$-$C_6$ alkylNR'C(O)— and substituted or unsubstituted $C_1$-$C_6$ alkoxyC(NR")—, or $R^3$ and $R^4$ together with the carbon atoms that they are attached to form a 5 or 6-membered carbocyclic ring;

$R^5$ and $R^6$ are each independently selected from the group consisting of H, substituted or unsubstituted $C_1$-$C_6$ alkyl, substituted or unsubstituted $C_2$-$C_6$ alkenyl, substituted or unsubstituted $C_2$-$C_6$ alkynyl, substituted or unsubstituted $C_5$-$C_{10}$ aryl, substituted or unsubstituted $C_5$-$C_{10}$ heteroaryl, substituted or unsubstituted heteroalkyl, substituted or unsubstituted cycloalkyl, substituted or unsubstituted —$C_1$-$C_6$ alkyl-$C_6$-$C_{10}$ aryl, substituted or unsubstituted heteroaryl, substituted or unsubstituted heterocyclyl, —$C_1$-$C_6$ alkylheterocyclyl, substituted or unsubstituted $C_1$-$C_6$ alkylC(O)—, substituted or unsubstituted $C_1$-$C_6$ alkylS(O)$_{1-2}$—, substituted or unsubstituted $C_1$-$C_6$ alkylNR'C(O)— and substituted or unsubstituted $C_1$-$C_6$ alkoxyC(NR")—, hydroxy, hydroxyalkyl, alkoxy, —NH($R^7$), —N($R^7$)$_2$, —COOH, —COR$^7$, —COOR$^7$, —CONHR$^7$, —CSNHR$^7$, —S(O)R$^7$, —S(O)$_2$R$^7$, —C(O)N($R^7$)$_2$, —SO$_2$N($R^7$)$_2$ and —(CH$_2$)$_m$R$^8$, each of which may be optionally substituted; or $R^5$ and $R^6$ when taken together with the nitrogen atom to which they are attached form an optionally substituted heterocycloalkyl or heteroaryl group;

each $R^7$ is independently selected from the group consisting of H, alkyl, alkenyl, alkynyl, haloalkyl, heteroalkyl, cycloalkyl, heterocycloalkyl, aryl, heteroaryl, cycloalkylalkyl, heterocycloalkylalkyl, arylalkyl, heteroarylalkyl and acyl, each of which may be optionally substituted;

each $R^8$ is independently selected from the group consisting of cycloalkyl, heterocycloalkyl, aryl and heteroaryl, each of which may be optionally substituted; R' and R" are each independently selected from the group consisting of H and $C_1$-$C_6$ alkyl; and m is an integer selected from the group consisting of 1, 2, 3, 4, 5 and 6;

Ligand is a ligand, co-additive, co-former, coordinating moiety, or an organic compound that complexes with the compound of Formula I to form the non-covalent derivative; and a pharmaceutically acceptable salt thereof. In one aspect, the NCD is prepared from the compound of the Formula I and a ligand as disclosed herein. In one aspect of the above compound, M is Zn or Cu.

As disclosed in the present application, the NCDs are represented or depicted, for example, as a 1:1 stoichiometry simply to represent the NCDs irrespective of the stoichiometry. That is, the NCDs may be formed or prepared irrespective of the stoichiometry. For example, the NCDs may be formed from the compound of the Formula I with 1, 2 or 3 ligands, depending on the nature of the metal, the chelating agent and the relative stoichiometry of the added reagents to form the NCD. Similarly, the NCDs may comprise 1, 2 or 3 metal chelates with one or more ligands as disclosed herein.

NCDs of the present application, such as those prepared from the compound of the Formula I above, may be prepared as generally depicted below:

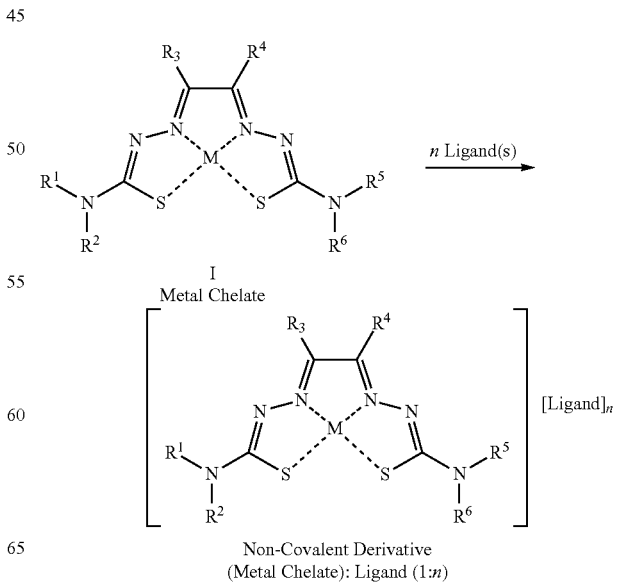

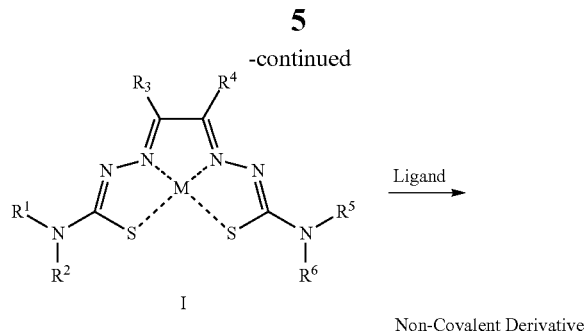

I

Ligand →

Non-Covalent Derivative

In one aspect of the above NCD; $R^3$ and $R^4$ are each independently H, substituted or unsubstituted $C_1$-$C_6$ alkyl, substituted or unsubstituted $C_5$-$C_{10}$ aryl, substituted or unsubstituted —$C_1$-$C_6$ alkyl-$C_{6-10}$ aryl, substituted or unsubstituted $C_1$-$C_6$ alkylC(O)—, substituted or unsubstituted $C_1$-$C_6$ alkylS(O)$_{1-2}$—, substituted or unsubstituted $C_1$-$C_6$ alkylNR'C(O)— and substituted or unsubstituted $C_1$-$C_6$ alkoxyC(NR")—, or $R^1$ and $R^2$ together with the carbon atoms that they are attached to form a 5 or 6-membered carbocyclic ring;

$R^1$ is H and $R^2$ is selected from the group consisting of substituted or unsubstituted $C_1$-$C_6$ alkyl, substituted or unsubstituted $C_5$-$C_{10}$ aryl, substituted or unsubstituted —$C_1$-$C_6$ alkyl-$C_6$-$C_{10}$ aryl, substituted or unsubstituted heterocyclyl, —$C_1$-$C_6$ alkyl-heterocyclyl, substituted or unsubstituted $C_1$-$C_6$ alkylC(O)—, substituted or unsubstituted $C_1$-$C_6$ alkylS(O)$_{1-2}$—, substituted or unsubstituted $C_1$-$C_6$ alkylNR'C(O)— and substituted or unsubstituted $C_1$-$C_6$ alkoxyC(NR")—; and $R^5$ is H and $R^6$ is selected from the group consisting of substituted or unsubstituted $C_1$-$C_6$ alkyl, substituted or unsubstituted $C_5$-$C_{10}$ aryl, substituted or unsubstituted —$C_1$-$C_6$ alkyl-$C_6$-$C_{10}$ aryl, substituted or unsubstituted heterocyclyl, —$C_1$-$C_6$ alkyl-heterocyclyl, substituted or unsubstituted $C_1$-$C_6$ alkylC(O)—, substituted or unsubstituted $C_1$-$C_6$ alkylS(O)$_{1-2}$—, substituted or unsubstituted $C_1$-$C_6$ alkylNR'C(O)— and substituted or unsubstituted $C_1$-$C_6$ alkoxyC(NR")—.

In another aspect of the NCD, $R^3$ and $R^4$ are each independently H, $C_{1-3}$ alkyl or $R^3$ and $R^4$ together with the carbon atoms to which they are attached form a $C_6$ cyclohexyl group; and each $R^5$ and $R^6$ is independently selected from the group consisting of $C_{1-3}$ alkyl, —$C_6H_5$, p-Cl—$C_6H_4$, p-MeO—$C_6H_4$, —$C_{1-2}$ alkyl-$C_6H_5$, —$C_{1-2}$ alkyl-p-Cl—$C_6H_4$, —$C_{1-2}$ alkyl-p-MeO—$C_6H_4$ and —$C_{1-2}$ alkyl-morpholino. In one variation of the above, $R^3$ and $R^4$ are each independently selected from H, methyl or ethyl. In another variation, each $R^5$ and $R^6$ is independently methyl, ethyl, —$C_6H_5$, —$CH_2$—$C_6H_5$, p-MeO—$C_6H_4$— and —$CH_2CH_2$—N-morpholino. In one variation of the above compound, $R^1$ and $R^5$ are hydrogen and $R^2$ and $R^6$ are the same. In another variation of the above, the compound is symmetrically substituted. In one variation, the compound is symmetrically substituted to form a C2 axis of rotational symmetry.

In another aspect of the NCD, the Ligand is selected from the group consisting of: a) an amino acid, such as those selected from the group consisting of alanine, arginine, asparagine, aspartic acid, cysteine, glutamic acid, glutamine, glycine, histidine, isoleucine, leucine, lysine, methionine, ornithine, phenylalanine, proline, serine, threonine, tryptophan, tyrosine and valine; b) an ester of an amino acid, such as those selected from the group consisting of alanine ethyl ester, arginine ethyl ester, arginine methyl ester, cysteine ethyl ester, cysteine di-methyl ester, glycine ethyl ester, phenylalanine ethyl ester, tyrosine ethyl ester, L-tyrosine methyl ester, tyrosine methyl ester and tryptophan ethyl ester; c) a dipeptide, such as Ala-Gly, Gly-Ala, L-alanyl-L-glutamine, Ala-Tyr, Tyr-Ala, Ala-Gln, Gln-Ala, Gly-Tyr, Tyr-Gly, Ile-Tyr, Tyr-Ile, Ile-Trp, Lys-Trp, Lys-Glu, Glu-Tyr, Ile-Leu and Leu-Ile; d) an organic carboxylic acid, dicarboxylic acid or polycarboxylic acid, such as those selected from the group consisting of citric acid, thiodipropionic acid, gluconic acid, glucuronic acid, ascorbic acid, citric acid, succinic acid, lactic acid, malic acid, adipic acid, trans-aconitic acid, benzoic acid, caprylic acid, uric acid, cholic acid, tartaric acid, linoleic acid, nicotinic acid, oleic acid, pectinic acid, propionic acid, salicylic acid, sorbic acid, stearic acid; e) a monosaccharide or a disaccharide, such as those selected from the group consisting of glucose, lactose, maltose, sucrose, fructose, mannitol, sorbitol, ribose and sorbose; and f) an organic compound, such as those selected from the group consisting of 2-pyrrolidinone, caffeine, saccharin, N,N,N',N'-tetrabutylterephthalamide, N,N,N',N'-tetraethylterephthalamide, N,N,N',N'-tetrapropylterephthalamide, urea, propylene glycol, niacinamide (nicotinamide), pyridoxine, riboflavin, thiamin (thiamine) and alpha-tocopherol acetate (Vitamin E acetate). In one aspect of the above, the ligand is selected from the group consisting of citric acid, thiodipropionic acid, gluconic acid, glucuronic acid, ascorbic acid, caffeine, glucose, glutathione, lactose, lactic acid, malic acid, maltose, succinic acid, uric acid, citric acid, L-tyrosine methyl ester, cystine di-methyl ester and saccharin. In one variation, the Ligand is selected from the group consisting of an amino acid, citric acid, thiodipropionic acid, gluconic acid, glucuronic acid, ascorbic acid, caffeine, glucose, glutathione, lactose, lactic acid, malic acid, maltose, succinic acid, uric acid, citric acid, L-tyrosine methyl ester, cystine di-methyl ester and saccharin. In one variation of the NCD, the Ligand is selected from the group consisting of gluconic acid, citric acid, L-tyrosine methyl ester, cystine di-methyl ester and saccharin. In one variation of the NCD, the ligand is gluconic acid.

In yet another aspect of the above, $R^3$ and $R^4$ are each independently H, $C_{1-3}$ alkyl or together with the carbon atoms to which they are attached form a $C_6$ cyclohexyl group; and each $R^5$ and $R^6$ is independently selected from the group consisting of $C_{1-3}$ alkyl, —$C_6H_5$, p-Cl—$C_6H_4$, p-MeO—$C_6H_4$, —$C_{1-2}$ alkyl-$C_6H_5$, —$C_{1-2}$ alkyl-p-Cl—$C_6H_4$, —$C_{1-2}$ alkyl-p-MeO—$C_6H_4$ and —$C_{1-2}$ alkyl-morpholino.

In another aspect of the above NCD, the compound of the Formula I is selected from the group consisting of I.1 to I.31:

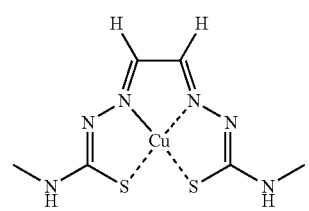

I.1

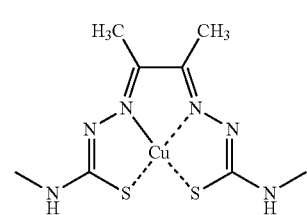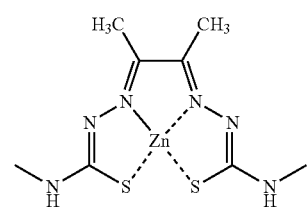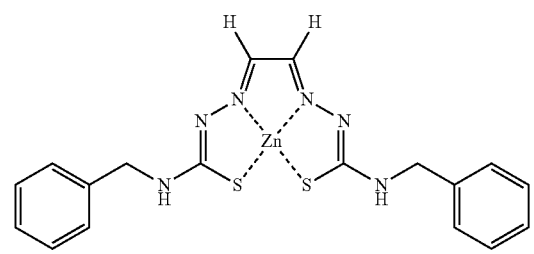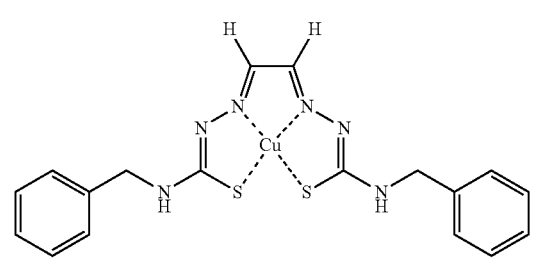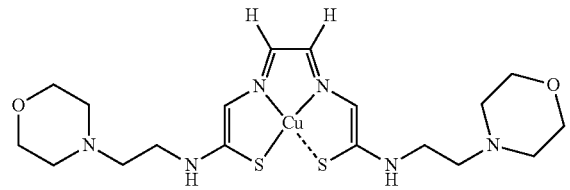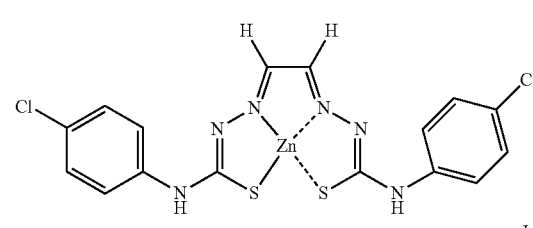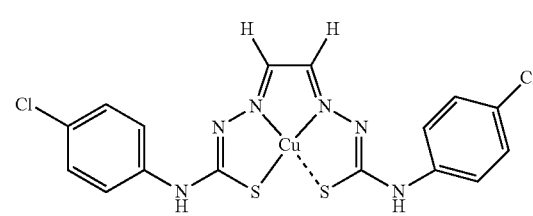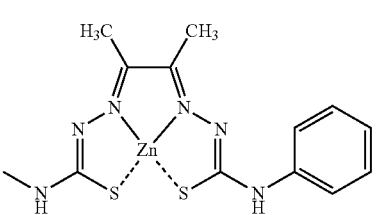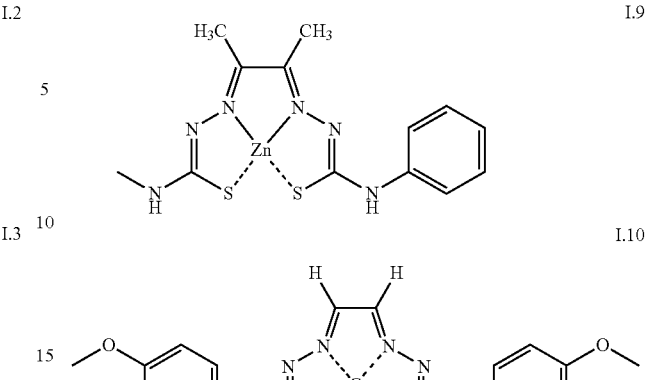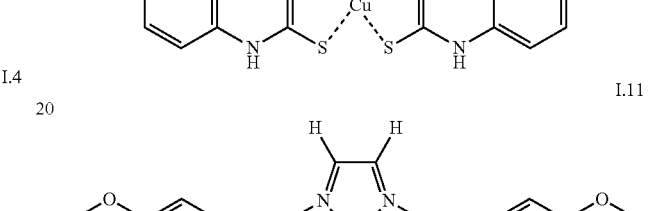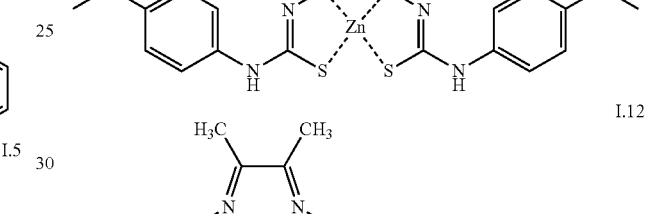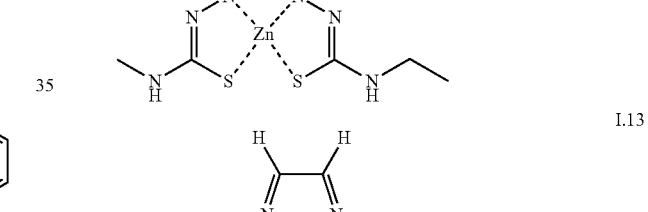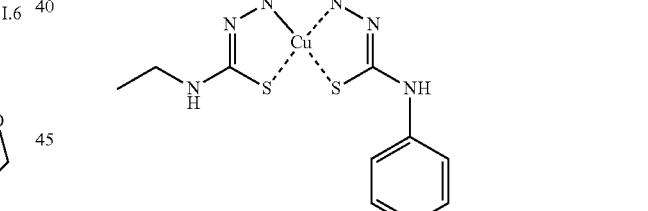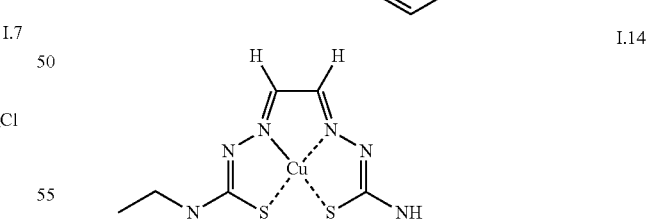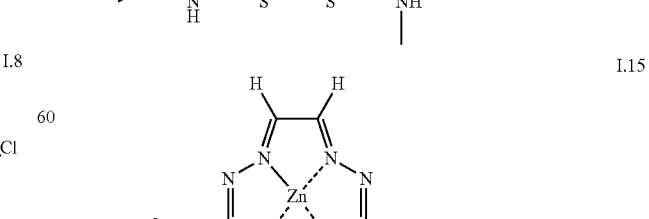

I.16
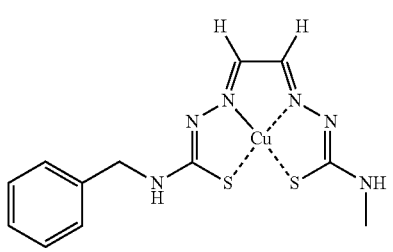
I.17
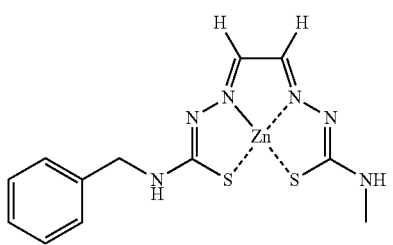
I.18
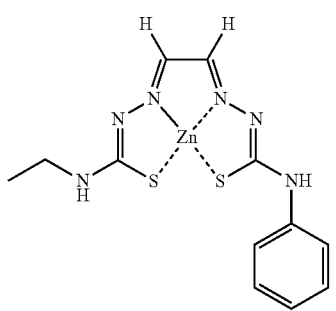
I.19
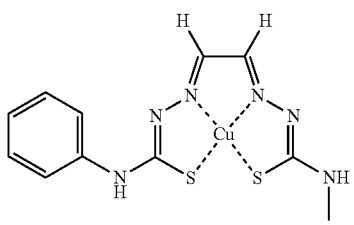
I.20
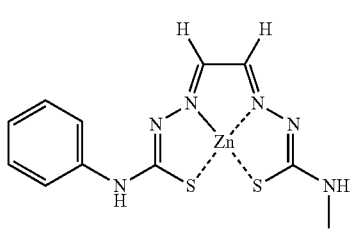
I.21
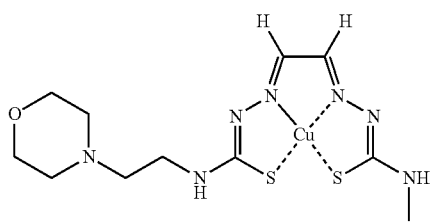
I.22
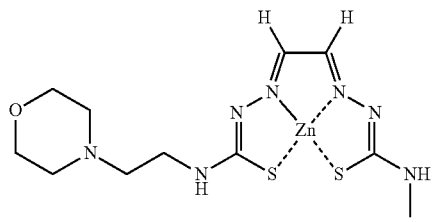
I.23
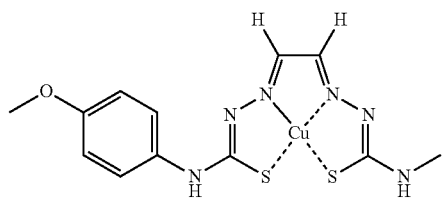
I.24
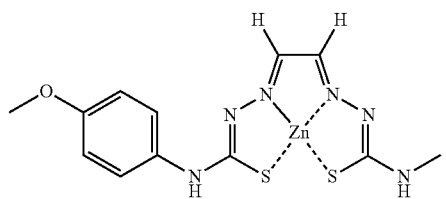
I.25
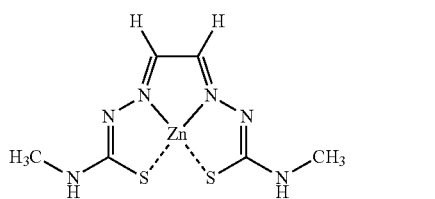
I.26
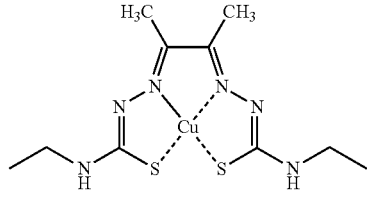
I.27
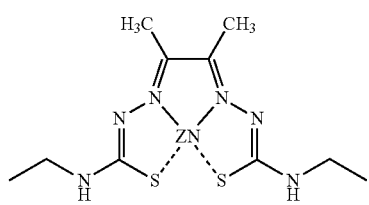
I.28
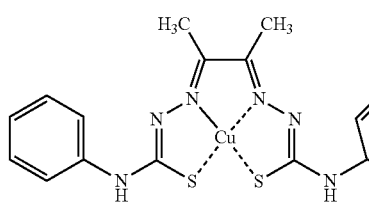
I.29
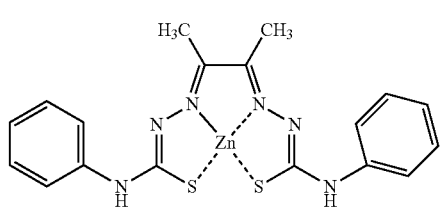

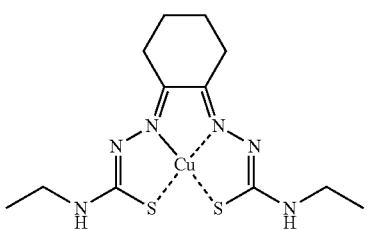

I.30

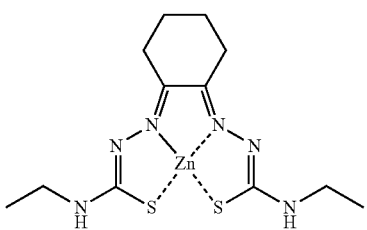

I.31

In a third embodiment, the application discloses a non-covalent derivative (NCD) of a compound of Formula Ia with a Metallated Ligand:

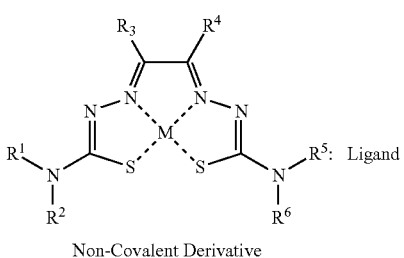

I

Non-Covalent Derivative wherein:
the compound of the Formula Ia is:

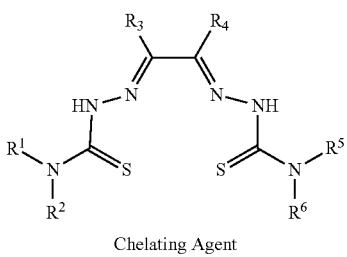

Ia

Chelating Agent

Ligand is a ligand, co-additive, co-former, coordinating moiety, or an organic compound;

Metallated Ligand is a metal salt of the Ligand wherein the metal is selected from the group consisting of Fe, Zn and Cu;

$R^1$ and $R^2$ are each independently selected from the group consisting of H, substituted or unsubstituted $C_1$-$C_6$ alkyl, substituted or unsubstituted $C_2$-$C_6$ alkenyl, substituted or unsubstituted $C_2$-$C_6$ alkynyl, substituted or unsubstituted $C_5$-$C_{10}$ aryl, substituted or unsubstituted $C_5$-$C_{10}$ heteroaryl, substituted or unsubstituted heteroalkyl, substituted or unsubstituted cycloalkyl, substituted or unsubstituted —$C_1$-$C_6$ alkyl-$C_6$-$C_{10}$ aryl, substituted or unsubstituted heteroaryl, substituted or unsubstituted heterocyclyl, —$C_1$-$C_6$ alkyl-heterocyclyl, substituted or unsubstituted $C_1$-$C_6$ alkylC(O)—, substituted or unsubstituted $C_1$-$C_6$ alkylS(O)$_{1-2}$—, substituted or unsubstituted $C_1$-$C_6$ alkylNR'C(O)— and substituted or unsubstituted $C_1$-$C_6$ alkoxyC(NR")—, hydroxy, hydroxyalkyl, alkoxy, —NH($R^7$), —N($R^7$)$_2$, —COOH, —COR$^7$, —COOR$^7$, —CONHR$^7$, —CSNHR$^7$, —S(O)R$^7$, —S(O)$_2$R$^7$, —C(O)N(R$^7$)$_2$, —SO$_2$N(R$^7$)$_2$ and —(CH$_2$)$_m$R$^8$, each of which may be optionally substituted; or $R^1$ and $R^2$ when taken together with the nitrogen atom to which they are attached form an optionally substituted heterocycloalkyl or heteroaryl group;

$R^3$ and $R^4$ are each independently H, substituted or unsubstituted $C_1$-$C_6$ alkyl, substituted or unsubstituted $C_2$-$C_6$ alkenyl, substituted or unsubstituted $C_1$-$C_6$ alkynyl, substituted or unsubstituted $C_1$-$C_6$ heteroalkyl, substituted or unsubstituted $C_3$-$C_{10}$ cycloalkyl, substituted or unsubstituted $C_3$-$C_{10}$ heterocycloalkyl, substituted or unsubstituted $C_5$-$C_{10}$ aryl, substituted or unsubstituted $C_5$-$C_{10}$ heteroaryl, substituted or unsubstituted —$C_1$-$C_6$ alkyl-$C_{6-10}$ aryl, substituted or unsubstituted $C_1$-$C_6$ alkylC(O)—, substituted or unsubstituted $C_1$-$C_6$ alkylS(O)$_{1-2}$—, substituted or unsubstituted $C_1$-$C_6$ alkylNR'C(O)— and substituted or unsubstituted $C_1$-$C_6$ alkoxyC(NR")—, or $R^3$ and $R^4$ together with the carbon atoms that they are attached to form a 5 or 6-membered carbocyclic ring;

$R^5$ and $R^6$ are each independently selected from the group consisting of H, substituted or unsubstituted $C_1$-$C_6$ alkyl, substituted or unsubstituted $C_2$-$C_6$ alkenyl, substituted or unsubstituted $C_2$-$C_6$ alkynyl, substituted or unsubstituted $C_5$-$C_{10}$ aryl, substituted or unsubstituted $C_5$-$C_{10}$ heteroaryl, substituted or unsubstituted heteroalkyl, substituted or unsubstituted cycloalkyl, substituted or unsubstituted —$C_1$-$C_6$ alkyl-$C_6$-$C_{10}$ aryl, substituted or unsubstituted heteroaryl, substituted or unsubstituted heterocyclyl, —$C_1$-$C_6$ alkyl-heterocyclyl, substituted or unsubstituted $C_1$-$C_6$ alkylC(O)—, substituted or unsubstituted $C_1$-$C_6$ alkylS(O)$_{1-2}$—, substituted or unsubstituted $C_1$-$C_6$ alkylNR'C(O)— and substituted or unsubstituted $C_1$-$C_6$ alkoxyC(NR")—, hydroxy, hydroxyalkyl, alkoxy, —NH($R^7$), —N($R^7$)$_2$, —COOH, —COR$^7$, —COOR$^7$, —CONHR$^7$, —CSNHR$^7$, —S(O)R$^7$, —S(O)$_2$R$^7$, —C(O)N(R$^7$)$_2$, —SO$_2$N(R$^7$)$_2$ and —(CH$_2$)$_m$R$^8$, each of which may be optionally substituted; or $R^5$ and $R^6$ when taken together with the nitrogen atom to which they are attached form an optionally substituted heterocycloalkyl or heteroaryl group;

each $R^7$ is independently selected from the group consisting of H, alkyl, alkenyl, alkynyl, haloalkyl, heteroalkyl, cycloalkyl, heterocycloalkyl, aryl, heteroaryl, cycloalkylalkyl, heterocycloalkylalkyl, arylalkyl, heteroarylalkyl and acyl, each of which may be optionally substituted;

each $R^8$ is independently selected from the group consisting of cycloalkyl, heterocycloalkyl, aryl and heteroaryl, each of which may be optionally substituted;

R' and R" are each independently selected from the group consisting of H and $C_1$-$C_6$ alkyl; and m is an integer selected from the group consisting of 1, 2, 3, 4, 5 and 6; and a pharmaceutically acceptable salt thereof.

In a fourth embodiment, the application discloses a method of preparing the above non-covalent derivative (NCD) by reacting a chelating agent Ia with a Metallated Ligand:

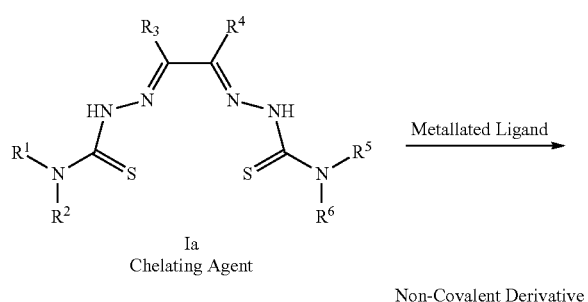

Ia
Chelating Agent

→ Metallated Ligand

Non-Covalent Derivative

In one aspect, the Metallated Ligand is metal gluconate wherein the metal is selected from the group consisting of Fe, Cu or Zn. In one aspect of the above NCD, $R^3$ and $R^4$ are each independently H, substituted or unsubstituted $C_1$-$C_6$ alkyl, substituted or unsubstituted $C_5$-$C_{10}$ aryl, substituted or unsubstituted —$C_1$-$C_6$ alkyl-$C_{6-10}$ aryl, substituted or unsubstituted $C_1$-$C_6$ alkylC(O)—, substituted or unsubstituted $C_1$-$C_6$ alkylS(O)$_{1-2}$—, substituted or unsubstituted $C_1$-$C_6$ alkylNR'C(O)— and substituted or unsubstituted $C_1$-$C_6$ alkoxyC(NR")—, or $R^1$ and $R^2$ together with the carbon atoms that they are attached to form a 5 or 6-membered carbocyclic ring; $R^1$ is H and $R^2$ is selected from the group consisting of substituted or unsubstituted $C_1$-$C_6$ alkyl, substituted or unsubstituted $C_5$-$C_{10}$ aryl, substituted or unsubstituted —$C_1$-$C_6$ alkyl-$C_6$-$C_{10}$ aryl, substituted or unsubstituted heterocyclyl, —$C_1$-$C_6$ alkyl-heterocyclyl, substituted or unsubstituted $C_1$-$C_6$ alkylC(O)—, substituted or unsubstituted $C_1$-$C_6$ alkylS(O)$_{1-2}$—, substituted or unsubstituted $C_1$-$C_6$ alkylNR'C(O)— and substituted or unsubstituted $C_1$-$C_6$ alkoxyC(NR")—; and $R^5$ is H and $R^6$ is selected from the group consisting of substituted or unsubstituted $C_1$-$C_6$ alkyl, substituted or unsubstituted $C_5$-$C_{10}$ aryl, substituted or unsubstituted —$C_1$-$C_6$ alkyl-$C_6$-$C_{10}$ aryl, substituted or unsubstituted heterocyclyl, —$C_1$-$C_6$ alkyl-heterocyclyl, substituted or unsubstituted $C_1$-$C_6$ alkylC(O)—, substituted or unsubstituted $C_1$-$C_6$ alkylS(O)$_{1-2}$—, substituted or unsubstituted $C_1$-$C_6$ alkylNR'C(O)— and substituted or unsubstituted $C_1$-$C_6$ alkoxyC(NR")—.

In another aspect of the NCD, $R^1$ is H; $R^2$ is substituted or unsubstituted $C_1$-$C_6$ alkyl; $R^3$ and $R^4$ are methyl; $R^5$ is substituted or unsubstituted $C_1$-$C_6$ alkyl; and $R^6$ is substituted or unsubstituted $C_1$-$C_6$ alkyl. In one aspect of the NCD, the compound of the Formula Ia is ATSMH$_2$ and the metallated ligand is copper gluconate. In one variation of the above, the NCD is a gluconic acid NCD in the solid state prepared by the reaction between a compound of the Formula Ia and a metal gluconate, wherein the metal is selected from Fe, Cu and Zn. In one variation, the metal is copper or zinc. In another aspect of the above NCD, the compound of the Formula Ia is ATSMH$_2$ and the metal gluconate is copper(II) gluconate or zinc(II) gluconate.

In another aspect of each of the above, the application discloses the above NCD, or a pharmaceutically acceptable salt thereof, optionally in the form of a single stereoisomer or mixture of stereoisomers thereof. In yet another aspect, there is provided a pharmaceutical composition comprising a therapeutically effective amount of an NCD of each of the above, and a pharmaceutically acceptable excipient or salt.

In a fifth embodiment, the application discloses a method for the treatment or prophylaxis of a condition in a mammal in which metal delivery can prevent, alleviate or ameliorate the condition comprising administering to the mammal a therapeutically effective amount of an NCD or a pharmaceutical composition thereof of any one of the above embodiments, aspect and variations. In one variation of the above method, the condition is selected from the group consisting of tau related disorders, disorders caused by or associated with oxidative stress and Abeta related disorders. In another variation of the above method, the condition is caused by or associated with oxidative stress in the subject. In another variation, the condition is a tau related disorder or an Abeta related disorder. In another variation of the method, the condition is selected from the group consisting of cardiovascular disease, central nervous system disorders, cancers and neurological disease or disorders. In another variation of the method, the neurological disease is a neurodegenerative disease.

Oral administration of a metal complex, such as CuII-ATSM (or Cu-ATSM, or CuATSM) or an NCD of the metal complex, has been shown to be neuroprotective and restore motor performance and cognitive function to MPTP (1-methyl-4-phenyl-1,2,3,6-tetrahydropyridine) lesioned mice. In addition, the treatment of Cu-ATSM or the NCD of Cu-ATSM also improved stool frequency and is found to be correlated with the restoration of neuronal subpopulations in the myenteric plexus of MPTP lesioned mice. Accordingly, patients with neurological diseases, such as Parkinson's Disease, experiencing gastrointestinal disfunction such as constipation, may be associated with the loss of neuronal populations in conjunction with enteric glial cell reactivity within the myenteric plexus of the gastrointestinal tract. Treatment of these patients with agents such as the metal complexes, such as Cu-ATSM, or the NCD of the metal complexes, such as NCD of Cu-ATSM, that are neuroprotective in the central nervous system provides symptom release and also results in disease modifying in the gastrointestinal tract.

As disclosed herein, several rodent models of Parkinson's Disease have shown gastrointestinal dysfunction, which has been correlated with the loss of neuronal subpopulations within the enteric nervous system. It has been determined that the administration of MPTP (1-methyl-4-phenyl-1,2,3,6-tetrahydropyridine) caused a significant reduction in the number of dopaminergic neurons within the substantia nigra pars compacta of C57BL/6 mice. In addition, a reduction in neuronal subpopulations within the myenteric plexus of the ileum 21 days after lesioning was also detected and was concomitant with a reduction in stool frequency, indicative of digestive dysfunction.

In another aspect of the above method, the condition is a gastrointestinal disease or disorder associated with the condition selected from the group consisting of adriamycin-induced cardiomyopathy; AIDS dementia and HIV-1 induced neurotoxicity; Alzheimer's disease; acute intermittent porphyria; Alzheimer's disease (AD); amyotrophic lateral sclerosis (ALS); atherosclerosis; cataract; cerebral ischaemia; cerebral palsy; cerebral tumor; chemotherapy-induced organ damage; cisplatin-induced nephrotoxicity; coronary artery bypass surgery; Creutzfeldt-Jacob disease and its new variant associated with "mad cow" disease; diabetic neuropathy; Down syndrome; drowning; epilepsy and post-traumatic epilepsy; Friedrich's ataxia; frontotemporal dementia; glaucoma; glomerulopathy; haemochromatosis; haemodialysis; haemolysis; haemolytic uraemic syndrome (Weil's disease); Menkes disease; haemorrhagic stroke; Hallerboden-Spatz disease; heart attack and reperfusion injury; Huntington's disease; Lewy body disease; intermittent claudication; ischaemic stroke; inflammatory bowel disease; macular degeneration; malaria; methanol-induced toxicity; meningitis (aseptic and tuberculous); motor neuron disease; multiple sclerosis; multiple system atrophy; myocardial ischaemia; neoplasia; Parkinson's disease; peri-natal asphyxia; Pick's disease; progressive supranuclear palsy (PSP); radiotherapy-induced organ damage; restenosis after angioplasty; retinopathy; senile dementia; schizophrenia; sepsis; septic shock; spongiform encephalopathies; subharrachnoid haemorrage/cerebral vasospasm; subdural haematoma; surgical trauma, including neurosurgery; thalassemia; transient ischaemic attack (TIA); transplantation; vascular dementia; viral meningitis; viral encephalitis; Neuropathies, acrodermatitis enteropathica; dementia with lewy bodies; tauopathies; mild cognitive impairment (MCI); motor neuron disease (MND) and prion disease.

In one variation of the above method, the condition is a gastrointestinal disease or disorder associated with the condition selected from the group consisting of cardiovascular disease, central nervous system disorders and neurological disorders. In another variation, the condition is a gastrointestinal disease or disorder associated with a neurological disorder. In another variation, the neurological disorder is a gastrointestinal disease or disorder associated with the condition selected from the group consisting of Parkinson's disease, Alzheimer's disease, Multiple sclerosis, Neuropathies, Huntington's disease, Prion disease, motor neuron disease, Amyotrophic lateral sclerosis (ALS) and Menkes disease. In another variation, the disorder is a gastrointestinal disease or disorder associated with Alzheimer's disease. In another variation, the disorder is a gastrointestinal disease or disorder associated with the condition Parkinson's disease. In another variation, the disorder is a gastrointestinal disease or disorder associated with Amyotrophic lateral sclerosis (ALS). In one aspect of the above method, the condition is selected from the group consisting of a neurological disease or a neurodegenerative disease is selected from the group consisting of Alzheimer's disease (AD), amyotrophic lateral sclerosis (ALS), Menkes disease, multiple sclerosis, Neuropathies, motor neuron disease, Parkinson's disease, Huntington Disease, frontotemporal dementia, acrodermatitis enteropathica, dementia with lewy bodies, tauopathies, mild cognitive impairment (MCI), progressive supranuclear palsy (PSP), motor neuron disease (MND) and prion disease.

In one variation of each of the above method, $R^2$ is selected from the group consisting of H, alkyl, aryl, and $-(CH_2)_mR^8$, each of which may be optionally substituted. In another variation, m is 1 or 2. In another variation, $R^8$ is aryl or heterocycloalkyl. In another variation, $R^8$ is phenyl, or morpholin-4-yl. In another variation, $R^2$ is selected from the group consisting of H, methyl, ethyl, phenyl-methyl, 2-morpholin-4-yl-ethyl, phenyl, 4-chloro-phenyl and 4-methoxy-phenyl. In another variation, $R^5$ is selected from the group consisting of H, alkyl and aryl, each of which may be optionally substituted. In another variation, $R^5$ is H. In yet another variation, $R^6$ is selected from the group consisting of H, alkyl, aryl, and $-(CH_2)_mR^8$, each of which may be optionally substituted. In another variation, m is 1 or 2. In another variation, $R^8$ is phenyl, or morpholin-4-yl. In another variation, $R^6$ is selected from the group consisting of H, methyl, ethyl, phenyl-methyl, 2-morpholin-4-yl-ethyl, phenyl, 4-chloro-phenyl and 4-methoxy-phenyl.

In a sixth embodiment, there is provided a method for the treatment or prophylaxis of a condition in a subject in which metal delivery can prevent, alleviate or ameliorate the condition, wherein the condition is selected from the group consisting of tau related disorders, disorders caused by or associated with oxidative stress and Abeta related disorders, the method comprising administration of a therapeutically effective amount of a complex comprising a non-covalent derivative (NCD) of a metal chelate, in which the NCD is formed by reaction of a compound of Formula Ia, the chelating agent, with a Metallated Ligand:

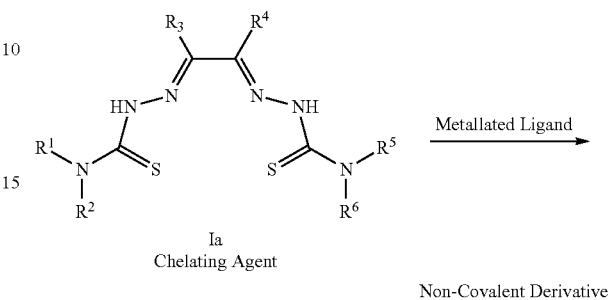

Ia
Chelating Agent

Metallated Ligand →

Non-Covalent Derivative wherein:

Metallated Ligand is a metal salt of a Ligand wherein the metal is selected from the group consisting of Fe, Zn and Cu;

Ligand is a ligand, co-additive, co-former, coordinating moiety, or an organic compound;

$R^1$ and $R^2$ are each independently selected from the group consisting of H, substituted or unsubstituted $C_1$-$C_6$ alkyl, substituted or unsubstituted $C_2$-$C_6$ alkenyl, substituted or unsubstituted $C_2$-$C_6$ alkynyl, substituted or unsubstituted $C_5$-$C_{10}$ aryl, substituted or unsubstituted $C_5$-$C_{10}$ heteroaryl, substituted or unsubstituted heteroalkyl, substituted or unsubstituted cycloalkyl, substituted or unsubstituted $-C_1$-$C_6$ alkyl-$C_6$-$C_{10}$ aryl, substituted or unsubstituted heteroaryl, substituted or unsubstituted heterocyclyl, $-C_1$-$C_6$ alkyl-heterocyclyl, substituted or unsubstituted $C_1$-$C_6$ alkylC(O)—, substituted or unsubstituted $C_1$-$C_6$ alkylS(O)$_{1-2}$—, substituted or unsubstituted $C_1$-$C_6$ alkylNR'C(O)— and substituted or unsubstituted $C_1$-$C_6$ alkoxyC(NR")—, hydroxy, hydroxyalkyl, alkoxy, —NH($R^7$), —N($R^7$)$_2$, —COOH, —COR$^7$, —COOR$^7$, —CONHR$^7$, —CSNHR$^7$, —S(O)R$^7$, —S(O)$_2$R$^7$, —C(O)N($R^7$)$_2$, —SO$_2$N($R^7$)$_2$ and —(CH$_2$)$_m$R$^8$, each of which may be optionally substituted; or $R^1$ and $R^2$ when taken together with the nitrogen atom to which they are attached form an optionally substituted heterocycloalkyl or heteroaryl group;

$R^3$ and $R^4$ are each independently H, substituted or unsubstituted $C_1$-$C_6$ alkyl, substituted or unsubstituted $C_2$-$C_6$ alkenyl, substituted or unsubstituted $C_1$-$C_6$ alkynyl, substituted or unsubstituted $C_1$-$C_6$ heteroalkyl, substituted or unsubstituted $C_3$-$C_{10}$ cycloalkyl, substituted or unsubstituted $C_3$-$C_{10}$ heterocycloalkyl, substituted or unsubstituted $C_5$-$C_{10}$ aryl, substituted or unsubstituted $C_5$-$C_{10}$ heteroaryl, substituted or unsubstituted $-C_1$-$C_6$ alkyl-$C_{6-10}$ aryl, substituted or unsubstituted $C_1$-$C_6$ alkylC(O)—, substituted or unsubstituted $C_1$-$C_6$ alkylS(O)$_{1-2}$—, substituted or unsubstituted $C_1$-$C_6$ alkylNR'C(O)— and substituted or unsubstituted $C_1$-$C_6$ alkoxyC(NR")—, or $R^3$ and $R^4$ together with the carbon atoms that they are attached to form a 5 or 6-membered carbocyclic ring;

$R^5$ and $R^6$ are each independently selected from the group consisting of H, substituted or unsubstituted $C_1$-$C_6$ alkyl, substituted or unsubstituted $C_2$-$C_6$ alkenyl, substituted or unsubstituted $C_2$-$C_6$ alkynyl, substituted or unsubstituted $C_5$-$C_{10}$ aryl, substituted or unsubstituted $C_5$-$C_{10}$ heteroaryl, substituted or unsubstituted heteroalkyl, substituted or unsubstituted cycloalkyl, substituted or unsubstituted —$C_1$-

$C_6$ alkyl-$C_6$-$C_{10}$ aryl, substituted or unsubstituted heteroaryl, substituted or unsubstituted heterocyclyl, —$C_1$-$C_6$ alkyl-heterocyclyl, substituted or unsubstituted $C_1$-$C_6$ alkylC(O)—, substituted or unsubstituted $C_1$-$C_6$ alkylS(O)$_{1-2}$—, substituted or unsubstituted $C_1$-$C_6$ alkylNR'C(O)— and substituted or unsubstituted $C_1$-$C_6$ alkoxyC(NR")—, hydroxy, hydroxyalkyl, alkoxy, —NH($R^7$), —N($R^7$)$_2$, —COOH, —COR$^7$, —COOR$^7$, —CONHR$^7$, —CSNHR$^7$, —S(O)R$^7$, —S(O)$_2$R$^7$, —C(O)N($R^7$)$_2$, —SO$_2$N($R^7$)$_2$ and —(CH$_2$)$_m$R$^8$, each of which may be optionally substituted; or $R^5$ and $R^6$ when taken together with the nitrogen atom to which they are attached form an optionally substituted heterocycloalkyl or heteroaryl group;

each $R^7$ is independently selected from the group consisting of H, alkyl, alkenyl, alkynyl, haloalkyl, heteroalkyl, cycloalkyl, heterocycloalkyl, aryl, heteroaryl, cycloalkylalkyl, heterocycloalkylalkyl, arylalkyl, heteroarylalkyl and acyl, each of which may be optionally substituted;

each $R^8$ is independently selected from the group consisting of cycloalkyl, heterocycloalkyl, aryl and heteroaryl, each of which may be optionally substituted;

R' and R" are each independently selected from the group consisting of H and $C_1$-$C_6$ alkyl;

m is an integer selected from the group consisting of 1, 2, 3, 4, 5 and 6; and a pharmaceutically acceptable salt thereof. Also provided is an NCD represented as follows:

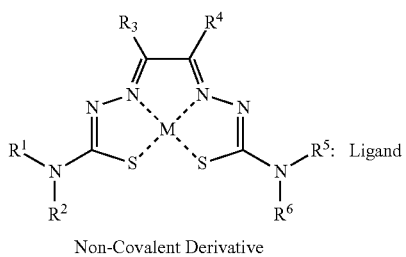

Non-Covalent Derivative

In one aspect of the above, the condition is a gastrointestinal disease or disorder associated with the condition.

In one variation of the above, the compound is of Formula Ia wherein: $R^3$ and $R^4$ are each independently H, substituted or unsubstituted $C_1$-$C_6$ alkyl, substituted or unsubstituted $C_5$-$C_{10}$ aryl, substituted or unsubstituted —$C_1$-$C_6$ alkyl-$C_{6-10}$ aryl, substituted or unsubstituted $C_1$-$C_6$ alkylC(O)—, substituted or unsubstituted $C_1$-$C_6$ alkylS(O)$_{1-2}$—, substituted or unsubstituted $C_1$-$C_6$ alkylNR'C(O)— and substituted or unsubstituted $C_1$-$C_6$ alkoxyC(NR")—, or $R^1$ and $R^2$ together with the carbon atoms that they are attached to form a 5 or 6-membered carbocyclic ring; $R^1$ is H and $R^2$ is selected from the group consisting of substituted or unsubstituted $C_1$-$C_6$ alkyl, substituted or unsubstituted $C_5$-$C_{10}$ aryl, substituted or unsubstituted —$C_1$-$C_6$ alkyl-$C_6$-$C_{10}$ aryl, substituted or unsubstituted heterocyclyl, —$C_1$-$C_6$ alkyl-heterocyclyl, substituted or unsubstituted $C_1$-$C_6$ alkylC(O)—, substituted or unsubstituted $C_1$-$C_6$ alkylS(O)$_{1-2}$—, substituted or unsubstituted $C_1$-$C_6$ alkylNR'C(O)— and substituted or unsubstituted $C_1$-$C_6$ alkoxyC(NR")—; and $R^5$ is H and $R^6$ is selected from the group consisting of substituted or unsubstituted $C_1$-$C_6$ alkyl, substituted or unsubstituted $C_5$-$C_{10}$ aryl, substituted or unsubstituted —$C_1$-$C_6$ alkyl-$C_6$-$C_{10}$ aryl, substituted or unsubstituted heterocyclyl, —$C_1$-$C_6$ alkyl-heterocyclyl, substituted or unsubstituted $C_1$-$C_6$ alkylC(O)—, substituted or unsubstituted $C_1$-$C_6$ alkylS(O)$_{1-2}$—, substituted or unsubstituted $C_1$-$C_6$ alkylNR'C(O)— and substituted or unsubstituted $C_1$-$C_6$ alkoxyC(NR")—. In another aspect of the method, the compound is of Formula Ia wherein: $R^1$ is H; $R^2$ is substituted or unsubstituted $C_1$-$C_6$ alkyl; $R^3$ and $R^4$ are methyl; $R^5$ is substituted or unsubstituted $C_1$-$C_6$ alkyl; and $R^6$ is substituted or unsubstituted $C_1$-$C_6$ alkyl.

In another aspect, the Ligand is selected from the group consisting of an amino acid, citric acid, thiodipropionic acid, gluconic acid, glucuronic glucuronic acid, ascorbic acid, caffeine, glucose, glutathione, lactose, lactic acid, malic acid, maltose, succinic acid, uric acid, citric acid, L-tyrosine methyl ester, cystine di-methyl ester and saccharin. In one aspect of the above, the compound of Formula Ia is ATSMH$_2$ and the Metallated Ligand is copper gluconate. In one variation of the above, the NCD is a gluconic acid NCD in the solid state prepared by the reaction between a compound of the Formula Ia and a metal gluconate, wherein the metal is selected from Fe, Cu and Zn. In another variation, the metal is copper. In one variation, the NCD is prepared from the compound of the Formula Ia and a ligand as disclosed herein. In one variation of the above compound, the metal is Zn or Cu.

In another aspect of the above method, the neurodegenerative disease is selected from the group consisting of Alzheimer's disease (AD), amyotrophic lateral sclerosis (ALS), Menkes disease, multiple sclerosis, Neuropathies, motor neuron disease, Parkinson's disease, Huntington Disease and prion disease. In one variation, the application discloses a method for the treatment of traumatic brain injury, chronic traumatic encephalopathy, traumatic spinal injury, frontotemporal dementia, senile dementia, mild cognitive impairment, and neuronal ceroid lipofuscinoses in a patient in need thereof, comprising administering to the patient a therapeutically effective amount of the above NCD or a pharmaceutical composition. In another variation, there is provided a method of treating or lessening the severity of motor dysfunction and non-motor symptoms associated with a neurodegenerative disease in a patient, comprising administering to the patient a therapeutically effective amount of the above compound or composition.

In a seventh embodiment, there is provided an in vivo method for diagnosing the character of a coordination of copper (II) complex or other divalent metals, comprising:

a) administering a non-covalent derivative (NCD) of a compound of Formula I with a Ligand to a patient; and b) detecting the nature of the complex in the patient, wherein the NCD is:

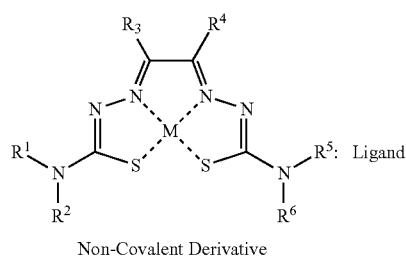

Non-Covalent Derivative wherein:

M is a copper isotope selected from the group consisting of Cu-60, Cu-61 Cu-62 and Cu-64;

$R^1$ and $R^2$ are each independently selected from the group consisting of H, substituted or unsubstituted $C_1$-$C_6$ alkyl, substituted or unsubstituted $C_2$-$C_6$ alkenyl, substituted or unsubstituted $C_2$-$C_6$ alkynyl, substituted or unsubstituted $C_5$-$C_{10}$ aryl, substituted or unsubstituted $C_5$-$C_{10}$ heteroaryl, substituted or unsubstituted heteroalkyl, substituted or unsubstituted cycloalkyl, substituted or unsubstituted —$C_1$-$C_6$ alkyl-$C_6$-$C_{10}$ aryl, substituted or unsubstituted heteroaryl, substituted or unsubstituted heterocyclyl, —$C_1$-$C_6$ alkyl-heterocyclyl, substituted or unsubstituted $C_1$-$C_6$ alkylC(O)—, substituted or unsubstituted $C_1$-$C_6$ alkylS(O)$_{1-2}$—, substituted or unsubstituted $C_1$-$C_6$ alkylNR'C(O)— and substituted or unsubstituted $C_1$-$C_6$ alkoxyC(NR")—, hydroxy, hydroxyalkyl, alkoxy, —NH($R^7$), —N($R^7$)$_2$, —COOH, —COR$^7$, —COOR$^7$, —CONHR$^7$, —CSNHR$^7$, —S(O)R$^7$, —S(O)$_2$R$^7$, —C(O)N($R^7$)$_2$, —SO$_2$N($R^7$)$_2$ and —(CH$_2$)$_m$R$^8$, each of which may be optionally substituted; or $R^1$ and $R^2$ when taken together with the nitrogen atom to which they are attached form an optionally substituted heterocycloalkyl or heteroaryl group;

$R^3$ and $R^4$ are each independently H, substituted or unsubstituted $C_1$-$C_6$ alkyl, substituted or unsubstituted $C_2$-$C_6$ alkenyl, substituted or unsubstituted $C_1$-$C_6$ alkynyl, substituted or unsubstituted $C_1$-$C_6$ heteroalkyl, substituted or unsubstituted $C_3$-$C_{10}$ cycloalkyl, substituted or unsubstituted $C_3$-$C_{10}$ heterocycloalkyl, substituted or unsubstituted $C_5$-$C_{10}$ aryl, substituted or unsubstituted $C_5$-$C_{10}$ heteroaryl, substituted or unsubstituted —$C_1$-$C_6$ alkyl-$C_{6-10}$ aryl, substituted or unsubstituted $C_1$-$C_6$ alkylC(O)—, substituted or unsubstituted $C_1$-$C_6$ alkylS(O)$_{1-2}$—, substituted or unsubstituted $C_1$-$C_6$ alkylNR'C(O)— and substituted or unsubstituted $C_1$-$C_6$ alkoxyC(NR")—, or $R^3$ and $R^4$ together with the carbon atoms that they are attached to form a 5 or 6-membered carbocyclic ring;

$R^5$ and $R^6$ are each independently selected from the group consisting of H, substituted or unsubstituted $C_1$-$C_6$ alkyl, substituted or unsubstituted $C_2$-$C_6$ alkenyl, substituted or unsubstituted $C_2$-$C_6$ alkynyl, substituted or unsubstituted $C_5$-$C_{10}$ aryl, substituted or unsubstituted $C_5$-$C_{10}$ heteroaryl, substituted or unsubstituted heteroalkyl, substituted or unsubstituted cycloalkyl, substituted or unsubstituted —$C_1$-$C_6$ alkyl-$C_6$-$C_{10}$ aryl, substituted or unsubstituted heteroaryl, substituted or unsubstituted heterocyclyl, —$C_1$-$C_6$ alkyl-heterocyclyl, substituted or unsubstituted $C_1$-$C_6$ alkylC(O)—, substituted or unsubstituted $C_1$-$C_6$ alkylS(O)$_{1-2}$—, substituted or unsubstituted $C_1$-$C_6$ alkylNR'C(O)— and substituted or unsubstituted $C_1$-$C_6$ alkoxyC(NR")—, hydroxy, hydroxyalkyl, alkoxy, —NH($R^7$), —N($R^7$)$_2$, —COOH, —COR$^7$, —COOR$^7$, —CONHR$^7$, —CSNHR$^7$, —S(O)R$^7$, —S(O)$_2$R$^7$, —C(O)N($R^7$)$_2$, —SO$_2$N($R^7$)$_2$ and —(CH$_2$)$_m$R$^8$, each of which may be optionally substituted; or $R^5$ and $R^6$ when taken together with the nitrogen atom to which they are attached form an optionally substituted heterocycloalkyl or heteroaryl group;

each $R^7$ is independently selected from the group consisting of H, alkyl, alkenyl, alkynyl, haloalkyl, heteroalkyl, cycloalkyl, heterocycloalkyl, aryl, heteroaryl, cycloalkylalkyl, heterocycloalkylalkyl, arylalkyl, heteroarylalkyl and acyl, each of which may be optionally substituted;

each $R^8$ is independently selected from the group consisting of cycloalkyl, heterocycloalkyl, aryl and heteroaryl, each of which may be optionally substituted;

R' and R" are each independently selected from the group consisting of H and $C_1$-$C_6$ alkyl; and m is an integer selected from the group consisting of 1, 2, 3, 4, 5 and 6;

Ligand is a ligand, co-additive, co-former, coordinating moiety, or an organic compound that complexes with the compound of Formula I to form the non-covalent derivative; and a pharmaceutically acceptable salt thereof.

In a further variation, the application discloses the use of a non-covalent derivative (NCD) of a compound of Formula I or Ib with a ligand in the preparation of a medicament for the treatment or prophylaxis of a condition in which metal delivery can prevent, alleviate or ameliorate the condition. Examples of conditions of this type include conditions selected from the same condition that is a gatrointestinal disease or disorder as recited above. In one variation, there is provided a method for treating, reducing or alleviating a gastrointestinal disease or dysfunction comprising the administration of an NCD comprising a compound of the Formula Ib and a ligand:

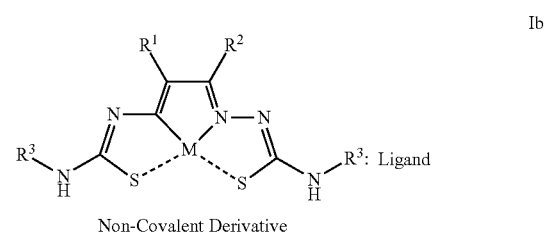

Non-Covalent Derivative wherein: M is Zn or Cu;

Ligand is a ligand, co-additive, co-former, coordinating moiety, or a compound;

$R^1$ and $R^2$ are each independently H, substituted or unsubstituted $C_1$-$C_6$ alkyl, substituted or unsubstituted $C_5$-$C_{10}$ aryl, substituted or unsubstituted —$C_1$-$C_6$ alkyl-$C_{6-10}$ aryl, substituted or unsubstituted $C_1$-$C_6$ alkylC(O)—, substituted or unsubstituted $C_1$-$C_6$ alkylS(O)$_{1-2}$—, substituted or unsubstituted $C_1$-$C_6$ alkylNR'C(O)— and substituted or unsubstituted $C_1$-$C_6$ alkoxyC(NR")—, or $R^1$ and $R^2$ together with the carbon atoms that they are attached to form a 5 or 6-membered carbocyclic ring;

each $R^3$ is independently selected from the group consisting of H, substituted or unsubstituted $C_1$-$C_6$ alkyl, substituted or unsubstituted $C_5$-$C_{10}$ aryl, substituted or unsubstituted —$C_1$-$C_6$ alkyl-$C_6$-$C_{10}$ aryl, substituted or unsubstituted heterocyclyl, —$C_1$-$C_6$ alkyl-heterocyclyl, substituted or unsubstituted $C_1$-$C_6$ alkylC(O)—, substituted or unsubstituted $C_1$-$C_6$ alkylS(O)$_{1-2}$—, substituted or unsubstituted $C_1$-$C_6$ alkylNR'C(O)— and substituted or unsubstituted $C_1$-$C_6$ alkoxyC(NR")—; and Ligand is a ligand, co-additive, co-former, coordinating moiety, or a compound that complexes with the compound of Formula Ib to form the NCD. In one variation of the above, the gastrointestinal disease or dysfunction is associated with or related to a neurological disease. In another variation of the above, the gastrointestinal disease or dysfunction is associated with PD. The above cited NCD may be prepared from the compound of the formula Ib and a Ligand.

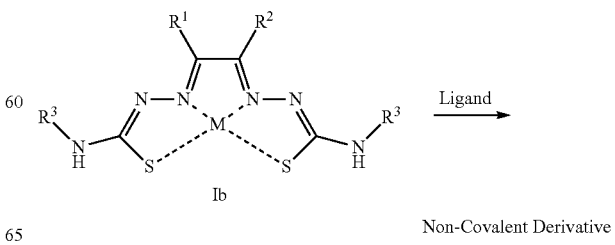

Non-Covalent Derivative

In one variation, the Ligand is selected from the group consisting of amino acids, ascorbic acid, caffeine, citric acid, glucose, gluconic acid, glucuronic acid, glutathione, lactose, lactic acid, malic acid, maltose, saccharin, succinic acid and uric acid. In another variation, the ligand is selected from the group consisting of gluconic acid, citric acid, L-tyrosine methyl ester, cystine di-methyl ester and saccharin.

In another variation of the above, $R^1$ and $R^2$ are each independently H, $C_{1-3}$ alkyl or together with the carbon atoms to which they are attached form a $C_6$ cyclohexyl group; and each $R^3$ is independently $C_{1-3}$ alkyl, —$C_6H_5$, p-Cl—$C_6H_4$, p-MeO—$C_6H_4$, —$C_{1-2}$ alkyl-$C_6H_5$, —$C_{1-2}$ alkyl-p-Cl—$C_6H_4$, —$C_{1-2}$ alkyl-p-MeO—$C_6H_4$ and —$C_{1-2}$ alkyl-morpholino. In one variation of the above, $R^1$ and $R^2$ are each independently selected from H, methyl or ethyl. In another variation, each $R^3$ is independently methyl, ethyl, —$C_6H_5$, —$CH_2$—$C_6H_5$, p-MeO—$C_6H_4$— and —$CH_2CH_2$—N-morpholino.

In one embodiment, there is provided a method for improving the solubility of copper complexes by prior coordination as non-covalent derivatives (NCDs) as disclosed herein.

In one embodiment, the present application provides a compound of the Formula Ib:

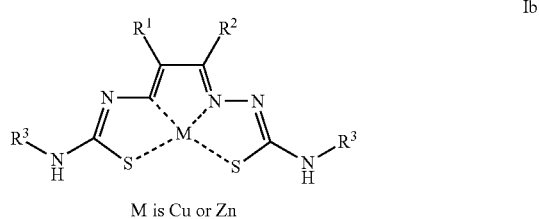

M is Cu or Zn

NCD compositions, regardless of stoichiometric relationship, of compounds of Formula Ib may be prepared with a ligand or coordinating ligand as disclosed herein, such as amino acids, ascorbic acid, caffeine, citric acid, glucose, gluconic acid, gluconic acid, glucuronic acid, glutathione, lactose, lactic acid, malic acid, maltose, saccharin, succinic acid and uric acid. In another embodiment, the application discloses the NCDs, various methods for preparing the NCDs and the NCDs prepared by the processes as provided herein.

BRIEF DESCRIPTION OF THE FIGURES

FIG. 9 is a representative depiction of average wire pull-up times of treated, MPTP-lesioned mice.

FIG. 10 is a representative depiction of the Neutral Red positive cell count in substantia nigra of treated, MPTP-lesioned mice.

FIG. 11 is a representative depiction of the average Cu-63 brain concentration in treated, MPTP-lesioned mice.

FIG. 12 is a representative depiction of the average Cu-63 plasma concentration in treated, MPTP-lesioned mice.

FIG. 13 is a representative depiction of certain results for a comparison of stool frequency between vehicle and treatment with Cu-ATSM.

DETAILED DESCRIPTION OF THE APPLICATION

Figure 1:
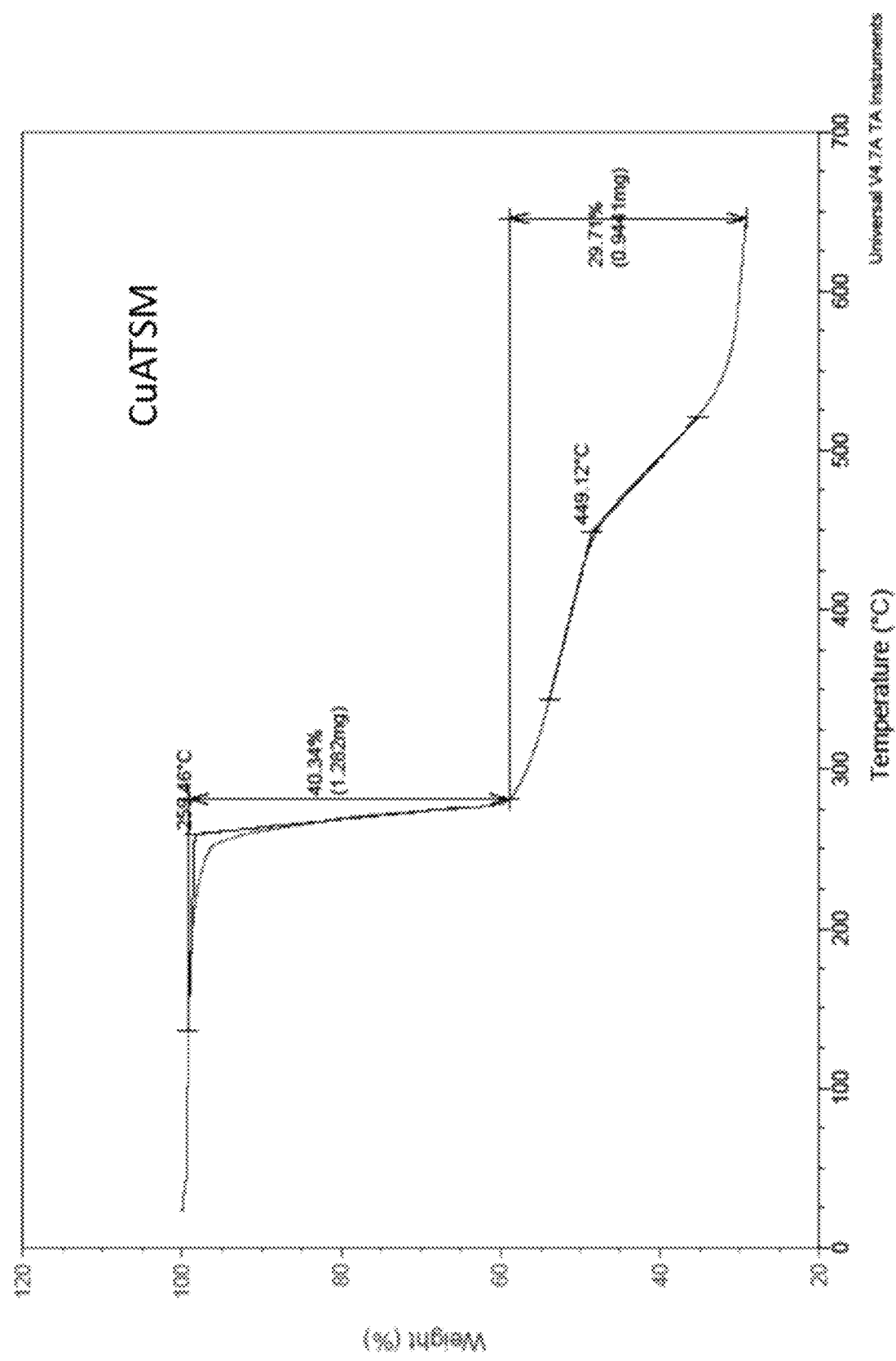
FIG. 1 is a representative depiction of a thermogravimetric analysis of a sample of CuATSM (Structure I, M=Cu; $R^1$ and $R^6$=H; $R^2$, $R^3$, $R^4$ and $R^5$=Me) used for preparation of malic acid NCD of FIG. 2.

The present application discloses the use of NCDs of metal complexes that are capable of delivering metal to biological sites, tissues or cells wherein metal is depleted in a patient. A number of important biological processes that are mediated by metals, such as metal mediated enzymes, occur in the cells rather than in the extra-cellular matrix. In one embodiment, the metal are delivered in the form of cell permeable NCDs of metal complexes in order to ensure that the metal acted on the cell rather than in the extra-cellular environment. In addition, the stable NCDs of the present application deliver the metal to the cell such that upon administration to a patient the metal is not released in the extra-cellular environment. A further advantage of the use of the NCDs of metal complexes over the free or "naked" metal ion is that delivery of the metal can be targeted, which reduces the chance that unwanted side effects will be observed (for example copper toxicity). A number of NCDs of metal complexes meet these criteria.

The properties of the metal complexes as their non-NCD complexes are typically retained on dissolution of the NCD of metal complexes, such that the inherent properties of the non-NCD metal complexes, including but not limited to cellular uptake, bioavailability, ability to cross the blood-brain-barrier, redox potential, or therapeutic efficacy, are maintained. In one aspect, the NCD of metal complexes may be administered as a solid or a solid dispersed in water, without the need for additional formulation.

Methods of Treatment, Ameliorating and/or Prophylaxis:

The NCD of metal complexes of the present application have been shown to be effective as metal delivery agents, particularly agents for the delivery of metals to cells. The NCD of metal complexes may be used in the treatment or prophylaxis of a number of conditions in which metal delivery can prevent, alleviate or ameliorate the condition. There are a number of conditions of this type. An example of conditions of this type is conditions associated with or caused by oxidative stress. It is known that many of the protective biological anti-oxidant mechanisms involve metal catalysed enzymes and thus metal delivery can serve to stimulate or re-start the activity of the biological anti-oxidant mechanisms leading to an overall anti-oxidant effect being achieved. In one embodiment the condition associated with or caused by oxidative stress is selected from the group consisting of cardiovascular conditions, cancers, cataracts, neurological disorders such as Alzheimer's disease, prion diseases—including Creutzfeldt-Jakob Disease (CJD), and heart diseases, amyloidogenic amyotrophic lateral sclerosis (ALS), prion transmissible spongioform encephalopathies (TSE), cataracts, mitochondrial disorders, Menkes disease, Parkinson's disease and Huntington's disease.

In another embodiment the disorder is a neuromuscular disorder selected from the group consisting of amyotrophic lateral sclerosis (ALS), mitochondrial/metabolic disease and Friedreich's ataxia. In one embodiment, the condition is a neurological condition or a neurodegenerative disorder.

Additionally, the NCD of metal complexes may also be used to potentiate the effects of other treatments, for example to potentiate the neuroprotective effects of brain derived nerve growth factor. The NCD of metal complexes may also be used to treat Anemia, Neutropenia, Copper deficiency Myelopathy, Copper deficiency Syndrome and Hyperzincaemia. In addition, the method of treatment is also directed to conditions which induce oxidative damage of the central nervous system, including acute and chronic neurological disorders such as, cerebral ischaemia, stroke (ischaemic and haemorragic), subharrachnoid haemorrage/cerebral vasospasm, cerebral tumour, AD, CJD and its new variant associated with "mad cow" disease, HD, PD, Friedrich's ataxia, cataract, dementia with Lewy body formation, multiple system atrophy, Hallerboden-Spatz disease, diffuse Lewy body disease, amyotrophic lateral sclerosis, motor neuron disease, multiple sclerosis, fatal familial insomnia, Gertsmann Straussler Sheinker disease and hereditary cerebral haemorrhage with amyloidoisis-Dutch type.

The method of treatment is also directed to the treatment of neurodegenerative amyloidosis. The neurodegenerative amyloidosis may be any condition in which neurological damage results from the deposition of amyloid. The amyloid may be formed from a variety of protein or polypeptide precursors, including but not limited to Aβ, synuclein, huntington or prion protein. In one embodiment, the condition is selected from the group consisting of sporadic or familial AD, ALS, motor neuron disease, cataract, PD, Creutzfeldt-Jacob disease and its new variant associated with "mad cow" disease, HD, dementia with Lewy body formation, multiple system atrophy, Hallerboden-Spatz disease, and diffuse Lewy body disease.

In another embodiment the neurodegenerative amyloidosis is an Aβ-related condition, such as AD or dementia associated with Down syndrome or one of several forms of autosomal dominant forms of familial AD (reviewed in St George-Hyslop, 2000). Most preferably the Aβ-related condition is AD. In another embodiment, prior to treatment the patient may have moderately or severely impaired cognitive function, as assessed by the AD Assessment Scale (ADAS)-cog test, for example an ADAS-cog value of 25 or greater. In addition to slowing or arresting the cognitive decline of a subject, the NCD of metal complexes and the methods of the invention may also be suitable for use in the treatment or prevention of neurodegenerative conditions, or may be suitable for use in alleviating the symptoms of neurodegenerative conditions. If administered to a patient who has been identified as having an increased risk of a predisposition to neurodegenerative conditions, or to a subject exhibiting pre-clinical manifestations of cognitive decline, such as Mild Cognitive Impairment or minimal progressive cognitive impairment, these NCD of metal complexes and their methods of use may be able to prevent or delay the onset of clinical symptoms, in addition to the effect of slowing or reducing the rate of cognitive decline.

Another condition that may be able to be treated by metal delivery using the NCD of metal complexes of the present application, is cancer. The term "cancer" describes any array of different diseases linked by cumulative multiple genetic mutations, which result in the activation of oncogenes and/or the inactivation of tumor suppressor genes and/or linked by uncontrolled cellular proliferation. The cause and source of these mutations differs between different cancers of human body organs.

In one embodiment, the present application is directed to brain cancer, which includes a brain tumor. A brain cancer or tumor may be a glioma or non-glioma brain tumor. As used herein, the term "cancer" and "tumor" may be used interchangeably herein. "Cancer" may include any one of the following states: glioma, adenoma, blastoma, carcinoma, sarcoma and inclusive of any one of Medulloblastoma, Ependymoma, Astrocytoma, Optical nerve glioma, Brain stem glioma, Oligodendroglioma, Gangliogliomas, Craniopharyngioma or Pineal Region Tumors. Reference to a "glioma" includes GMB, astrocytoma and anaplastic astrocytoma or related brain cancers.

The NCD of metal complexes of the present application may also be used to treat tau related disorders. Tau protein is an important protein as it is the protein expressed in the central nervous system and plays a critical role in the neuronal architecture by stabilizing intracellular microtubule network. Thus, any impairment of the physiological role of the tau protein either by truncation, hyper-phosphorylation or by disturbing the balance between the six naturally occurring tau isoforms is detrimental to the subject and leads to the formation of neurofibrillary tangles (NFT), dystrophic neurites and neuropil threads. The major protein subunit of these structures is microtubule associated protein tau. The amount of NFT found in autopsies of AD patients correlates with clinical symptoms including intellectual decline. Accordingly tau protein plays a critical role in AD pathology.

It is believed that the activity of the NCD of metal complexes of the present application that reduce the levels of tau phosphorylation is as a result of their ability to deliver metal to cells and hence their anti-oxidant activity. The complexes act as anti-oxidants may mean that they provide protection from OS which is desirable as OS can lead to hyper-phosphorylation of tau and cell dysfunction. As a consequence the ability of these complexes to deliver biologically important metals to cells allows them to function as anti-oxidants (especially where the oxidative stress is caused by metal deficiency) which in turn means the metal complexes may have the ability to prevent (or treat) tau-opathies. There are a number of disorders or conditions that are recognized as being tau disorders or more colloquially Tauopathies. Disorders of this type include Richardson's syndrome, Progressive Supranuclear Palsy, Argyrophilic grain disease, corticobasal degeneration, Pick's disease, frontotemporal dementia linked with parkinsonism linked to chromosome 17 9FTDP-17), post-encephalitic parkinsonism (PEP), dementia pugilistica, Down syndrome, Alzheimer's disease, Familial British dementia, Familial Danish dementia, Parkinson's disease, Parkinson's Disease complex of Guam (PDC), myotonic dystrophy, Hallevorden-Spatz disease and Niemann-Pick type C.

The NCD of metal complexes may also be used in the treatment of an Abeta related disorder. A number of Abeta disorders are known including disorders selected from the group consisting of Parkinson's disease, Alzheimer's disease, Multiple sclerosis, Neuropathies, Huntington's disease, Prion disease, motor neuron disease, Amyotrophic lateral sclerosis (ALS), Menkes disease and amyloidoses.

As the NCD of metal complexes have also been shown to be able to deliver metal to cells they have the ability to influence matrix metallo-proteinases (MMP's). Matrix metalloproteinases (MMPs) are a family of zinc- and calcium-dependent secreted or membrane anchored endopeptidases which play a number of important biological functions. MMPs are involved in many physiological processes but also take part in the pathophysiological mechanisms responsible for a wide range of diseases. Pathological expression and activation of MMPs are associated with cancer, atherosclerosis, stroke, arthritis, periodontal disease, multiple sclerosis and liver fibrosis.

In addition to slowing or arresting the cognitive decline of a subject, the NCD of metal complexes and the methods of the invention may also be suitable for use in the treatment, prevention or alleviation of gastrointestinal (GI) disease or disorder, such as constipation. If administered to a patient who has been identified as having an increased risk of a predisposition to neurodegenerative conditions and GI disease or disorder, or to a subject exhibiting pre-clinical manifestations of cognitive decline and associated GI disease or disorder, these metal complexes and their methods of use may be able to prevent or delay the onset of clinical symptoms, in addition to the effect of slowing or reducing the rate of cognitive decline, along with the treatment prevention or alleviation of the GI disease or disorder. While certain proposed mechanism of action are noted herein, the inventors do not intend to bound by any proposed or suggested mechanism of action in the present invention.

In one aspect, the NCDs may be administered via oral or non-oral methods, to a mammal without requiring the formulation with excipients, solubilizers and the like that are not acceptable for human use.

Administration of NCD of Metal Complexes:

Administration of the NCD of metal complexes of the Formula I, or Ib to humans can be performed by any of the accepted modes of administration well known in the art. For example they may be administered by enteral administration such as oral or rectal, or by parenteral administration such as subcutaneous, intramuscular, intravenous and intradermal routes. Injection can be bolus or via constant or intermittent infusion. The NCD of a metal complex is typically included in a pharmaceutically acceptable carrier or diluent and in an amount sufficient to deliver to the subject a therapeutically effective dose.

The NCD of metal complexes may be administered in any form or mode which makes the complex bio-available. One skilled in the art of preparing formulations can readily select the proper form and mode of administration depending upon the particular characteristics of the complex selected, the condition to be treated, the stage of the condition to be treated and other relevant circumstances. See Remingtons Pharmaceutical Sciences, 19$^{th}$ edition, Mack Publishing Co. (1995). In one aspect, the NCD of metal complexes can be administered alone or in the form of a pharmaceutical composition in combination with a pharmaceutically acceptable carrier, diluent or excipient.

Pharmaceutical compositions of the NCD of metal complexes for parenteral injection comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol, and the like), and suitable mixtures thereof, vegetable oils (such as olive oil), and injectable organic esters such as ethyl oleate. These compositions comprising the NCD of metal complexes may also contain adjuvants such as preservative, wetting agents, emulsifying agents and dispersing agents.

Solid dosage forms for oral administration include capsules, tablets, pills, powders, and granules. In such solid dosage forms, the active complex is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidone, sucrose and acacia, c) humectants such as glycerol, d) disintegrating agents such as agar-agar, calcium carbonate, potato or tapioca starch, alginic acid, certain silicates and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

In another aspect, the NCD of metal complexes that are labelled with radioactive isotopes, such as copper isotopes, including Cu-60, Cu-61 Cu-62 or Cu-64, may be used as radiopharmaceuticals for hypoxia imaging and the imaging of blood flow. Radiolabeled NCD of metal complexes of the present application may be used in positron imaging tomography (PET) studies since the complexes have a higher retention in hypoxic cells. Radiolabeled NCD of metal complexes, may be used as agents in clinical studies of lung cancer, uterine cervical cancer, gliomas, and other cancers ((Zeglis, Houghton, Evans, Viola-Villegas, & Lewis, 2014) (Lopci et al., 2014) (Anderson & Ferdani, 2009; Dearling & Packard, 2014; Dunphy & Lewis, 2009; Grassi et al., 2014; Jacobson & Chen, 2013; Lewis et al., 2008; Mees, Dierckx, Vangestel, & Van de Wiele, 2009; Wadas, Wong, Weisman, & Anderson, 2010; Zhu & Shim, 2011).

Non exclusive and representative examples of certain bis(thiosemicarbazone) chelators (XTSC) are shown in the Table below.

TABLE

Non-exclusive examples of bis(thiosemicarbazone) chelator, "XTSC".

| Chelator | $R^2 = R^6$ | $R^1 = R^5$ | $R^3$ | $R^4$ |
| --- | --- | --- | --- | --- |
| ATS | H | H | $CH_3$ | $CH_3$ |
| ATSM | H | $CH_3$ | $CH_3$ | $CH_3$ |
| ATSE | H | $C_2H_5$ | $CH_3$ | $CH_3$ |
| GTS | H | H | H | H |
| GTSM | H | $CH_3$ | H | H |
| PTS | H | H | $CH_3$ | H |
| PTSM | H | $CH_3$ | $CH_3$ | H |
| $PTSM_2$ | $CH_3$ | $CH_3$ | $CH_3$ | H |
| PTSE | H | $C_2H_5$ | $CH_3$ | H |
| PTSP | H | $C_6H_5$ | $CH_3$ | H |
| DTS | H | H | $C_2H_5$ | $C_2H_5$ |
| DTSM | H | $CH_3$ | $C_2H_5$ | $C_2H_5$ |

TABLE-continued

Non-exclusive examples of bis(thiosemicarbazone) chelator, "XTSC".

| Chelator | $R^2 = R^6$ | $R^1 = R^5$ | $R^3$ | $R^4$ |
|---|---|---|---|---|
| CTS | H | H | $C_2H_5$ | $CH_3$ |
| CTSM | H | $CH_3$ | $C_2H_5$ | $CH_3$ |
| ETS | H | H | H | $C_2H_5$ |
| C^yTSM (also referred to as ChexTSM) | H | $CH_3$ | —$C_4H_6$— | |

Definitions

Unless specifically noted otherwise herein, the definitions of the terms used are standard definitions used in the art of organic synthesis and pharmaceutical sciences. Exemplary embodiments, aspects and variations are illustrated in the figures and drawings, and it is intended that the embodiments, aspects and variations, and the figures and drawings disclosed herein are to be considered illustrative and not limiting.

As used herein, the term "unsubstituted" means that there is no substituent or that the only substituents are hydrogen.

The term "optionally substituted" as used throughout the specification denotes that the group may or may not be further substituted or fused, with one or more substituent groups. The substituent groups may be one or more groups independently selected from the group consisting of halogen, =O, =S, —CN, —$NO_2$, —$CF_3$, —$OCF_3$, alkyl, alkenyl, alkynyl, haloalkyl, cycloalkyl, cycloalkenyl, aryl, heteroaryl, cycloalkylalkyl, arylalkyl, hydroxy, hydroxyalkyl, alkoxy, alkoxyalkyl, alkoxyaryl, phenoxy, benzyloxy and arylalkyl.

"Alkyl" as a group or part of a group refers to a straight or branched aliphatic hydrocarbon group, such as a $C_1$-$C_{14}$ alkyl (or $C_{1-14}$ alkyl), $C_1$-$C_{10}$ alkyl or $C_1$-$C_6$ alkyl, unless otherwise noted. Examples of straight and branched $C_1$-$C_6$ alkyl substituents include methyl, ethyl, n-propyl, 2-propyl, n-butyl, sec-butyl, t-butyl, hexyl, and the like.

"Acyl" means an alkyl-CO— or HC(O)— group in which the alkyl group is as described herein. Examples of acyl include acetyl and benzoyl. The alkyl group is preferably a $C_1$-$C_6$ alkyl group.

"Alkenyl" as a group or part of a group denotes an aliphatic hydrocarbon group containing at least one carbon-carbon double bond and which may be straight or branched having 2-14 carbon atoms, 2-12 carbon atoms or 2-6 carbon atoms in the normal chain. The group may contain a plurality of double bonds in the normal chain and the orientation about each is independently E or Z. Exemplary alkenyl groups include, but are not limited to, ethenyl, propenyl, butenyl, pentenyl, hexenyl, heptenyl, octenyl and nonenyl.

"Alkoxy" refers to an —O-alkyl group in which alkyl is defined herein. Preferably the alkoxy is a $C_1$-$C_6$alkoxy. Examples include, but are not limited to methoxy and ethoxy.

"Alkynyl" as a group or part of a group means an aliphatic hydrocarbon group containing a carbon-carbon triple bond and which may be straight or branched preferably having from 2-14 carbon atoms, more preferably 2-12 carbon atoms, more preferably 2-6 carbon atoms in the normal chain. Exemplary structures include, but are not limited to, ethynyl and propynyl.

"Amino Acids" means the standard amino acids compounds that possess both an amino group and a carboxy function bonded to the same carbon, and include natural and unnatural amino acids, including alanine, arginine, asparagine, aspartic acid, cysteine, glutamic acid, glutamine, glycine, histidine, isoleucine, leucine, lysine, methionine, ornithine, phenylalanine, proline, serine, threonine, tryptophan, tyrosine and valine; and as disclosed herein.

"Aryl" as a group or part of a group denotes (i) an optionally substituted monocyclic, or fused polycyclic, aromatic carbocycle (ring structure having ring atoms that are all carbon) and may have from 5 to 12 atoms per ring. Examples of aryl groups include phenyl, naphthyl, and the like.

"Cycloalkyl" means saturated or partially unsaturated cyclic hydrocarbon radical having from three to twelve carbon atoms. Cycloalkyl may include 5-6 membered cycloalkyl groups, $C_3$-$C_6$ cycloalkyl groups, a 5-membered cycloalkyl or a 6 membered cycloalkyl group. The term "cycloalkyl" includes monocyclic and polycyclic (e.g., bicyclic and tricyclic) cycloalkyl structures, wherein the polycyclic structures optionally include a saturated or partially unsaturated cycloalkyl ring fused to a saturated, partially unsaturated or aromatic cycloalkyl or heterocyclic ring. The cycloalkyl may be optionally substituted independently with one or more substituents described herein. Examples of cycloalkyl groups include, but are not limited to, cyclopropyl, cyclobutyl, cyclopentyl, cyclohexyl, cyclohexadienyl, cyclooctyl, decalin and adamantane.

"Heteroalkyl" refers to a straight- or branched-chain alkyl group may have from 2 to 14 carbons or 2 to 10 atoms in the chain, one or more of which is a heteroatom selected from S, O, and N. Exemplary heteroalkyls include alkyl ethers, secondary and tertiary alkyl amines, alkyl sulfides, and the like.

"Heteroaryl" means an aromatic ring system including at least one N, O, S or P. "Heteroaryl" either alone or part of a group refers to groups containing an aromatic ring (such as a 5 or 6 membered aromatic ring) having one or more heteroatoms as ring atoms in the aromatic ring with the remainder of the ring atoms being carbon atoms. Suitable heteroatoms include nitrogen, oxygen and sulphur. Examples of heteroaryl include but are not limited to thiophene, benzothiophene, benzofuran, benzimidazole, benzoxazole, benzothiazole, benzisothiazol, pyridyl, dihydropyridyl, pyridazinyl, pyrimidinyl, pyrazinyl, s-triazinyl, oxazolyl, imidazolyl, thiazolyl, isoxazolyl, pyrazolyl, isothiazolyl, furanyl, thiofuranyl, thienyl and pyrrolyl.

A "Heterocycle" or "heterocyclyl" or "heterocycloalkyl" group means a saturated or partially unsaturated carbocyclic radical of 3 to 8 ring atoms in which at least one ring atom is a heteroatom independently selected from N, O and S, with the remaining ring atoms being C, where one or more ring atoms may be optionally substituted independently with one or more substituents described herein. In one embodiment, the heterocycle is a 4-6 membered heterocycle, a 5-6 membered heterocycle, a 5-membered heterocycle or a 6-membered heterocycle. Examples of heterocyclyl groups include, but are not limited to, pyrrolidyl, tetrahydrothiofuranyl, morphilino, 1,3-diazapane, 1,4-diazapane, 1,4-oxazepane, 1,4-oxathiapane, aziridinyl, azetidinyl, oxetanyl, piperidinyl, morpholinyl, piperazinyl, dihydropyranyl, dihydrofuranyl, tetrahydrofuranyl, tetrahydropyranyl, 1-pyrrolinyl, 2-pyrrolinyl, 3-pyrrolinyl, indolinyl, 2H-pyranyl, 4H-pyranyl, dioxanyl, 1,3-dioxolanyl, pyrazolinyl, pyrazolidinyl and imidazolidinyl.

The term "Ligand" or "ligand" refers to a co-additive, co-former, coordinating moiety, or an organic compound, as defined herein. The organic compound may have a molecular weight of less than 500.

The term "Metallated ligand" refers to a metal salt of a ligand, such as a deprotonated ligand. Non-exclusive representative examples may include a metal gluconate such as copper(II) gluconate or zinc(II) gluconate; metal lactate such as copper lactate; copper citrate, copper succinate etc, as disclosed herein.

The term "neurodegenerative disorder" refers to an abnormality in which neuronal integrity is threatened. Neuronal integrity can be threatened when neuronal cells display decreased survival or when the neurons can no longer propagate a signal. Neurological conditions that can be treated with the NCD of metal complexes of the present application include the conditions as recited herein.

The term "neurological condition" refers to conditions in which various cell types of the nervous system are degenerated and/or have been damaged as a result of neurodegenerative disorders or injuries or exposures. In particular, the NCD of metal complexes of the present application may be used for the treatment of resulting conditions, in which damage to cells of the nervous system has occurred due to surgical interventions, infections, exposure to toxic agents, tumours, nutritional deficits or metabolic disorders. In addition, the NCD of metal complex may be used for the treatment of the sequelae of neurodegenerative disorders, such as Alzheimer's disease, Parkinson's disease, multiple sclerosis, amyotrophic lateral sclerosis, epilepsy, drug abuse or drug addiction (alcohol, cocaine, heroin, amphetamine or the like), spinal cord disorders, dystrophy or degeneration of the neural retina (retinopathies) and peripheral neuropathies, such as diabetic neuropathy and/or the peripheral neuropathies induced by toxins.

"Non-Covalent Derivative" ("NCD", "NCD complex", "NCD of metal complex", or "co-crystal") means the derivative, complex or co-crystal derived from the metal complex of the Formula I, Ib as disclosed herein, and a ligand (a co-additive, co-former, coordinating moiety, compound, or co-crystal former) that result in a compound, complex or derivative in which the metal complex and the ligand are coordinated by noncovalent intermolecular interactions that result in the stabilization of the non-covalent derivative. Such interactions are often associated with the stabilization of proteins, drug-enzyme complexes, DNA and protein complexes etc. See for example, Meyer, Emmanuel A. et al., Angewandte Chemie, International Edition (2003), 42(11), 1210-1250; 1433-7851. English. As depicted herein, the product or result from the combination of the compound of the Formula I or Ib with a Ligand is an NCD, co-crystal or complex that is stabilized by non-covalent intermolecular interactions when compared to derivatives or admixtures lacking non-covalent intermolecular interactions. Such NCDs have significantly different physical properties (such as solubility, activity etc.) and electronic properties than a combination of two or more compounds that do not form NCDs. Representative NCDs are disclosed in Warner J C. In: Anastas P, Williamson T, editors. Green chemistry: frontiers in benign chemical synthesis and processes. London: Oxford University Press; 1998. p. 336-46. NCDs of the present application may be depicted generally, for example, as "X:Y" which means that it is an NCD of X with Y, such as "I: Ligand", "Ib: Ligand" etc.

"Non-Non-Covalent Derivative" or "non-NCD" or "non-NCD complex" or "non-NCD metal complex" means the metal complex as described herein that are not derived or prepared from a combination of the metal complex with a ligand as defined herein.

"Optionally substituted" means a substituent may be unsubstituted or may be further substituted by a substituent as defined herein.

The term "patient" as used herein refers to any animal having a disease or condition which requires treatment or prophylaxis with a biologically-active agent. The patient may be a mammal, such as a human, or may be a non-human primate or non-primates such as used in animal model testing. While the compounds are suitable for use in medical treatment of humans, it is also applicable to veterinary treatment.

The phrase "pharmaceutically acceptable" means that the compound, substance or composition is compatible chemically and/or toxicologically with the other ingredients comprising a formulation, and/or with the patient being treated.

The term "therapeutically effective amount" or "effective amount" is an amount sufficient to effect beneficial or desired clinical results. An effective amount can be administered in one or more administrations. An effective amount is typically sufficient to palliate, ameliorate, stabilize, reverse, slow or delay the progression of the disease state.

Generally, the terms "treatment" and "prophylaxis" mean affecting a subject, tissue or cell to obtain a desired pharmacological and/or physiological effect and include: (a) preventing the condition from occurring in a subject that may be predisposed to the condition, but has not yet been diagnosed as having it; (b) inhibiting the condition, i.e., arresting its development; or (c) relieving or ameliorating the effects of the condition, i.e., cause regression of the effects of the condition.

"Substituted" group, as in "substituted or unsubstituted alkyl" for example, means that the alkyl group may be unsubstituted, or substituted (where one or more hydrogens on the atom or group is replaced with one or more group) with a group selected from the group consisting of halo (F—, Cl—, Br— or I—), —CN, —NO$_2$, —OH, —SH, —OCH$_3$, $C_1$-$C_6$ alkyl (e.g., Methyl, ethyl, propyl, etc.) or phenyl.

EXPERIMENTAL

Methods for the preparation of the metal complexes and their methods for the treatment of various neurodegenerative diseases and disorders, are disclosed in PCT/AU2007/001792, published as WO2008/061306, which is incorporated herein in its entirety. Representative examples are provided herein.

Preparation of the Metal Complexes:

The complexes of the various embodiments may be prepared using the reaction routes and synthesis schemes as described below, employing the techniques available in the art for each of the individual step/reactions and using starting materials that are readily available. The synthesis of non-exemplified complexes may be performed by modifications apparent to those skilled in the art. Suitable protecting groups can be found in T. W. Greene's Protective Groups in Organic Synthesis, John Wiley & Sons, 1981.

NCDs consisting of a metal chelate "M(Chelator)$_{(n/x)}$" with a Ligand, where the NCD is of formula M(Chelator)$_{(n/x)}$:Ligand (p:n), may be prepared by physical mixing with applied pressure, such as by ball-milling, grinding with a mortar and pestle, or other physical mixing procedures, a chelating agent, consisting of the protonated chelator (Chelator)H$_x$ (x=1, 2, 3, 4, 5, . . . ), with a stoichiometric amount of the metallated ligand, typically the metal salt of the deprotonated ligand of formula[M$^{+n}$]$_p$ [(Ligand-pH)$^{-p}$]$_n$, so as to form the NCD M(Chelator)$_{(n/x)}$:

Ligand (p:n) of the metal chelate M(Chelator)$_{(n/x)}$ and the Ligand. [M$^{+n}$]$_p$[Ligand-pH$^{-p}$]$_n$+(n/x) (Chelator)H$_x$→pM(Chelator)$_{(n/x)}$:Ligand (1:n/p).

In one aspect of the present application, the NCDs may be prepared as disclosed in the various representations herein irrespective of the stoichiometry of the metal chelate: Ligand or of the chelating agent:Metallated Ligand. Accordingly, representative ratios of p:n may include 1:1, 1:2, 1:3, 2:1 and 3:1. In one aspect, the ratios of p:n is 1:1 or 1:2.

For example, method of preparing co-crystals of metal(II) bis(N-alkyl-hydrazinecarbothioamide) complexes with a ligand that consists of physical mixing with applied pressure, such as by ball-milling, grinding with a mortar and pestle, or other physical mixing procedures, the neutral, protonated chelating agent XTSCH$_2$ with one equivalent of the divalent metal salt of the deprotonated ligand so as to form the co-crystal M(II)XTSC:Ligand (1:2) of the metal(II) bis(N-alkyl-hydrazinecarbothioamide) complex, M(II)XTSC, and the Ligand:[M(II)]$_p$[(Ligand-pH)$^{-p}$]$_2$+p XTSCH$_2$→pM(II)XTSC:Ligand (1:2/p)

Also provided are methods of forming NCDs of divalent metal complexes with gluconic acid: M(II)[gluconate]$_2$+ XTSCH$_2$→MXTSC:gluconic acid (1:2).

Also disclosed are methods of forming CuATSM:gluconic acid (1:2), by combination of copper(II) gluconate with one equivalent of ATSMH$_2$ so as to form CuATSM: gluconic acid (1:2), such as by ball-milling or grinding with a mortar and pestle.

Cu(II)[gluconate]$_2$+ATSMH$_2$→CuATSM:gluconic acid (1:2)

Also disclosed are method of forming CuGTSM:gluconic acid (1:2), CuPTSM:gluconic acid (1:2), CuDTSM:gluconic acid (1:2), and ZnATSM:gluconic acid (1:2) by combination of the metal(II) gluconate with one equivalent of XTSMH$_2$: Cu(II)[gluconate]$_2$+GTSMH$_2$→CuGTSM:gluconic acid (1:2); Cu(II)[gluconate]$_2$+PTSMH$_2$→CuPTSM:gluconic acid (1:2); Cu(II)[gluconate]$_2$+DTSMH$_2$→CuDTSM:gluconic acid (1:2); Zn(II)[gluconate]$_2$+ATSMH$_2$→CuATSM: gluconic acid (1:2).

The reaction of the metal(II) salt of the ligand may be used to form an NCD with a Ligand for which the Ligand cannot readily be isolated as a neat compound. It is noted that gluconic acid cannot be isolated in linear form, rather, gluconic acid cyclizes to gluconic acid δ-lactone on isolation as a neat compound, precluding formation of the NCD by reaction of M(II)XTSC with ring-opened gluconic acid.

Preparation of certain complexes is shown below in Scheme 1.

(XIV)

Condensation of dione (X) with two equivalents of a suitably functionalized thio semicarbazide (XI) under acidic conditions leads to the formation of the bis (thiosemicarbazone) (XIII). The bis(thiosemicarbazone) can then be reacted with a suitable metal salt such as the metal acetate to produce the desired metal complex (XIV) and acetic acid. A wide variety of thiosemicarbazones may be produced by varying the substituents on either the aldehyde moiety or on the semicarbazide.

An alternative procedure for preparing non-symmetrical (bis semicarbazones) is shown in Scheme 2:

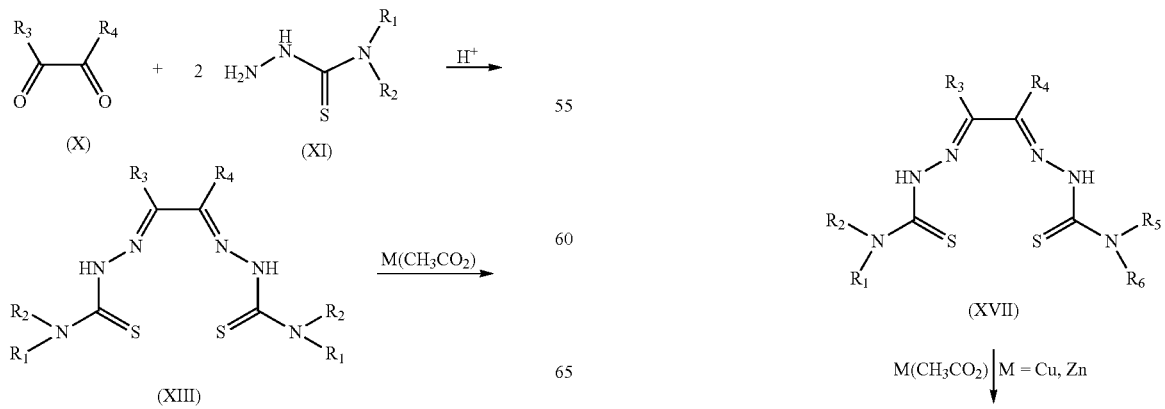

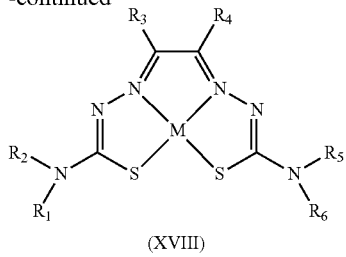

(XVIII)

A dione (X) with one equivalent of thio semi-carbazide (XI) under acidic conditions leads to formation of the mono thio semicarbazione derivative (XV). Condensation with a second thiosemicarbazide moiety (XVI) produces a bis (thiosemicarbazone) (XVII) which can be reacted with a metal salt such as the metal acetate to produce the desired unsymmetrical complex (XVIII).

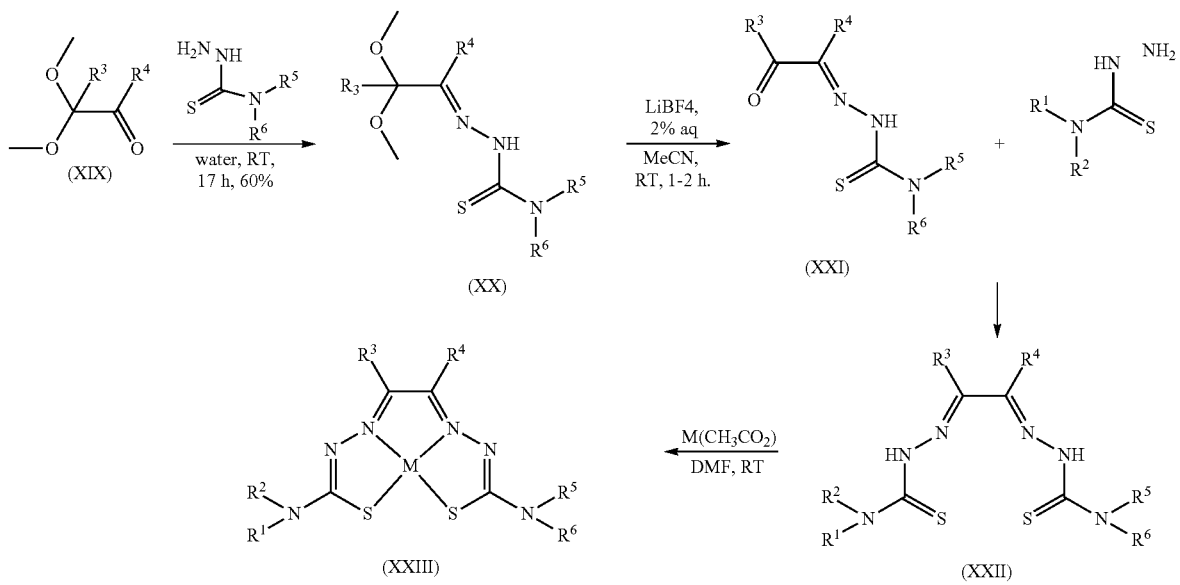

Scheme 3: Alternative Formation of unsymmetrical bis(thiosemicarbozones).

(XIX) was reacted with a thiosemicarbazides to afford the mono-adduct, acetal (XX). The acetal can be oxidatively cleaved to give the aldehyde (XXI) using lithium tetrafluoroborate. Reaction of the aldehyde (XXI) with a different thiosemicarbazide, gave the desired asymmetric chelating agent (XXII) which could then be converted into the metal complex (XXIII) using the standard conditions.

EXAMPLES

Various starting materials and other reagents are purchased from commercial suppliers, such as Aldrich Chemical Company or Lancaster Synthesis Ltd. ATSMH$_2$, [Cu(ATSM)], [Zn(ATSM)], ATSPH$_2$, [Cu(ATSP], [Zn(ATSP)]. Other metal complexes are prepared by variations of reported procedures, see: 1) P. J. Blower et al., Dalton Trans., 2003, 4416-4425 and references therein; 2) J. L. J. Dearling et al., J. Biol. Inorg. Chem., 2002, 7, 249 and references therein; 3) P. McQuade, K. E. Et al., Nucl. Med. Biol., 2005, 32, 147.

Reactions were carried out in air unless stated otherwise. 400 MHz $^1$H NMR spectra were obtained on a JEOL AS 400 spectrometer. HPLC were obtained on an Agilent 1100 HPLC. LC-MS were obtained on an Agilent 1260 LC-MS equipped with UV and MS detectors. Thermal gravimetric analysis (TGA) was performed using a TA Instruments model TGA 5000-00228 with the sample held under nitrogen. Differential Scanning Calorimetry (DSC) was performed on a TA Instruments Q2000-0984, with the sample held under nitrogen, and using a single heating temperature ramp. FTIR spectra were obtained on a Nicolet 6700 FT-IR instrument operating in either absorbance mode, for samples prepared in KBr pellets, or in attenuated total reflection (ATR) mode for neat solid samples.

Synthesis of ATSMH$_2$ (free chelator, also called chelating agent). (2E)-2,2'-(butane-2,3-diylidene)bis-(N-methylhydrazinecarbothioamide), ATSMH$_2$, was prepared similarly to methods reported. To a well-stirred warm solution of (Z)—N-methylcarbamohydrazonothioic acid 1 (0.08 mol) in 10% ethanolic HCl (200 mL) was added drop-wise a solution of diacetyl 2 (0.04 mol) in ethanol (25 mL) was over 45 minutes at room temperature. After the addition was complete, a light yellow dispersion was observed which was refluxed for 12 h. The reaction mixture was allowed to attain room temperature and the resulting light yellow precipitate was vacuum filtered, washed with water (3×50 ml) followed by cold ethanol (3×10 mL) and then vacuum dried to afford the desired ATSMH$_2$ product 3, (2E)-2,2'-(butane-2,3-diylidene)bis-(N-methylhydrazinecarbothioamide) as an off-white solid in 84% yield. The product identity was confirmed by $^1$H-NMR (400 MHz, DMSO-d6) δ 8.56 (s, 1H), 7.80 (s, 1H), 4.41 (s, 2H), 2.86 (d, 3H), 2.20 (s, 3H); LRMS: 261.10 (M+H)$^+$.

The following XTSMH$_2$ free chelating agents were prepared similarly: GTSMH$_2$, PTSMH$_2$, DTSMH$_2$ and C$^y$TSMH$_2$.

Compounds of Formula I, Ia and Ib were prepared similarly to known methods as reported in Inorg. Chem. 2007, 46, 465 (Holland et al., 2007) and J. Biol. Inorg. Chem. 2002, 7, 249 (Dearling, 2002).

Synthesis of Copper(II) diacetyl-di(N4-methyl)thiosemicarbazone, "CuATSM": To a pale yellow solution of ATSMH$_2$ (0.01 mol, 2.60 g) in dry ethanol (5 mL) was added [Cu(OAc)$_2$] H$_2$O (0.013 mol, 2.60 g) in portions over 10 minutes where upon the reaction mixture started turning into a tan colored suspension. The reaction was stirred overnight at 60° C. The resulting dark red mixture was allowed to cool to ambient temperature and the solid product collected by vacuum filtration from the dispersion. The iridescent precipitate was washed sequentially with ethanol (10 mL), deionized water (10 mL), and diethyl ether (20 mL), and then vacuum dried to afford CuATSM as a reddish-brown fine powder in 45% yield. LRMS: 322.01 (M+H)$^+$.

Single-crystal x-ray diffraction confirmed the identity of the product as CuASTM with no co-crystallized solvent molecules. The structure in agreement with that published (J. Am. Chem. Soc. 2002, 124, 5270-5271) (Andrew R. Cowley, Dilworth, Donnelly, Labisbal, & Sousa, 2002). The CuATSM was also characterized by X-ray powder diffraction (XRPD).

CuATSM is characterized by a single exotherm in the DSC at a temperature on or about 228° C. The temperature of the exotherm depends on the rate of heating and also shows some batch-to-batch variation. The Thermogravimetric Analysis (TGA) of CuATSM shows the onset of decomposition on or about 240-245° C., with approximately 34% solids remaining at 600° C. The TGA decomposition temperature depends on the rate of heating and also shows some batch-to-batch variation. The FTIR of CuATSM from 650 to 4000 cm$^{-1}$ shows absorbance maxima at 3321.9, 3016.9, 2978.8, 2925.9, 2892.2, 2844.5, 1650.6, 1614.6, 1523.8, 1494.2, 1467.7, 1364.7, 1364.7, 1325.5, 1264.2, 1243.1, 1222.4, 1188.5, 1156.9, 1116.9, 1076.3, 1054.6, 1033.3, 945.6, 888.1, 869.1, 840.7, 728.7, 690.5 and 659.1 cm$^{-1}$.

Chromatography (HPLC and LC/MS) of CuATSM was run using a Poroshell 120 EC-C18 4.6×50 mm 2.7 um column. Mobile phase was a gradient of 5% to 100% over 3 min and then held at 100% acetonitrile for 1.5 min Solvents were 0.05% TFA in acetonitrile and 0.05% TFA in water. Flow rate was at 0.75 ml/min and detection was carried out with a UV detector at 254 nm, 230 nm and a low-resolution mass spec detector. Only a single peak in the HPLC (UV detection) with elution time about 3.3 min is observed. The mass spectrum at the 3.3 min elution time shows a base peak at m/z 322.0, corresponding to (M+1)$^+$ of the most abundant of the possible isotopic ions of formula C$_8$H$_{15}$CuN$_6$S$_2^+$, CuATSMH$^+$.

Synthesis of CuGTSM: CuGTSM was made similarly by reaction of GTSMH$_2$ and [Cu(OAc)$_2$]H$_2$O. CuGTSM is characterized by a single sharp exotherm in the DSC at a temperature on or about 209° C.

Synthesis of CuDTSM: CuDTSM was made similarly by reaction of DTSMH$_2$ and [Cu(OAc)$_2$]H$_2$O. Synthesis of CuPTSM: CuPTSM was made similarly by reaction of PTSMH$_2$ and [Cu(OAc)$_2$]H$_2$O. Synthesis of CuC$^y$TSM: CuC$^y$TSM was made similarly by reaction of C$^y$TSMH$_2$ and [Cu(OAc)$_2$]H$_2$O.

Synthesis of [Zn(ATSE)]

ATSEH$_2$ (0.134 g) and Zn(CH$_3$CO$_2$)$_2$·2H$_2$O (0.102 g) are added to ethanol (5 mL) The mixture is heated at reflux for 2 hours under nitrogen and then cool to room temperature. The yellow solid that formed is collected by filtration and washed with ethanol, and diethyl ether to give [Zn(ATSE)] as a yellow powder (0.122 g, 76%). $^1$H NMR shows that the spectrum is consistent with the desired product.

Synthesis of ChexTSE 1,2-Cyclohexanedione (0.439 g) is added to ethanol (25 mL) followed by N4-ethyl-3-thiosemicarbazide (0.933 g) and a few drops of H$_2$SO$_4$(conc). The mixture is heated at reflux under an atmosphere of nitrogen for 3 hours and then allowed to cool to room temperature. A yellow precipitate is collected by filtration and washed with ethanol and diethyl ether to obtain ChexTSE as a yellow solid (0.945 g, 76%). $^1$H NMR shows that the spectrum is consistent with the product.

Preparation of NCD Complexes, Analytical Characterization, and Evaluation of Bioavailability, Blood-Brain Barrier Uptake, Efficacy in Mouse Models of PD and Animal Testing:

In another aspect of this disclosure, compounds of Formula I and Ib form materials of distinct character when treated with a ligand to form a non-covalent derivative, as represented with Ib, below.

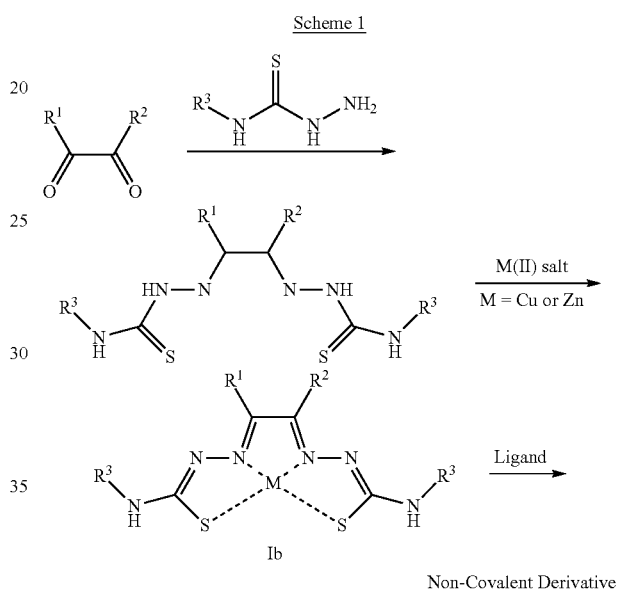

Scheme 1

Ib

Non-Covalent Derivative

Synthetic Generation of Organo-Cupric Noncovalent Derivatives:

The compounds of Formula Ib when R$^1$, R$^2$, and R$^3$ are —H and/or methyl were prepared according to Inorg. Chem. 2007, 46, 465 and J. Biol. Inorg. Chem. 2002, 7, 249.

TABLE 1

Compounds Synthesized.

| Compound | Synthesis (Example number) |
| --- | --- |
| CuATSM | Metal Chelate |
| CuATSM:citric acid (1:1) | EXAMPLE 4 |
| CuATSM:saccharin (1:2) | EXAMPLE 3 |
| CuATSM:gluconic acid (1:2) | EXAMPLE 7 |
| CuATSM:L-Tyrosine methyl ester (1:1) | EXAMPLE 4 |
| CuATSM:Alanine ethyl ester (1:1) | EXAMPLE 2 |
| CuATSM:L-cystine di-methyl ester (1:2) | EXAMPLE 6 |
| CuATSM:Thiodipropionic acid (1:1) | EXAMPLE 2 |
| CuATSM:malic acid (1:1) | EXAMPLE 1 |
| CuGTSM | Metal Chelate |
| CuGTSM:saccharin (1:2) | EXAMPLE 5 |
| CuGTSM:gluconic acid (1:2) | EXAMPLE 9, EXAMPLE 10 |
| CuGTSM:Alanine ethyl ester (1:1) | EXAMPLE 2 |
| CuGTSM:N-tetraethyl terephthalamide (1:1) | EXAMPLE 2 |
| CuGTSM:Citric acid (1:1) | EXAMPLE 2 |
| CuPTSM | Metal Chelate |

TABLE 1-continued

Compounds Synthesized.

| Compound | Synthesis (Example number) |
|---|---|
| CuPTSM:saccharin (1:2) | EXAMPLE 4 |
| CuPTSM:gluconic acid (1:2) | EXAMPLE 11 |
| CuDTSM | Metal Chelate |
| CuDTSM:saccharin (1:2) | EXAMPLE 4 |
| CuDTSM:gluconic acid (1:2) | EXAMPLE 12 |
| CuC$^y$TSM | Metal Chelate |
| ZnATSE | Metal Chelate |
| ZnATSM:gluconic acid (1:2) | EXAMPLE 8 |

Example 1

Small-scale method of preparation of noncovalent derivatives of M-XTSM as an NCD with a coordinating moiety by co-crystallization from stoichiometric solution in hot solvent. To a 30 mL vial were added 50 mg CuATSM (0.155 mmol), 0.155 mmol of a selected one of the ligands, and 15 mL of either acetone or acetonitrile. This mixture was shaken by hand while heating the vial in a water bath at 74° C. until all solids dissolved. The solution was quickly filtered while hot through a 45-μ syringe filter into a clean glass vial. The vial was then capped loosely, and allowed to cool to room temperature. The solvent was then allowed to evaporate slowly evaporate over the course of several weeks at room temperature until crystals were observed. The crystals (non-covalent derivatives) were isolated by removing the remaining liquid via pipette, and drying the resulting crystals under vacuum at room temperature. Compounds that were prepared in this fashion include CuATSM:malic acid (1:1).

FIG. 1 depicts the thermogravimetric analysis (TGA) of a particular batch of CuATSM whose structure is of Formula I ($R^1$ and $R^6$=H; $R^2$, $R^3$, $R^4$ and $R^5$=Me) used to prepare the CuATSM:malic acid (1:1), and for which the TGA of the NCD is shown in FIG. 2.

The thermogravimetric analysis (TGA) of a ligand, Malic Acid, shows the onset of weight loss at a lower temperature, on or about 201° C., with more than 99% loss before a temperature of 250° C.

Figure 2:
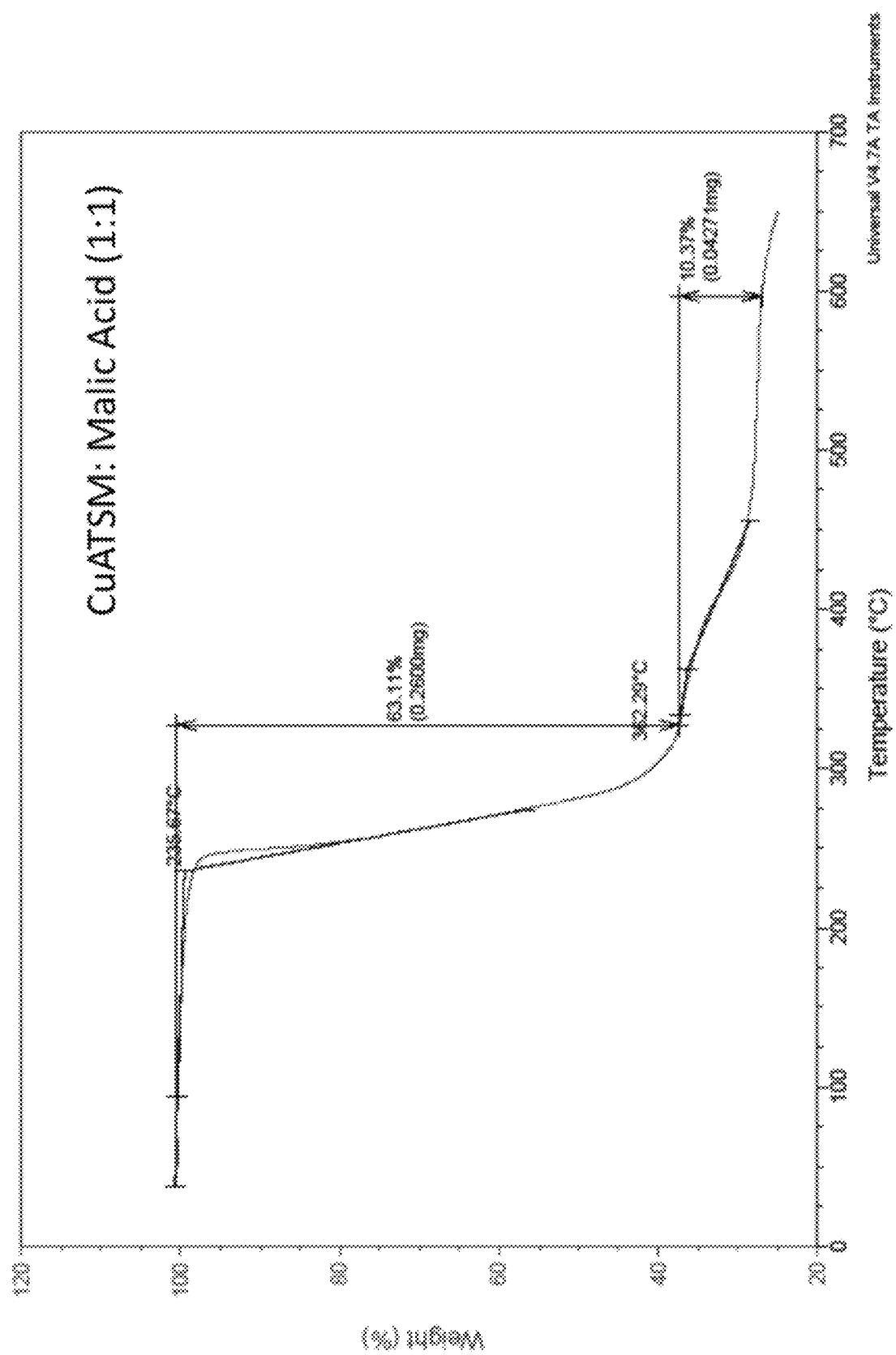
FIG. 2 is a representative depiction of a Thermogravimetric analysis of a non-covalent derivative of CuATSM with Malic Acid (1:1).

FIG. 2 depicts the thermogravimetric analysis (TGA) analysis of a (1:1) noncovalent derivative(NCD) of CuATSM, CuATSM:malic acid (1:1).

The TGA weight loss as a function of temperature for the non-covalent derivative, FIG. 2, is noteworthy in that the lower temperature weight loss, i.e., first decomposition temperature, approximately 236° C., FIG. 2, is at a temperature intermediate between and distinctly different from the first decomposition temperature of either CuATSM, approximately 259° C., FIG. 1, or of malic acid, 201° C.

Example 2

Method of preparation of noncovalent derivatives of M-XTSM as an NCD with a coordinating moiety by co-crystallization from room temperature acetone:

The preparation of Non-Covalent Derivatives of M-XTSM of Formula I is conducted by mixing room temperature solutions of MXTSM and the ligand and allowing to stand. In a 500 mL round bottom flask equipped with stir bar was dissolved CuATSM (0.166 g, 0.516 mmol) in 200 mL of room temperature acetone, with stirring, resulting in a 0.00258M CuATSM solution. Separately, a solution of a selected coordinating compound in acetone was prepared and then added to 20 mL of 0.00258M CuATSM solution (0.0516 mmol CuATSM) in a crystallizing dish. The solutions were gently mixed and then the crystalizing dish was covered loosely with foil and allowed slowly evaporate over the course of several weeks until crystals were observed. Crystals were then isolated by removing any remaining liquid via pipette, and drying the resulting crystals under vacuum. An NCD of CuATSM and saccharin was prepared by dissolving 22.7 mg (0.124 mmol) saccharin in 2 mL of acetone, and adding the resulting solution to 20 mL of 0.00258M CuATSM (0.0516 mmol) in acetone. A brown power (26.2 mg) was obtained following slow solvent evaporation and drying of the isolated crystals.

Compounds made similarly include: CuATSM:Alanine Ethyl Ester (1:1), CuATSM:Thiodipropionic acid (1:1), CuGTSM:Alanine ethyl ester (1:1), CuGTSM:N-tetraethyl terephthalamide (1:1), and CuGTSM:Citric acid (1:1).

Example 3

Large-scale, hot-solvent preparation of non-covalent derivatives of M(II)XTSM. To a suspension of CuXTSM (1.0 mmol) of Formula I (M=Cu; $R^1$ and $R^6$=H; $R^2$ and $R^5$=Me) in acetone (3 L) was added the ligand in the appropriate stoichiometric ratio of 1:1 or 1:2 depending on the ligand. The resulting dispersion is mixed vigorously while heating in a water bath held at 70° C. until essentially all the solids had dissolved in the acetone. The hot solution was quickly filtered through a 45-μ syringe filter into a round-bottom flask. The solvent volume was reduced to approximately half. The remaining solution was transferred into a crystallizing dish, capped loosely and allowed to cool and slowly evaporate until crystals were observed. The crystals were filtered, washed with several times with acetone and vacuum dried to afford the NCDs. CuATSM:saccharin (1:2) was made according to this procedure, by reaction of 0.322 g (1.0 mmol) of CuATSM with 0.366 g (2.0 mmol) of saccharin.

Figure 3:
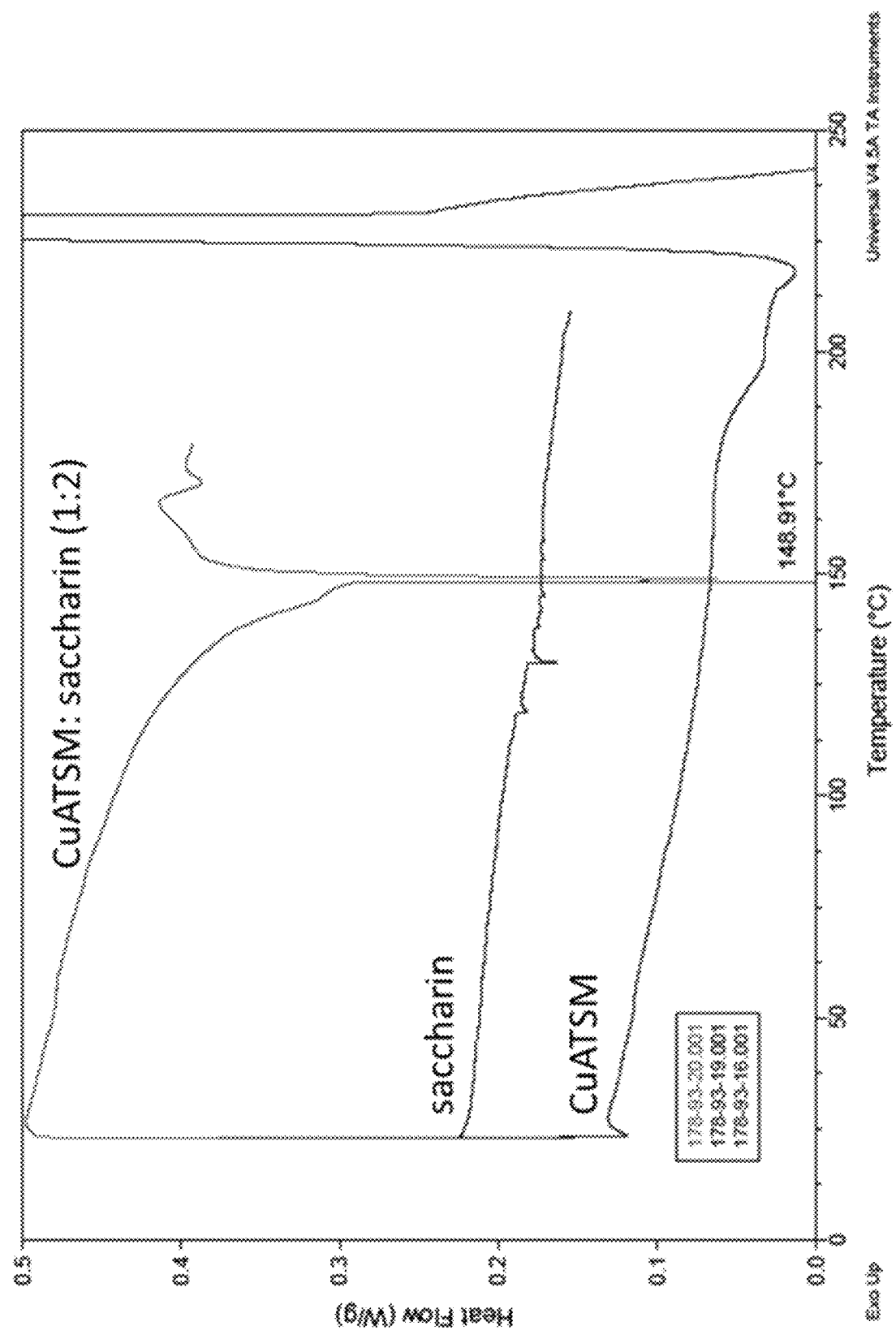
FIG. 3 is a representative depiction of a DSC of CuATSM:saccharin (1:2) compared to the DSC of CuATSM and of saccharin.

The DSC of the thus-formed CuATSM:saccharin (1:2), CuATSM and saccharin are shown in FIG. 3. The DSC of the thus-formed CuATSM:saccharin (1:2) shows a sharp endotherm on or about 149° C., which is distinct from the strong exotherm of CuATSM on or about 228° C., and is also distinct from that of saccharin which consists of a series of much smaller endotherms in the region approximately 120-160° C.

Example 4

CuATSM:citric acid (1:1), CuATSM:L-tyrosine methyl ester (1:1), CuDTSM:saccharin (1:2), and CuPTSM:saccharin (1:2) were prepared similarly to the methods of EXAMPLE 3.

CuDTSM:saccharin (1:2), and CuPTSM:saccharin (1:2) were characterized by LC/MS. Each showed two peaks in the chromatogram, consistent with their dissociation into the constituent molecules, saccharin and the metal complex, on dissolution in the carrier solvent.

Example 5

Figure 4:
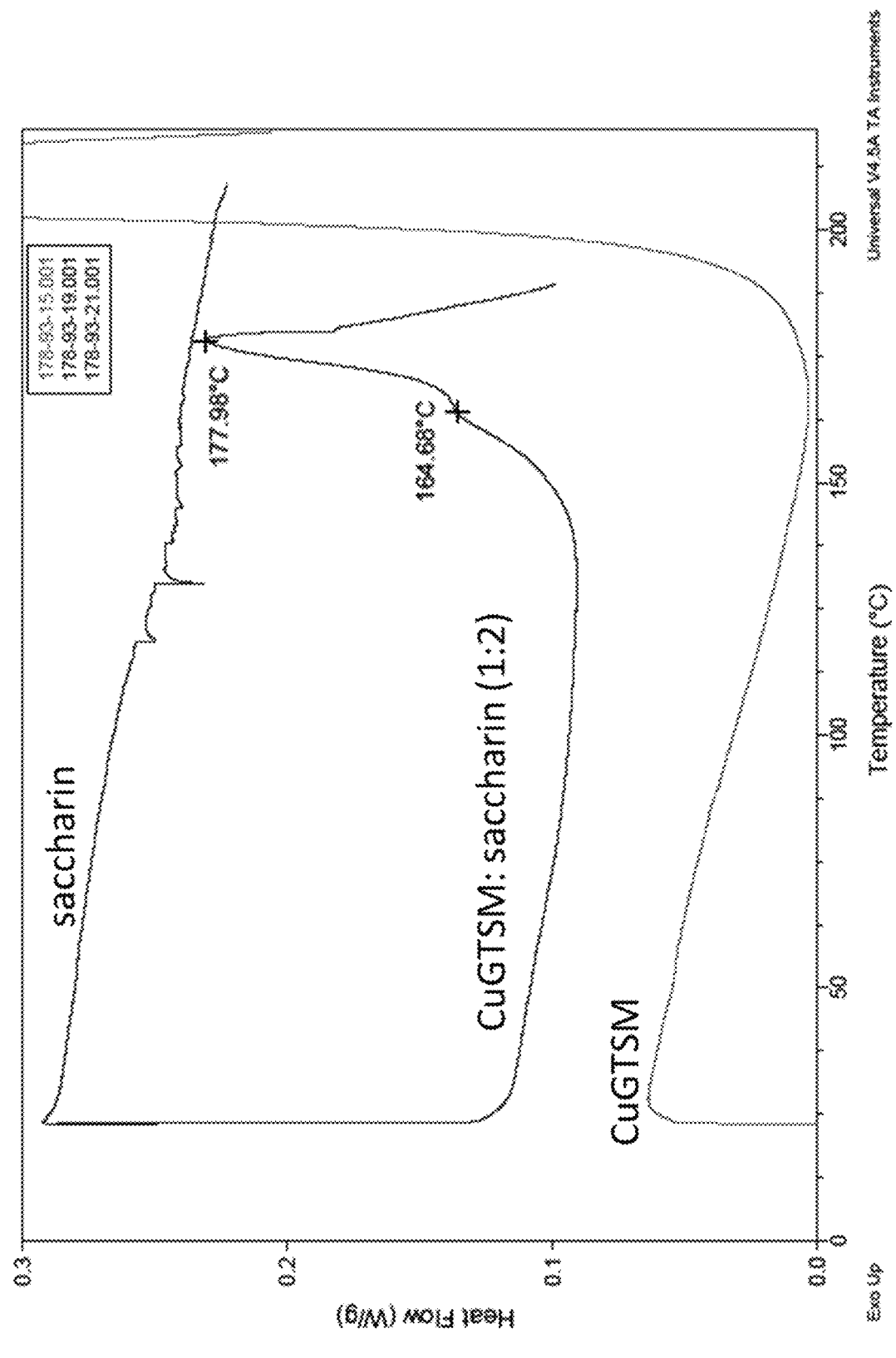
FIG. 4 is a representative depiction of a DSC of CuGTSM:saccharin (1:2) compared to DSC of saccharin and of CuGTSM.

CuGTSM:saccharin (1:2) was prepared from CuGTSM and saccharin similarly to the methods of EXAMPLE 3. The DSC of the thus-formed CuGTSM:saccharin (1:2), CuGTSM, and saccharin are shown in FIG. 4. The DSC of the thus-formed CuGTSM:saccharin (1:2) shows a broad exotherm on or about 178° C., with a shoulder on or about 165° C. that is distinct from the strong exotherm of CuGTSM on or about 209° C. The DSC of CuGTSM: saccharin (1:2) is also distinct from that of saccharin, which has a series of much smaller endotherms in the region approximately 120-160° C.

Example 6

Method of forming NCD by dissolution of CuATSM and a ligand in water.

CuATSM (20 mg, 0.0621 mmol) was added to a test tube, and 10 ml of water was then added to the sample in the test tube. The mixture was briefly shaken, and then 2 equivalents (84.8 mg, 0.1243 mmol) of the ligand L-cystine dimethyl ester as the dihydrochloride was added into the test tube, and the mixture shaken until the ligand fully dissolved. The mixture was then allowed to stand. The mixture was then filtered, and the filtrate collected and taken to dryness by lyophilization, yielding 22.4 mg of red-brown solid.

course of the 90 min ball-milling, as determined by the lack of change in the DSC, FTIR, HPLC and TGA taken of the separately-milled copper(II) gluconate and $ATSMH_2$. After 90 min of milling, the mixture of (1:1) $ATSMH_2$ and copper(II) gluconate resulted in a pale-tan product. The CuATSM:gluconic acid (1:2) product was removed from the vial, vacuum dried and stored in a tightly-capped vial.

Elemental analysis: Calculated for $C_{20}H_{38}CuN_6O_{14}S_2$: C, 33.63; H, 5.36; Cu, 8.90; N, 11.77; 0, 31.36; S, 8.98. Found: C, 33.94; H, 5.09; Cu, 8.65; N, 11.12.

Figure 5:
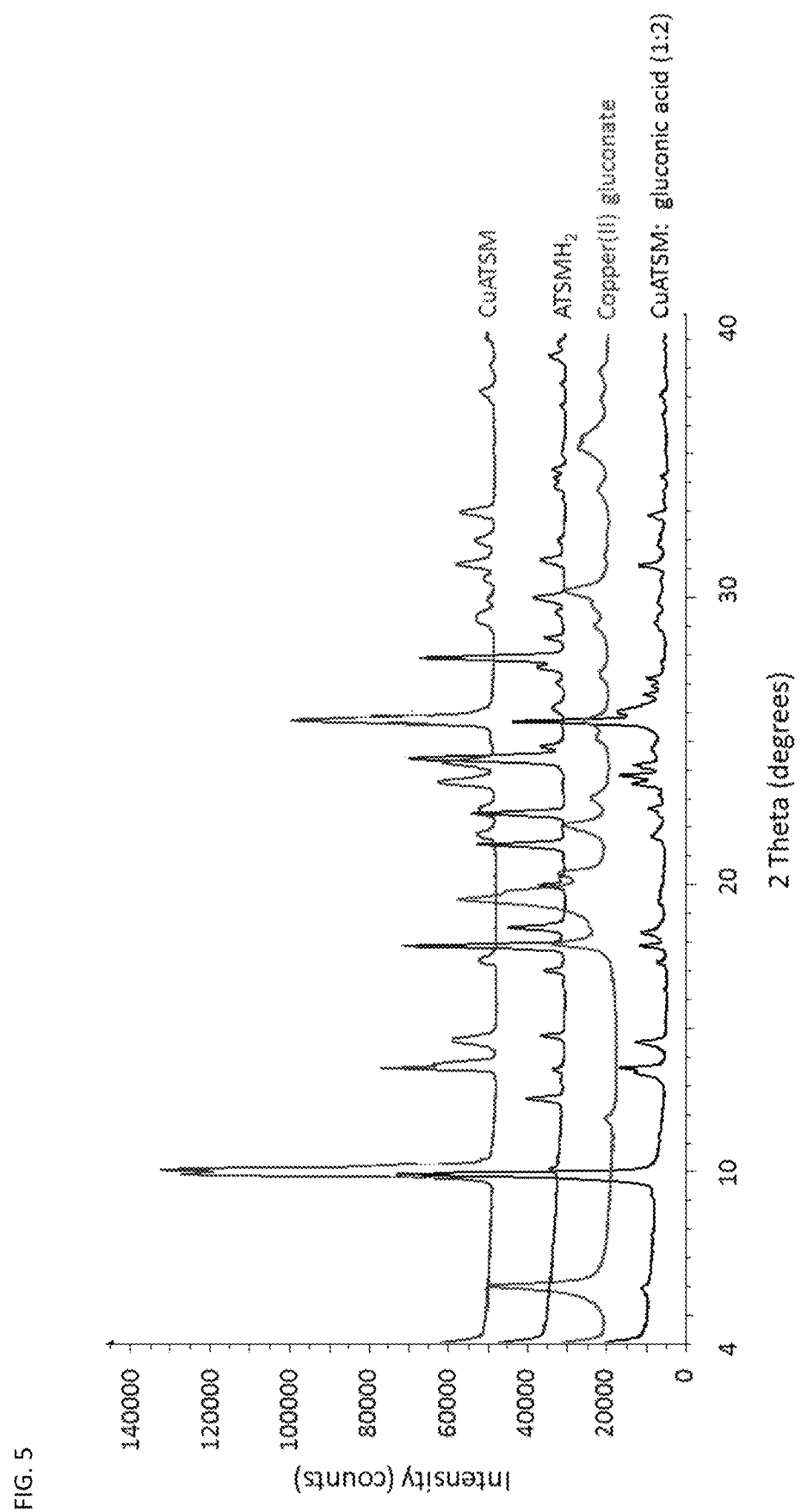
FIG. 5 is a representative depiction of an X-ray powder diffraction (XRPD) spectrum of CuATSM:gluconic acid (1:2) prepared by ball-milling, with comparison to XRPD spectra of copper(II) gluconate and ATSMH$_2$ starting materials, and to XRPD spectrum of CuATSM. Spectra are offset vertically from one another by 10000 counts.
Figure 6:
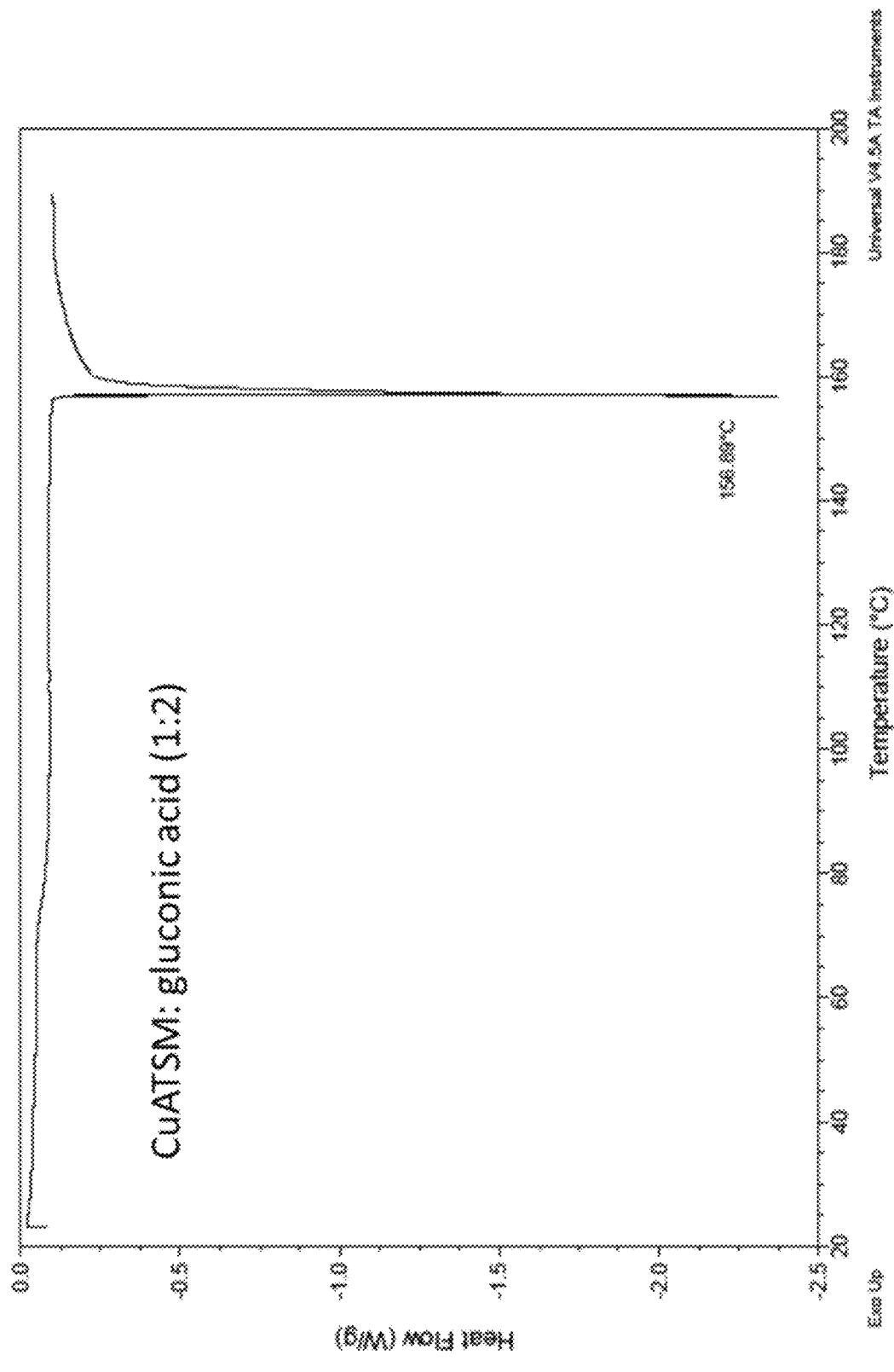
FIG. 6 is a representative depiction of a DSC of CuATSM:gluconic acid (1:2) product of 90-minute ball-milling of ASTMH$_2$ with Cu(II) gluconate.

The product CuATSM:gluconic acid (1:2) was characterized by X-ray powder diffraction XRPD, and is compared to the XRPD of copper(II) gluconate and $ASTMH_2$ starting materials, and to the XRPD of CuATSM in FIG. 5. The product CuATSM:gluconic acid (1:2) has a sharp endotherm in the DSC on or about 157° C., FIG. 6. The observed transition temperature of the endotherm varies, depending on the rate of heating and batch-to-batch variation. The

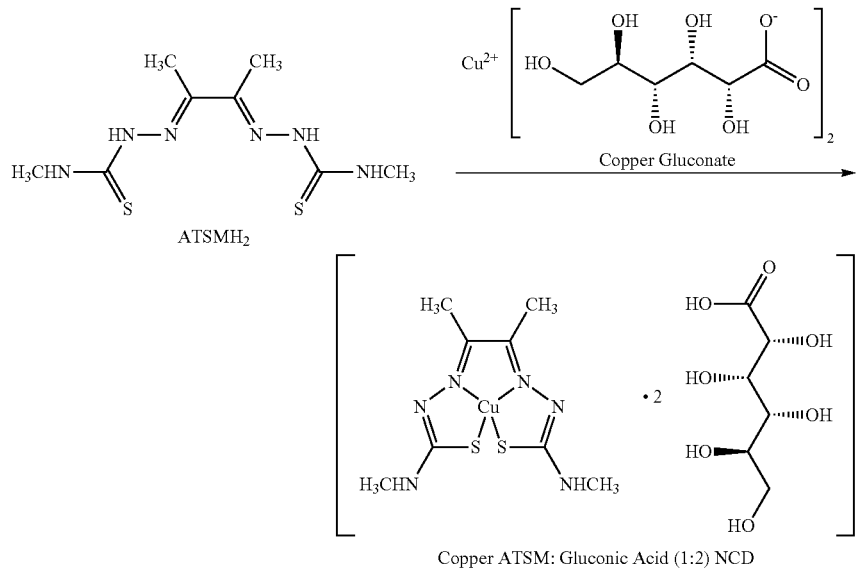

Example 7

Method of preparation of noncovalent derivatives of M-XTSM by solvent-free ball milling of a mixture of $XTSMH_2$ and M(II) salt of the deprotonated ligand:

In a dry mortar were placed pre-weighed solids of off-white $ATSMH_2$ (259 mg, 1 mmol) and blue anhydrous copper(II) D-gluconate (453 mg, 1 mmol). The solids were slowly mixed with a spatula until a uniform mixture of the two crystalline components was obtained. The resulting mixed powder was transferred into a SPEX 5-mL polystyrene grinding vial with slip-on cap, followed by careful addition of one SPEX ⅜-in diam. methacrylate grinding ball, and then the vial was capped tightly. A separate vial was loaded with $ATSMH_2$, and another separate vial was loaded with copper(II) gluconate. All three vials were placed in a small high-energy ball mill, SPEX 5100 Mixer/Mill, operating at 3000 rpm. The milling was started and the contents of each of the three vials monitored after 30 min, 60 min and 90 min of milling by HPLC and FTIR, DSC and TGA.

No evidence of decomposition of the separately-milled copper(II) gluconate or $ATSMH_2$ was evident over the observed transition temperature typically occurs in the range of 150° C. to 160° C. The endotherm is not observed in the DSC of CuATSM, FIG. 3.

Figure 7:
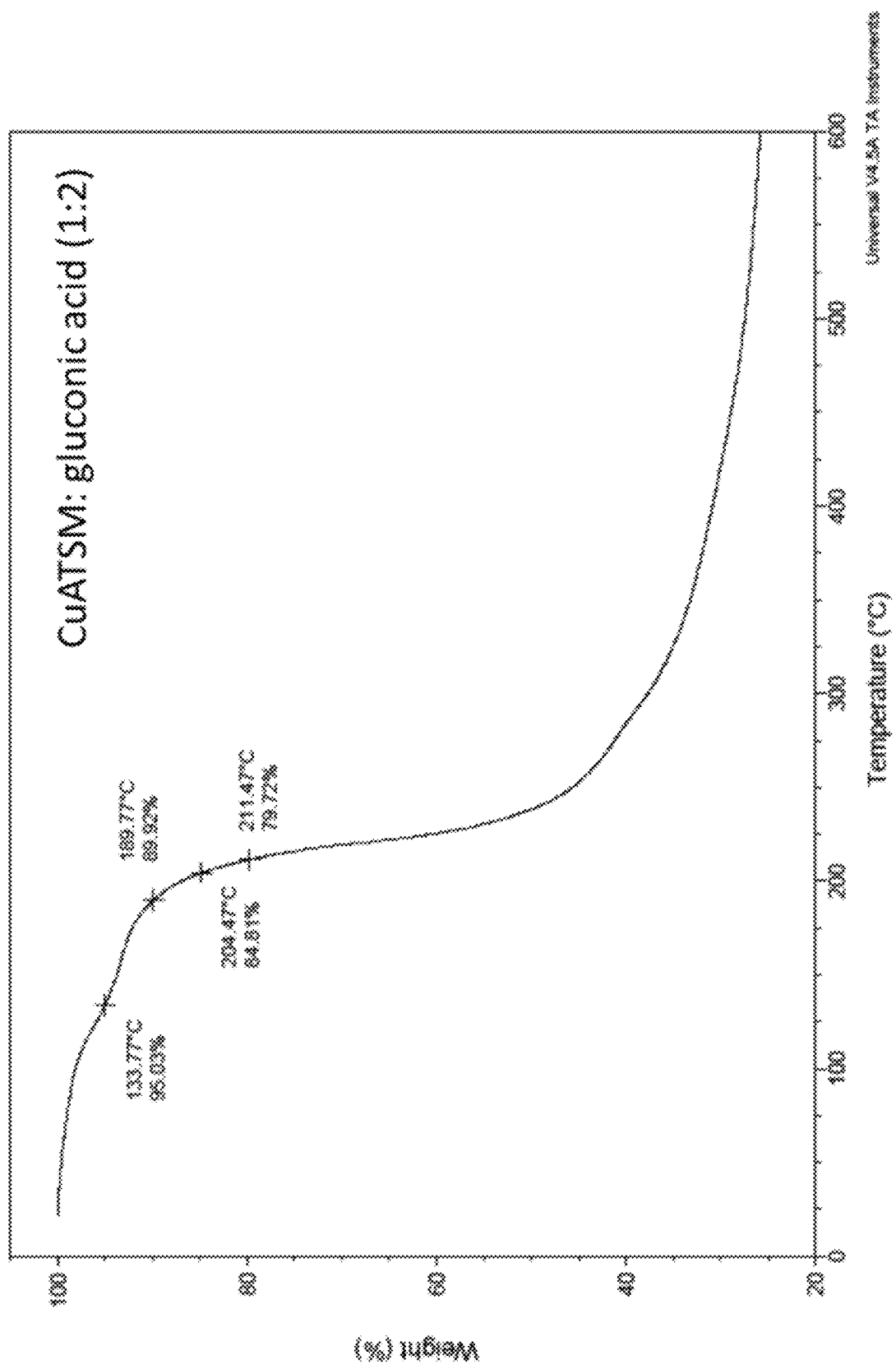
FIG. 7 is a representative depiction of a Thermogravimetric analysis (TGA) of CuATSM:gluconic acid (1:2) product of 90-minute ball-milling of ASTMH$_2$ with Cu(II) gluconate.

The thermogravimetric analysis (TGA) of the CuATSM: gluconic acid (1:2) product is given in FIG. 7. There is an initial approximately 5% weight loss that may be attributable to water desorption from the sample. There is a rapid weight loss observed beginning approximately 190° C., and approximately 26% solids remain at 600° C. By comparison, the TGA of CuATSM indicates that CuATSM decomposes rapidly at a higher temperature of approximately 240-245° C., and approximately 34% solids remain at 600° C. The FTIR of the product CuATSM:gluconic acid (1:2) from 650 to 4000 $cm^{-1}$ shows absorbance maxima at 3356.9, 3232.3, 2935.4, 2898.3, 1650.5, 1613.4, 1544.3, 1487.0, 1434.3, 1415.3, 1390.9, 1350.7, 1218.4, 1170.1, 1129.4, 1073.1, 1054.2, 1026.5, 955.9, 887.1, 868.6, 817.1, 797.4, 727.1 and 688.2 $cm^{-1}$.

The product CuATSM:gluconic acid (1:2) was chromatographed (HPLC and LC/MS) using the same methodology as used for CuATSM, using a Poroshell 120 EC-C18 4.6×50 mm 2.7 um column. Mobile phase was a gradient of 5% to 100% over 3 min and then held at 100% acetonitrile for 1.5 min. Solvents were 0.05% TFA in acetonitrile and 0.05% TFA in water. Flow rate was at 0.75 ml/min and detection was carried out with a UV detector at 254 nm, 230 nm and a low-resolution mass spec detector. Only a single peak with elution time about 3.3 min is observed. The low-resolution LC/MS of CuATSM:gluconic acid (1:2) is similar to the low-resolution LC/MS of CuATSM. As is found for the LC/MS of CuATSM, the base peak is found at m/z 322.0, which corresponds to $(M+1)^{\pm}$ of the most abundant of the possible isotopic ions of formula $C_8H_{15}CuN_6S_2$, that is, $CuATSMH^+$.

Example 8

Preparation of Zn-ATSM:gluconic acid (1:2)

Zn-ATSM:gluconic acid (1:2) was synthesized by ball-milling of 0.5 mmol $ATSMH_2$ (130 mg) with anhydrous zinc(II) gluconate (227 mg) for 90 minutes, similarly to the method described in EXAMPLE 7 for the synthesis of CuATSM:gluconic acid (1:2). The product identity of ZnATSM:gluconic acid (1:2) was confirmed by $^1H$ NMR: (400 MHz, DMSO-d6) δ 7.18 (broad s, 2H), 4.53 (very broad s, 1H), 4.31 (very broad s, 1H), 4.08 (m, 2H) 3.91 (d, 2H), 3.57 (s, 2H), 3.33 (broad/m, 14H), 2.82 (d, 6H), 2.19 (s, 6H); the remaining 2H (presumed to be the acidic carboxylic acid protons on gluconic acid) were not located. The peaks at δ 7.18 (broad s, 1H), 2.82 (d, 3H), 2.19 (s, 3H) in the $^1H$ NMR of ZnATSM:gluconic acid (1:2) are indistinguishable from those observed for an authentic sample of ZnATSM prepared from zinc(II) acetate and $ATSMH_2$.

Example 9

CuGTSM:gluconic acid (1:2) was prepared by 90-minute ball-milling of $GTSMH_2$ with copper(II) gluconate, similarly to the methods of EXAMPLE 7. The product exhibits a sharp endotherm in the DSC on or about 125° C.

Example 10

CuGTSM:gluconic acid (1:2) was prepared by 120-minute ball-milling of $GTSMH_2$ with copper(II) gluconate, similarly to the methods of EXAMPLE 7 and EXAMPLE 9. The product has a sharp endotherm in the DSC on or about 134° C., and a second sharper endotherm in the DSC on or about 152° C.

Example 11

CuPTSM:gluconic acid (1:2) was prepared by 120-minute ball-milling of $PTSMH_2$ with copper(II) gluconate, similarly to the methods of EXAMPLE 7. The product has a sharp endotherm in the DSC on or about 165° C.

Example 12

CuDTSM:gluconic acid (1:2) was prepared by 90-minute ball-milling of $DTSMH_2$ with copper(II) gluconate, similarly to the methods of EXAMPLE 7. The product has a sharp endotherm in the DSC on or about 147° C., and a second sharper endotherm in the DSC on or about 172° C.

Example 13

Kinetic Solubility determination of CuATSM; Comparative Example and Method.

Solubility assays were performed in 25 mL glass vials. Glass vials (4-mL, capped, VWR) were used to prepare stock solutions. All experiments were conducted using µDISS Profiler™ operated by µDISS Command Software (version 5.0.1.0). MB-8 mini-water bath with built-in stirring device was used to provide stirring during solubility measurements. Temperature during experiments was maintained at 25±2° C., and were performed in duplicate.

An HCl/KCl based buffer at pH 1.2 and a simulated intestinal fluid at pH 6.8 (no pancreatin) were prepared according USP protocols (Vol 35/NF30). The pH values of the solutions were confirmed with a pH Meter (Thermo Scientific Orion®, Benchtop Model 420 equipped with 9157BN Triode™ pH-electrode) and were all found to be within ±0.05 pH unit from the expected values. The concentration measurements are performed directly in the dissolution media, with processed results plotted in real time using the µDISS Profiler™ (Pion) instrument. The Profiler uses an in situ fiber optic-dip probe UV apparatus, with the probe center-positioned in the vial holding the studied compounds and 10-20 mL of media. Interference due to background turbidity was minimized when needed by a spectral second derivative method (Avdeef, A; Tsinman, O. "Miniaturized Rotating Disk Intrinsic Dissolution Rate Measurement: Effects of Buffer Capacity in Comparisons to Traditional Wood's Apparatus", *Pharm. Res.*, 2008, DOI: 10.1007/s11095-008-96-79-z).

The 2 and 20 mm path length tips were selected for detecting the concentration of CuATSM at pH 1.2 and pH 6.8 respectively. A dry CuATSM powder was dissolved in DMSO resulting a stock solution at known concentration, and then the solution was used to generate standard curves by serial addition. Standard curves were determined from the area under the second derivative curve in wavelength range 340-366 nm (for pH 1.2) and 445-465 nm (for pH 6.8) so as to avoid over saturation of the UV signal. Linearity of the standard curves in the selected wavelength region was r2≥0.998 for the selected concentration ranges.

The solubility of CuATSM were determined in pH 6.8 buffer. Samples of CuATSM were introduced into pH 6.8 buffer as powders, thus, unlike for standards, the final solutions contained no solvents in the background. The 20 mm (at pH 6.8) path length tip was selected for detecting the concentration of CuATSM in solution. All experiments were performed at room temperature 25±3° C. CuATSM was added to the assay vial so as to limit the upper concentration limit of CuATSM in the solubility assay to approximately 0.15 mg/mL. The concentration of pure CuATSM reached its maximum at approximately 0.45 µg/mL after approximately 8 hours and remained at that concentration for the duration of the 12-hour monitoring period.

Example 14

Kinetic solubility determination of CuATSM:citric acid (1:1).

CuATSM:citric acid (1:1) was prepared according to the methods of EXAMPLE 4.

The samples of the non-covalent derivative CuATSM:citric acid (1:1) were introduced into pH 6.8 buffer as powders, thus, unlike for standards, the final solutions contained no solvents in the background. The 20 mm pathlength tip was selected for detecting the concentration of the compounds in pH 6.8 buffer solution. All experiments were performed at room temperature, 25±3° C., and were performed in duplicate.

The standards generated for CuATSM were used to calculate the concentration of CuATSM in the solubility assays for CuATSM:citric acid (1:1) since the spectral data showed no significant difference between the shape of the UV-profiles of CuATSM and CuATSM:citric acid (1:1). CuATSM:citric acid (1:1) was added to the assay vial so as to limit the upper concentration limit of CuATSM:citric acid (1:1) in the solubility assay to approximately 0.15 mg/mL. Following addition of CuATSM:citric acid (1:1) to pH 6.8 buffer, approximately 0.9 µg/mL maximum concentration of CuATSM was reached within 0.3 hours. Beginning at approximately 0.3 h, the concentration of CuATSM in solution decreases, such that by the end of the 12-hour monitoring period the concentration of CuATSM had decreased to approximately 0.6 µg/mL, with the concentration of CuATSM still continuing to decrease slowly with time. The level of dissolved CuATSM was less than 1% of the 0.15 mg/mL maximum available in the assay.

Example 15

Kinetic solubility determination of CuATSM:saccharin (1:2). CuATSM:saccharin (1:2) was prepared according to the methods of EXAMPLE 3. The kinetic solubility profile of CuATSM:saccharin (1:2) was determined in pH 6.8 buffer similarly to the methods given in EXAMPLE 13 and EXAMPLE 14. Standard curves of CuATSM:saccharin (1:2) and saccharin were generated and compared to the standard curves of CuATSM. Saccharin concentrations in the buffer solution were determined from the saccharin standard curves in the 292-310 nm wavelength region, using the Zero Intercept Method so as to minimize spectral interference from CuATSM. CuATSM concentrations were determined from the CuATSM (neat) standard curves in the 445-465 nm region, where saccharin absorbances do not interfere. The upper concentration limit of the assay was approximately 0.12 mg/mL of CuATSM:saccharin (1:2), resulting in upper concentrations limits for CuATSM and for saccharin in solution approximately 60 µg/mL each. All experiments were performed at about 25±3° C., and were performed in duplicate.

Following addition of CuATSM:saccharin (1:2) to pH 6.8 buffer, approximately 2 µg/mL maximum concentration of CuATSM was reached within 0.8 hours. Beginning at approximately 0.8 h, the concentration of CuATSM in solution decreased, such that by the end of the 12 hours monitoring period the concentration of CuATSM had decreased to approximately 1 µg/mL, with the concentration of CuATSM still decreasing with time.

The amount of dissolved CuATSM remained less than 1% of the total amount of CuATSM in the CuATSM:saccharin (1:2) sample.

At the same time, the concentration of saccharin was monitored. Following addition of CuATSM:saccharin (1:2) to pH 6.8 buffer, approximately 60 µg/mL maximum concentration of saccharin was reached within 0.3 hours, remaining essentially unchanged over the 12-hour monitoring period. This concentration of saccharin is equivalent to, within error limits, complete dissolution of the available saccharin in the introduced sample.

Example 16

Kinetic solubility of CuATSM:gluconic acid (1:2) at pH 6.8. CuATSM:gluconic acid (1:2) was prepared according to the method of EXAMPLE 7. The kinetic solubility profile of CuATSM:gluconic acid (1:2) was determined in pH 6.8 buffer similarly to the methods given in EXAMPLE 13 and EXAMPLE 14. It was found that the CuATSM:gluconic acid (1:2) did not fully dissolve at 0.4 mg/mL in DMSO. Standard curves for CuATSM:gluconic acid (1:2) were therefore generated from serial dilution of a stock solution in DMSO at approximately 0.4 mg/mL nominal concentration, and compared to the standard curves of CuATSM. The upper concentration limit of the solubility assay was approximately 0.2 mg/mL CuATSM:gluconic acid (1:2) resulting in upper concentrations limits of approximately 0.09 mg/mL CuATSM and approximately 0.11 mg/mL gluconic acid.

Following addition of CuATSM:gluconic acid (1:2) to the pH 6.8 buffer, the CuATSM absorption at 450 nm was shifted to 415 nm within the first 0.3 hours. By approximately 0.5 hours after addition of CuATSM:gluconic acid (1:2) to the buffer, the spectral features in the region 280 nm to 360 nm were also shifted in wavelength and intensity. These spectral shifts are indicative of a change in the chemical identity—reaction or decomposition—of the CuATSM following dissolution of CuATSM:gluconic acid (1:2) in pH 6.8 buffer. Therefore, only the spectral data obtained within the 0 to 0.3-hour time interval was used to estimate the concentration of CuATSM resulting from dissolution of CuATSM:gluconic acid (1:2). The standard curves generated for CuATSM were used for determination of the concentration of CuATSM resulting from dissolution of CuATSM:gluconic acid (1:2) in pH 6.8 buffer, using the area under the second derivative curve in the 300-310 nm wavelength range. Following addition of CuATSM:gluconic acid (1:2) to pH 6.8 buffer, approximately 3 µg/mL maximum concentration of CuATSM was reached within 0.11 hours.

The amount of dissolved CuATSM in solution at the 0.3 hour time point was less than 1% of the total available CuATSM contained in the CuATSM:gluconic acid (1:2) sample.

Example 17

Kinetic solubility of CuATSM:gluconic acid (1:2) at pH 1.2, KCl/HCl buffer. A portion of the same sample CuATSM:gluconic acid (1:2), prepared according to the method of EXAMPLE 7, and that was used for determination of solubility at pH 6.8, was used to determine the kinetic solubility at pH 1.2. The upper concentration limit of the assay was approximately 0.7 mg/mL resulting in the upper concentrations limits of CuATSM to be approximately 0.3 mg/mL and that of gluconic acid to be approximately 0.4 mg/mL. The standards collected for CuATSM at pH 1.2 were used to determine the concentration of (1:2) CuATSM:gluconic acid in pH 1.2 buffer, using the area under the second derivative curve in the 340-366 nm wavelength range.

Following addition of CuATSM:gluconic acid (1:2) to pH 1.2 buffer, approximately 195 µg/mL maximum concentration of CuATSM was reached within approximately 0.3 hours (18-20 minutes). The concentration of CuATSM in solution then remained without change for the remaining 3-hour (180-minute) monitoring period.

The amount of dissolved CuATSM increased in parallel to the concentration, rising to 33% of the total amount of CuATSM in the CuATSM:gluconic acid (1:2) sample within 0.3 hours (18-20 minutes), and remaining at that level for the duration of the 3-hour (180-min) monitoring period.

Example 18

Solubility determination: Solubilities of CuATSM and the non-covalent derivatives CuATSM:citric acid (1:1), CuATSM: L-Tyrosine methyl ester (1:1), CuATSM:cystine dimethyl ester (1:2), and CuATSM:saccharin (1:2) were measured using a method designed to enable determination of the equilibrium solubilities.

CuATSM:saccharin (1:2) was prepared according to the methods of EXAMPLE 3. CuATSM:citric acid (1:1) and CuATSM:L-Tyrosine methyl ester (1:1) were prepared according to the methods of EXAMPLE 4. CuATSM:cystine dimethyl ester (1:2) was prepared according to the methods of EXAMPLE 6.

Sample powders of CuATSM and selected non-covalent derivatives of CuATSM were weighed (2.5 mg) into clean glass vials. Buffer (2.5 mL) corresponding to one of the selected pH values 1.2, 4.0, 6.8, 7.4 and 9.0 was added to each vial. The upper solubility limit of the assay is 1.0 mg/mL, as determined by the amount of CuATSM and buffer. The vials were capped, parafilmed and vortexed for 10 seconds at the top speed using a Vortex Genie-2. The samples were then incubated for about 20 hours at room temperature with agitation.

The solutions containing suspensions of the solid were then filtered (0.2 μm pore microfilter), and the supernatant solutions were assayed for the amount of CuATSM present, by comparison with UV spectra (230 to 500 nm) obtained from reference standards of CuATSM. The method is described in U.S. Pat. No. 6,569,686.

Figure 8:
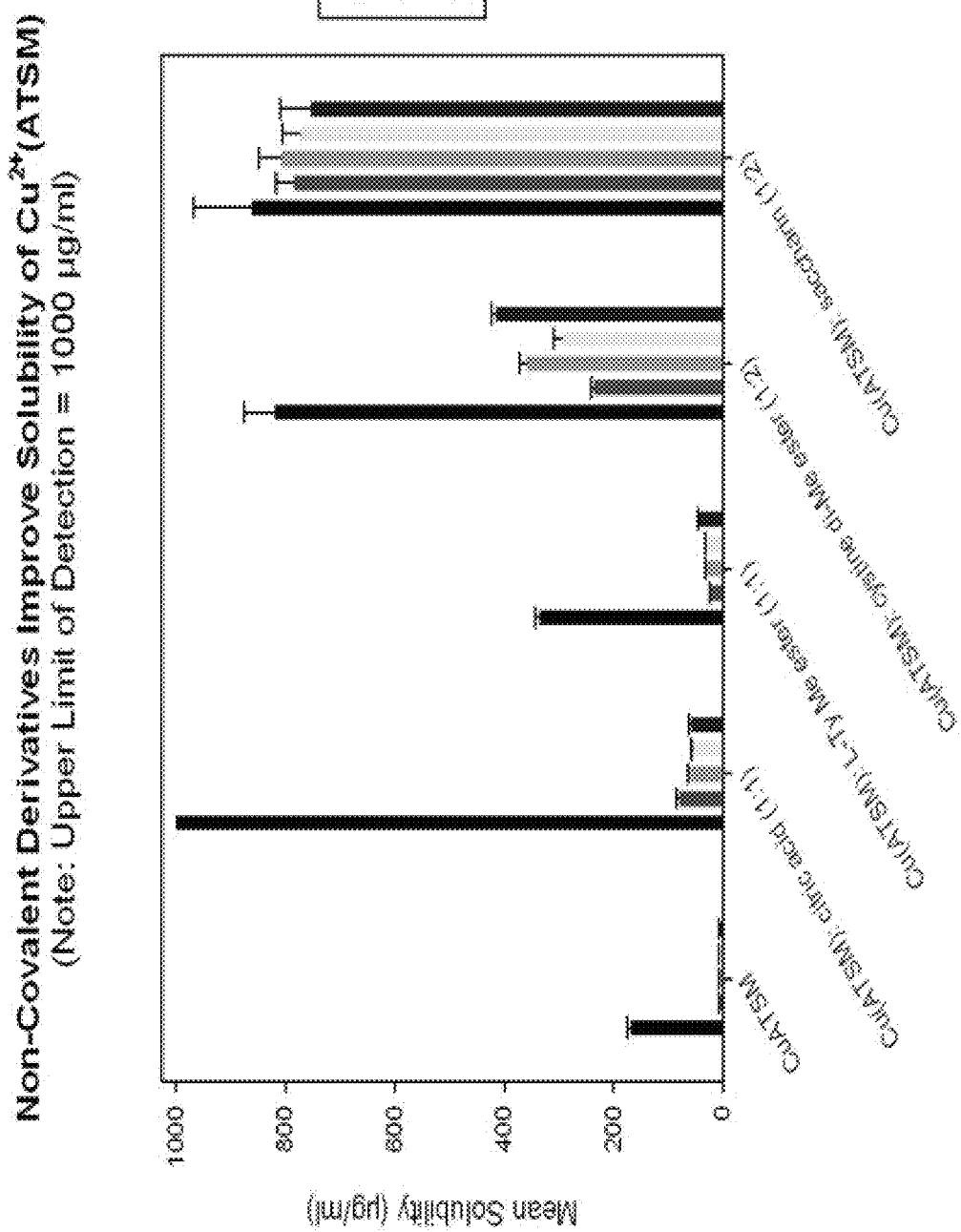
FIG. 8 is a representative depiction of the solubilities of non-covalent derivatives of CuATSM in various buffers, determined from the solution spectra following 20-hour incubation of buffer with solid compound.

The aqueous solubility thus measured of noncovalent derivatives of Formula I were found by this method to be in the range 22 μg/mL to greater than 1,000 μg/mL, as shown in FIG. 8. Solubilities determined by this method, in which the solutions were allowed to stand for an extended period of time with the expectation of achieving equilibrium between the NCD and the solution phase, would have been expected to correspond to equilibrium solubilities. It has been found that the solubilities determined by this method were confounded by changes in the UV spectral shape before and after incubation. Such changes typically indicate possible impurity or decomposition, overlap of the UV-visible absorption spectrum of the ligand with that of CuATSM, or other confounding mechanisms such as re-precipitation of the CuATSM with or without a ligand in the precipitate. The solubility data presented here in EXAMPLE 18 do reflect the observed increase in solubilities of the NCDs as compared to the solubility of CuATSM without a ligand, and reflect the increase in solubility at pH 1.2 as compared to lower pH's studied, both conclusions that have been further supported by EXAMPLE 13 through EXAMPLE 17, but the solubilities presented in FIG. 8 are likely not quantitatively accurate. The solubilities are better characterized by the measurement of kinetic solubilities, determined for CuATSM and a selected group of NCDs, as presented in EXAMPLE 13 through EXAMPLE 17.

Example 19

Determination of pharmacokinetics of CuATSM (dosed as CuATSM, CuATSM:gluconic acid (1:2), CuATSM:saccharin (1:2), and CuATSM:citric acid (1:1)), CuDTSM (dosed as CuDTSM:saccharin (1:2)), and CuPTSM (dosed as CuPTSM:saccharin (1:2)) in mice.

CuATSM:gluconic acid (1:2) was prepared according to the method of EXAMPLE 7. CuATSM:saccharin (1:2) was prepared according to the methods of EXAMPLE 3. CuATSM:citric acid (1:1), CuDTSM:saccharin (1:2), and CuPTSM:saccharin (1:2) were prepared according to the methods of EXAMPLE 4. Pharmacokinetics of CuATSM (dosed as CuATSM, CuATSM:gluconic acid (1:2) CuATSM:saccharin (1:2), and CuATSM:citric acid (1:1)), CuDTSM (dosed as CuDTSM:saccharin (1:2)), and CuPTSM (dosed as CuPTSM:saccharin (1:2)) were studied in mice after oral administration with dosing of the CuXTSM active pharmaceutical ingredient (API) at 30 mg/kg.

CuATSM was suspended in "Standard Suspension Vehicle" (SSV), consisting of 0.9% (w/v) NaCl, 0.5% (w/v) sodium carboxymethylcellulose, 0.5% (v/v) benzyl alcohol, and 0.4% (v/v) Tween 80 in deionized water. All other test compounds were suspended in sterile water. Samples were prepared by adding one of the compounds to the liquid vehicle (water or SSV) in a vial and then vortexing the mixture for 3 min with a stir bar inside. If the powdered sample was not completely wetted or not completely suspended, the sample was vortexed for another minute. If wetting was still incomplete, the vial was sonicated until a fully wetted suspension was obtained. Between doses, the sample was stirred on medium speed and then vortexed for an additional 20 s immediately before the next dose was removed from the vial. All dosing was completed from a single preparation of the suspension within 60 min of adding the compound to water or SSV.

Mice were deprived of pelleted food overnight, during which time 10% dextrose, as Dextroput, was provided in tap water, after which the test items were administrated orally by gavage in water or SSV. After administration, mice were subjected to blood sampling at 15 min, 30 min, 60 min, 2 h, 4 h, 8 h and 24 h while anesthetized with isoflurane. The blood samples were kept on ice after sampling and centrifuged at +4° C., 1800×g for 5 min to prepare plasma. Plasma samples were extracted and transferred into pre-labelled Eppendorf test tubes (50 μl exact in one vial, and the remaining in a second vial) and frozen at −20° C. The samples were transported on dry ice to the analysis site. Following blood sampling, mice were euthanized by cervical dislocation, and then brains were collected through opened skulls. The brains were weighed and placed in test tubes and placed on water ice. Phosphate-buffered saline (PBS, pH 7.4), 4 ml per 1 g of brain tissue, was added to the test tube and brains were homogenized by using Ultra-Turrax T25 homogenizer/S25N-10G (Setting 2, 9500 rpm, approximately 10 s). The homogenate was frozen at −20° C. immediately after homogenization. The samples were transported on dry ice to the analysis site.

Dosed mice were studied in triplicate for each of the seven time points, totaling 21 mice dosed for each studied compound. Plasma samples and brain homogenates from four untreated animals were also obtained. The plasma samples were thawed at room temperature (RT), mixed with 2-fold volume of acetonitrile, shaken and centrifuged for 10 min at 13 000×g (Heraeus Pico 17 centrifuge), after which supernatants were transferred into glass vials. The brain homogenate samples were mixed with 2-fold volume of acetonitrile:methanol, shaken, ultrasonicated for 20 min, and centrifuged for 10 min at 13 000×g (Heraeus Pico 17 centrifuge), after which supernatants were transferred into glass vials. Standard samples were spiked at 0.5, 1, 2, 5, 10, 20, 50, 100, 200, 500, 1000 and 2000 ng/ml concentrations of the active compound (API) in plasma and in blank mouse brain homogenate and were otherwise treated as the study samples. Quality control (QC) samples were prepared for concentrations 10, 100 and 1000 ng/ml in plasma or brain homogenates.

Both plasma and brain exposure 0-24 h after dosing were analyzed using LC/MS/MS, with LC-MS data obtained on a Waters Acquity UPLC+Thermo TSQ Endura triple quadrupole MS equipped with a Waters Acquity HSS T3 (2.1×50 mm, 1.8 μm) column with precolumn filter. Elution was with gradient of 0.5% formic acid/acetonitrile (99:1) increased step-wise to (5:95).

The pharmacokinetic parameters for study compounds in plasma and brain were calculated using standard non-compartmental methods. The elimination phase half-life ($t\frac{1}{2}$) was calculated by least-squares regression analysis of the terminal linear part of the log concentration-time curve. The area under the concentration-time curve (AUC) was determined by use of the linear trapezoidal rule up to the last measurable concentration to determine AUC0-24 h, and then also using extrapolation of the terminal elimination phase to infinity to determine AUC0-inf. The maximum concentration (Cmax) and the time to Cmax (Tmax) were derived directly from the concentration data. Mean Residence Time, MRT, and elimination rate constant, Ke, were also calculated from the concentration vs. time data of plasma samples. Results of the PK studies are given in
Table 2 for CuASTM and NCDs, and in
Table 3 for CuDTSM and CuPTSM NCDs.

After 30 mg/kg oral dosing of CuATSM in different forms, the highest AUC-values were observed with dosing as CuATSM:gluconic acid (1:2) (AUC0-24 h 25 163 min*ng/ml) and CuATSM:saccharin (1:2) (AUC0-24 h 20 333 min*ng/ml), while dosing as CuATSM:citric acid (1:1) or as CuATSM led to less than 50% of these AUC-values. Cmax-value after dosing with CuATSM:gluconic acid (1:2) was 36.5 ng/ml at 240 min time point, whereas Cmax values after dosing with CuATSM:citric acid (1:1), CuATSM and CuATSM:saccharin (1:2) were 14.5 ng/ml (at 60 min), 22.2 ng/ml (at 120 min), and 29.0 ng/ml (at 120 min), respectively.

TABLE 3

Pharmacokinetic (PK) parameters in mouse, based on mean plasma and brain concentrations after 30 mg/kg oral administration of CuDTSM as CuDTSM:saccharin (1:2) or of CuPTSM as CuPTSM:saccharin (1:2).

| | Active compound (30 mg/kg) | |
| --- | --- | --- |
| | CuDTSM | CuPTSM |
| | Dosed compound | |
| | CuDTSM:saccharin (1:2)/ water | CuPTSM:saccharin (1:2)/water |
| Plasma | | |
| AUC0-24h (min*ng/mL) | 7474 | 60004 |
| AUC0-inf (min*ng/mL) | 7632 | 68278 |
| Cmax (ng/mL) | 27.5 | 91.5 |
| Tmax (min) | 60 | 60 |
| $t\frac{1}{2}$ (min)(number of time points) | 372 (2) | 439 (2) |
| MRT (min) | 224 | 474 |
| $K_e$ (1/min) | 0.0019 | 0.0016 |
| Brain | | |

TABLE 2

Pharmacokinetic (PK) parameters in mouse, based on mean plasma and brain concentrations after 30 mg/kg oral administration of CuATSM as CuATSM, CuATSM:gluconic acid (1:2), CuATSM:saccharin (1:2) or CuATSM:citric acid (1:1).

| | Active compound (API) (dosed at 30 mg/kg) | | | |
| --- | --- | --- | --- | --- |
| | CuATSM | CuATSM | CuATSM | CuATSM |
| | Dosed compound/medium | | | |
| | CuATSM/SSV | CuATSM: gluconic acid (1:2)/water | CuATSM: saccharin (1:2)/ water | CuATSM:citric (1:1)/water |
| Plasma | | | | |
| AUC0-24h (min*ng/mL) | 9637 | 25163 | 20333 | 8292 |
| AUC0-inf (min*ng/mL) | 9698 | 25696 | 20436 | 8366 |
| Cmax (ng/mL) | 22.2 | 36.5 | 29.0 | 14.5 |
| Tmax (min) | 120 | 240 | 120 | 60 |
| $t\frac{1}{2}$ (min)(number of time points) | 196 (4) | 252 (3) | 170 (2) | 204 (3) |
| MRT (min) | 315 | 357 | 375 | 315 |
| $K_e$ (1/min) | 0.0035 | 0.0028 | 0.0040 | 0.0034 |
| Brain | | | | |
| AUC0-24h (min*ng/g) | 10944 | 71554 | 30643 | 15435 |
| AUC0-inf (min*ng/g) | 13843 | 73544 | 30979 | 15563 |
| Cmax (ng/g) | 28.4 | 133 | 71.8 | 77.0 |
| Tmax (min) | 60 | 240 | 15 | 60 |
| $t\frac{1}{2}$ (min) (number of time points) | 199 (3) | 261 (3) | 202 (2) | 218 (4) |
| Brain:plasma-ratio (AUC-based) | 1.1 | 2.8 | 1.5 | 1.9 |
| Brain:plasma-ratio (Cmax-based) | 1.3 | 3.6 | 2.5 | 5.3 |

TABLE 3-continued

Pharmacokinetic (PK) parameters in mouse, based on mean plasma and brain concentrations after 30 mg/kg oral administration of CuDTSM as CuDTSM:saccharin (1:2) or of CuPTSM as CuPTSM:saccharin (1:2).

| | Active compound (30 mg/kg) | |
|---|---|---|
| | CuDTSM | CuPTSM |
| | Dosed compound | |
| | CuDTSM:saccharin (1:2)/ water | CuPTSM:saccharin (1:2)/water |
| AUC0-24h (min*ng/g) | 72364 | 62832 |
| AUC0-inf (min*ng/g) | 73438 | 72025 |
| Cmax (ng/g) | 206 | 189 |
| Tmax (min) | 60 | 30 |
| t½ (min) (number of time points) | 239 (3) | 487 (2) |
| Brain:plasma-ratio (AUC-based) | 9.7 | 1.0 |
| Brain:plasma-ratio (Cmax-based) | 7.5 | 2.1 |

The highest AUC-based brain:plasma-ratio was observed for CuDTSM (after dosing as CuDTSM:saccharin (1:2)), i.e. 9.7. The Cmax brain:plasma-ratio was also high, i.e. 7.5. The lowest AUC-based brain:plasma ratio was observed for CuPTSM:saccharin (1:2), i.e. about 1.0 (Cmax-ratio 2.1). The corresponding AUC-based brain:plasma ratios for other compounds were in the range of 1.0-2.8.

Example 20

Neuroprotective and symptomatic recovery effects of orally-administered CuATSM, CuATSM:gluconic acid (1:2), and CuATSM:saccharin (1:2) in Methyl-4-phenyl-1,2,3,6-tetrahydropyridine (MPTP)-lesioned mouse models of PD. CuATSM:gluconic acid (1:2) was prepared according to the method of EXAMPLE 7. CuATSM:saccharin (1:2) was prepared according to the methods of EXAMPLE 3. CuATSM was suspended in "Standard Suspension Vehicle" (SSV), consisting of 0.9% (w/v) NaCl, 0.5% (w/v) sodium carboxymethylcellulose, 0.5% (v/v) benzyl alcohol, and 0.4% (v/v) Tween 80 in deionized water. CuATSM:gluconic acid (1:2) and CuATSM:saccharin (1:2) were suspended in sterile water. Samples were prepared by adding one of the compounds to the liquid vehicle (water or SSV) in a vial and then vortexing the mixture for 3 min with a stir bar inside.

MPTP mouse models of PD are described by (Przedborski & Vila, 2003). Mice were lesioned on Day 0 with four 10 mg/kg doses of MPTP injected intra-peritoneally (Giasson et al., 2002) at two-hour intervals which produces approximately a 50% reduction in nigral neurons. Commencing on Day 1, mice are treated with test agent at the equivalent dose of 30 mg/kg CuATSM active pharmaceutical ingredient (API), or negative SSV control, by oral gavage for 21 days. Behavioral testing via the wire test and tissue harvesting followed.

Traction wire test: Mice are moved to behavior room-testing room 1 hr before test administration. Water and food remain accessible to the mice, and a background "white noise" from a radio is used throughout the hour and test period. Each mouse is pick up the mouse by the tail in one hand, and the mouse held by the tail over the wire until it grasps the wire with the front two paws. The tail is then lowered until the mouse is suspended from the wire by its front two paws. The timing is started as soon as the mouse is suspended independently, with no assistance from the test administrator. The time taken for the mouse to grasp the wire with one of the back feet, such that two front paws and one back paw are grasping the wire, is recorded as the "pull-up time". The test is repeated for each mouse, three times in a row with a 5 minute inter-trial interval between each suspension on the wire. Mice are returned to their shared cages between trials. If a mouse falls it counts as a trial, and the time until the fall is recorded, and the inter-trial time interval is begun. If the mouse has not completed the task and has not fallen within 60 seconds, then the mouse is taken off the wire and the trial time recorded as 60 seconds.

A total of 47 mice were administered MPTP. Of these, a total of 14 mice were then treated with SSV negative control. A total of 14 mice were treated with CuATSM in SSV, of which one mouse was eliminated from the wire pull-up study because of an injured paw. A total of 9 mice were treated with CuATSM:saccharin (1:2) in water. A total of 9 mice were treated with CuATSM:gluconic acid (1:2) in water. There are typically 4-5 mice per cage that are administered with a common treatment. Trials in which the mouse fell during the trial were not included in the averages. These include one fall (one mouse) for SSV treated mice; no falls for CuATSM/SSV treated mice; one fall for one CuATSM:saccharin (1:2)/water treated mouse, and one fall each for two CuATSM:gluconic acid (1:2)/water treated mice. In all instances the mice completed the other two trials successfully so that an average time was calculated for the individual mouse and subsequently for the population. The average pull-up time for control and each the three treatment populations is given in Table 4 and FIG. 9.

CuATSM and CuATSM:saccharin (1:2) treatments result in significant (both $p<0.01$ or less) decrease in the average pull-up times as compared to SSV control. CuATSM:gluconic acid (1:2) treatment resulted in a decrease in the average pull-up time, but with a large variation in individual mouse performance resulting in a large standard error of the mean, so $p=0.07$ just misses a $p=0.05$ significance criterion between CuATSM:gluconic acid (1:2) and SSV control.

There is no significant difference (all $p \geq 30.30$) in average pull-up times between CuATSM, CuATSM:saccharin (1:2) or CuATSM:gluconic acid (1:2) treatments.

TABLE 4

Average wire pull-up times of treated, MPTP-lesioned mice.

| Treatment (Compound/medium) | Pull-up Time (seconds) | Standard Deviation (seconds) | Standard error of the mean (seconds) |
|---|---|---|---|
| SSV (n = 13) | 8.45 | 4.10 | 1.10 |
| CuATSM/SSV (n = 14) | 4.22 | 1.79 | 0.50 |
| CuATSM:saccharin (1:2)/ water (n = 9) | 3.11 | 2.68 | 0.89 |
| CuATSM:gluconic acid (1:2)/ water (n = 9) | 4.62 | 4.76 | 1.59 |

Neuroprotective effects of the CuATSM and NCDs were determined by cell count.

Following the wire pull-up time tests, the mice were anesthetized, blood samples were then obtained for plasma studies, and the mice were then sacrificed by an overdose of anesthetic. Mice were then immediately perfused with cold PBS. The right hemisphere of the brain was placed in 5 ml of chilled 4% wt/vol paraformaldehyde (Sigma-Aldrich) in 0.1 M phosphate buffer overnight at 4° C. and pH 7.4. The brains were then removed and left at 4° C. overnight in 30% wt/vol sucrose (domestic grade) in PBS before being frozen and sectioned on a cryostat. Brains were cut coronally into 30-μm sections in a 1:3 series for the substantia nigra pars compacta (SNpc).

The resulting sections were stained with Neutral Red (Niss1 stain; Sigma-Aldrich). Just prior to immunostaining, the frozen sections are fixed again for 5 min in order to ensure that the brain sections are properly fixed to the glass slide. SNpc nuclei from both normal and lesioned animals were examined. In each of the sections sampled, counts of SNpc neurons were made using optical dissector rules (Gundersen et al., 1988) and the nuclei of stained SNpc cells were the counting unit (Finkelstein et al., 2000).

The total number of neurons in the substania nigra was estimated using fractionator sampling (Finkelstein et al., 2000; Stanic et al., 2003; West & Gundersen, 1990). Counts were made at regular predetermined intervals (x, 140 μm; y, 140 μm). The entire SNpc was sampled at every third section and analyzed in a series having a random offset for each brain. Stereology was performed on a series which consisted of 7-9 SNpc sections using a random first section to start. The nigral cell counts were generated from 8 sections with a mean area sampled of $2.48 \times 108 \mu^3$. Systematic samples of the area occupied by the nuclei were made from a random starting point, photographing the SNpc in the same location in all of the images, with the images taken at the third nerve radical. The slight variation in appearance VTA could be because of slight differences of the angle of sectioning and the variation in stain intensity. An unbiased counting frame of known area (45 μm×35 μm) was superimposed on the image of the tissue sections using a stereological software package (Stereology Investigator 7; MBF Bioscience) using a DMLB microscope (Leica).

The average Neutral-Red positive staining cells observed in the substantia nigra of mice following for control mice and each of the three treatments is given in Table 5 and shown in FIG. 10. All three treatments result in significant (all p<0.01 or less) recovery of the neurons in the substania nigra as compared to SSV control. There is no significant difference (all p>0.25) between CuATSM, CuATSM:saccharin (1:2) or CuATSM:gluconic acid (1:2) treatments.

TABLE 5

Average Neutral-Red positive cells in substantia nigra of treated, MPTP-lesioned mice.

| Treatment (Compound/ medium) | Pull-up Time (seconds) | Standard Deviation (seconds) | Standard error of the mean (seconds) |
|---|---|---|---|
| SSV (n = 14) | 3949 | 488 | 130 |
| CuATSM/SSV (n = 14) | 4988 | 474 | 131 |
| CuATSM:saccharin (1:2)/water (n = 9) | 5231 | 515 | 182 |
| CuATSM:gluconic acid (1:2)/water (n = 9) | 5376 | 867 | 289 |

Copper uptake in brain and in plasma was measured by inductively-coupled plasma mass spectrometry (ICPMS) determination of the naturally-occurring copper isotope Cu-63. Brain tissue was obtained from the left hemisphere of the brain. Results for the average Cu-63 concentrations in brain tissue and in plasma of the MPTP-lesioned and treated mice are given in Table 6, and the results presented in FIG. 11 and FIG. 12. All treatments result in significant (all p<0.001) increase in Cu-63 concentrations in brain tissue as compared to the SSV control. There is no significant difference (all p>0.25) between CuATSM, CuATSM:saccharin (1:2) or CuATSM:gluconic acid (1:2) treatments in Cu-63 brain uptake. No treatments resulted in significant (all p>0.05) change in Cu-63 concentrations in plasma as compared to the SSV control. There is a small (p=0.045) difference between the treatments with CuATSM:saccharin (1:2) as compared to CuATSM:gluconic acid (1:2); CuATSM:saccharin (1:2), has the higher plasma Cu-63 concentration.

TABLE 6

Brain and plasma concentrations of Cu-63 in treated, MPTP-lesioned mice.

| Treatment (Compound/medium) | Cu-63 in brain | | | Cu-63 in plasma | | |
|---|---|---|---|---|---|---|
| | Average (μg/g) | Standard Deviation (μg/g) | Standard Error of the Mean (μg/g) | Average (μmol/ltr) | Standard Deviation (μmol/liter) | Standard Error of the Mean (μmol/liter) |
| SSV (n = 14) | 4.72 | 0.65 | 0.17 | 5.82 | 0.72 | 0.19 |
| CuATSM/SSV (n = 14) | 18.48 | 11.01 | 2.94 | 5.40 | 0.98 | 0.26 |
| CuATSM:saccharin (1:2)/water (n = 9) | 14.66 | 2.56 | 0.85 | 6.13 | 0.99 | 0.33 |
| CuATSM:gluconic acid (1:2)/water (n = 9) | 22.20 | 12.55 | 4.18 | 5.27 | 0.59 | 0.20 |

Example 21

Treatment with NCD of Cu-ATSM and Improvement of Stool Frequency:

The experiments demonstrate that the treatment of MPTP lesioned mice as rodent models of Parkinson's Disease result in restoration of motor performance and cognitive function to MPTP lesioned mice.

Accordingly, certain metal complexes, including the NCD of metal complexes of the application are effective in delivering bio-available metal and may be used in the treatment of conditions which can be prevented, treated or ameliorated by metal delivery. In particular these metal complexes are found to be effective in delivering metal to the cells in a form which lead to a significant anti-oxidant effect being observed in the cell. In one aspect, certain metal complexes demonstrated an ability to mediate OS.

In addition to motor dysfunction experienced by patients with certain neurological diseases, such as Parkinson's Disease, non-motor symptoms including gastrointestinal ailments, such as constipation, are commonly experienced by patients with neurological diseases. These symptoms have a significant and adverse impact on the quality of the patients' life. In one aspect of the present application, there is provided a method for treating or reducing gastrointestinal diseases or ailments associated with patients with neurological diseases, the method includes the administration of a therapeutically effective amount of the metal complex as disclosed herein.

Several rodent models of Parkinson's Disease have shown gastrointestinal dysfunction, which has been correlated with the loss of neuronal subpopulations within the enteric nervous system. Intraperitoneal administration of MPTP (1-methyl-4-phenyl-1,2,3,6-tetrahydropyridine) caused a significant reduction in the number of dopaminergic neurons within the substantia nigra pars compacta of C57BL/6 mice. A reduction in neuronal subpopulations within the myenteric plexus of the ileum 21 days after lesioning was also detected and was concomitant with a reduction in stool frequency, indicative of digestive dysfunction.

Oral administration of NCD of CuATSM have been shown to be neuroprotective and restore motor performance and cognitive function to MPTP lesioned mice. In addition, the treatment of the metal complexes, such as CuATSM, also improved stool frequency and is found to be correlated with the restoration of neuronal subpopulations in the myenteric plexus of MPTP lesioned mice. Patients with neurological diseases, such as Parkinson's Diseases experiencing gastrointestinal disfunction such as constipation, may be associated with the loss of neuronal populations in conjunction with enteric glial cell reactivity within the myenteric plexus of the gastrointestinal tract. Treatment of these patients with metal complexes, such as CuATSM, that are neuroprotective in the central nervous system provides symptom release and also results in disease modifying in the gastrointestinal tract.

MPTP lesioned mice may be treated with the NCD of CuATSM, and the results are compared with untreated mice. The NCD treated mice show improved stool frequency and the results are correlated with the restoration of neuronal subpopulations in the myenteric plexus of MPTP lesioned mice. These observations suggest that the constipation experienced by Parkinson's Disease patients may be a consequence of the loss of neuronal cell populations in conjunction with enteric glial cell reactivity within the myenteric plexus of the gastrointestinal tract and that treatments using agents such as the NCDs of CuATSM are neuroprotective in the central nervous system, and may also provide symptom release and be disease modifying in the gastrointestinal tract. FIG. 13 shows representative results for a comparison of stool frequency between vehicle and treatment with Cu-ATSM.

Example 22

Reduction in Extracellular Amyloid Beta Levels:
Using Cu-ATSM:
Treatment of APP-CHO cells with the NCD Cu-ATSM results in an increase in the intracellular copper levels as expected of the cell permeable Cu-ATSM. Five treatment regimes are used namely a control, 1 μM, 5 μM, 10 μM, 25 μM and 50 μM. APP-transfected CHO cells are treated with each of the doses of the NCD complex complex for 6 hr in serum-free medium and conditioned medium is then collected and assayed for Aβ1-40 peptide by routine Aβ ELISA. The NCD complex significantly inhibits Aβ1-40 levels in the medium at all concentrations tested when compared to uncomplexed ATSMH$_2$.

Example 23

Reduction of Cellular Abeta:
Generation of APP-Transfected Chinese Hamster Ovary (CHO):
APP-CHO cells are generated by expressing the 695 amino acid APP cDNA in the pIRESpuro2 expression vector (Clontech, Mountain View, Calif., USA). Cells are transfected using Lipofectamine 2000 and cultured in RPMI-1640 media supplemented with 1 mM glutamine and 10% fetal bovine serum (from Invitrogen, Mount Waverley, Australia). Transfected cells are selected and maintained using 7.5 μg/ml puromycin (Sigma-Aldrich). Treatment of Cells with NCD of metal complexes:
APP-CHO cells are passaged at a ratio of 1:5 and grown in 6 well plates for 3 days before experiments. The NCDs of metal complexes are prepared as a 10 mM stock solution in DMSO and added to serum-free RPMI medium supplemented with puromycin. Medium is briefly mixed by aspiration prior to addition to cells. Control cultures are treated with vehicle (DMSO) alone. Cultures are incubated for 6 hr and conditioned media taken for measurement of Aβ1-40 levels by ELISA.
Double Antibody Capture Enzyme-Linked Immunosorbent Assay (ELISA) for Aβ Detection:
Aβ levels are determined in culture medium using the 384 well Aβ-40 ELISA protocol. 384 Well plates are coated with monoclonal antibody (mAb) G2-10 in carbonate-bicarbonate coating buffer (pH 9.6) for Aβ$_{1-40}$ detection. The plates are left to incubate overnight at 4° C. with rocking. The plates are then washed three times with PBST at RT with rocking and the solution discarded after each wash. Then 100 μL of 0.5% (w/v) hydrolysed casein in PBS (pH 7.4) is added to each well and left to incubate for 2 hr at 37° C. to prevent non-specific binding. The plates are then washed three times with PBST at RT with rocking. 20 ng of biotinylated mAb WO2 (epitope at Aβ$_{5-8}$) is added to each well of the plates (10 μL/well at 2 ng/μL). 50 μL/well of Aβ$_{1-40}$ standard peptide samples (MHRI, Melbourne, Australia), cell culture medium samples and the blanks are added. The plates are left to incubate overnight at 4° C. with rocking.

The plates are washed nine times with PBST at RT with rocking. 25 μL streptavidin-labelled europium is added at a dilution of 1:1000. Plates are then washed ten times with PBST where the 9$^{th}$ and 10$^{th}$ wash was left on for 5 min before discarding. To develop the plates 80 μL of enhancement solution is added to each well and plates are read in a WALLAC Victor$^2$ plate reader with excitation (Ex) at 340 nm and emission (Em) at 613 nm. Aβ$_{1-40}$ peptide standards and samples are assayed in triplicate. The values obtained from the triplicate wells are used to calculate the Aβ concentration (expressed as ng/mL) based on the standard curve generated on each plate.

Example 24

Ionophore Assay:

M17 human neuroblastoma cells are plated out on 6 well plates and left overnight. Enough cells are added to give approximately 70% confluent the following day of the experiment. The test cells are incubated in 1 ml of media and compound mix for 5 hours at 37° C. At the end of the incubation the media is removed with a vacuum aspirator and 1 ml of PBS added to dislodge the cells. Cells are then put into Eppendorf tubes and pelleted. The PBS is removed and the remaining cell pellets are frozen at −20° C.

Cell pellets of similar levels are placed in 1.5 ml microfuge tubes. To each tube is added 50 µl of concentrated Nitric Acid (Aristar, BDH) to each cell pellet and allowed each cell pellet is allowed to digest over night. The samples are heated for 20 min at 90° C. to complete the digestion. The volume of each sample is reduced to ~45 µl after digestion. To each is added 1 ml of the 1% Nitric Acid diluent. Measurements are made using a Varian UltraMass ICPMS instrument under operating conditions suitable for routine multi-element analysis.

The instrument is calibrated using Blank, 10, 50 and 100 ppb of a certified multi-element ICPMS standard solution (ICP-MS-CA12-1, Accustandard) for Cu and Zn in 1% nitric acid. Use an certified internal standard solution containing 100 ppb Yttrium (Y 89) as an internal control (ICP-MS-IS-MIX1-1, Accustandard).

The data are reported versus level of a known internal control (Clioquinol). The data demonstrates that the complexes of the invention are effective in delivering the metal to the cell.

Example 25

Cytotoxicity Testing—M17 Neuroblastoma Cells:

Day 1. The test cells are cultured at 37° C./5% $CO_2$ till almost confluent in 75 $cm^2$ flask. The media is removed and the cells incubated with 5 ml PBS for about 5 mins to dislodge cells from the plastic surface. A pipette is used to re-suspend cells and 5 mls of growth media added. The cell suspension is removed and added to 15 ml Falcon tube. The suspension was mixed well by inversion and about 100 µl transferred into an Eppendorf.

A typical assay assessing 15 compounds uses five 48 well plates. The inner 24 wells are the only ones used to reduce the amount of evaporation over 48 hrs. 200 µl of media is added to each of the inner 24 wells. Cell suspensions are mixed by inversion and the desired number of cells added to each well. Cell addition is continued across each plate and the cell suspension mixed in the falcon tube by inversion between each plate. The plates are given a minor shake and returned to a 37° C. incubator. Plates are left overnight for cells to settle in the wells.

Day 2. Compounds to be tested are selected for the assay. Calculate from the mol wt. and mg of NCD complex in the Eppendorf, the number of ml of DMSO to add to make a stock solution of 10 mM. In the case of CQ (Clioquinol) a 1 mM stock solution is required due to precipitation of a more concentrated solution when diluted in media.

DMSO is added to the Eppendorfs (typically 200-500 µl), vortexed until dissolved and incubated with the compounds at 37° C. for 60 mins to aid solubilisation. The NCD complexes are removed and again vortexed and checked for any undissolved complexes. The 10 mM stock solutions should then be diluted 1:10 to make a final concentration of 1 mM. 180 µl of DMSO is added to the test tube and 20 µl of each of the compound solutions is added to each of the test tubes to create the test solutions which are then vortexed again to ensure complete homogenation of the test mixture. Each compound is then diluted to final concentrations of 10 µM and 1 µM.

The desired amount of the test solution and the control sample is added to the plates which are then returned to the incubator for a 48 hour period at 37° C. At the completion of the 48 hour period the plates are removed from the incubator and an aspirator used to remove the media from the first plate. Then 220 µl of MTT (a tetrazolium salt used for mitochondrial assays)/media solution is added to each well. Plates are then returned to 37° C. and incubated for 1 hour. After 1 hour the plates are removed from the incubator and the media/MTT solution removed using the aspirator vacuum pump.

200 µl DMSO is added to each well and the plate gently agitates so that the DMSO dissolves the MTT crystals and the remaining cell debris. After about 10 mins the now purple DMSO in the wells should be clear. MTT is a tetrazolium salt which is converted from yellow to purple by active mitochondria. The more cells present and therefore more mitochondria results in a more intense purple color. The plates can now be read on a plate reader at 570 nm.

Example 26

Effect of the NCD of metal complexes such as the NCD complex of Cu-ATSM as antioxidants in a Parkinsons's disease model. A series of trials is conducted in which the effect of the NCD of Cu-ATSM on inhibiting Dopamine induced cell death are conducted on WT cells and A30P cells. The protocol that may be used is as noted below.

Cell Culture:

The cell line is maintained in OPTI-MEM (Gibco) supplemented with 10% fetal calf serum (FCS), Non-essential amino acids, sodium pyruvate and Penn/Strep. Cells are incubated at 37° C. in a humidified atmosphere of 95% air and 5% $CO_2$. Cell assays are plated out into 48 well culture plates at $4 \times 10^4$ cells per well. Cells are left to settle overnight then incubated with drugs for 24 h prior to being subjected to MTT assays for cell viability.

The procedure for the preparation of the metal complexes of the present application, along with their methods of treatment are disclosed in International Patent Application PCT/AU2007/001792, published as WO 2008/061306, the disclosure of which is incorporated herein in its entirety.

While a number of exemplary embodiments, aspects and variations have been provided herein, those of skill in the art will recognize certain modifications, permutations, additions and combinations and certain sub-combinations of the embodiments, aspects and variations. It is intended that the following claims are interpreted to include all such modifications, permutations, additions and combinations and certain sub-combinations of the embodiments, aspects and variations are within their scope. The entire disclosures of all documents cited throughout this application are incorporated herein by reference.

What is claimed is:

1. A non-covalent derivative (NCD) of a compound of Formula I comprising

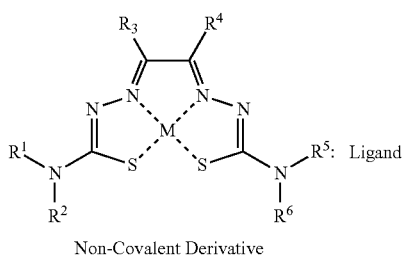

Non-Covalent Derivative wherein:

M is Zn or Cu;

$R^1$ and $R^2$ are each independently selected from the group consisting of H, methyl, or ethyl $R^3$ and $R^4$ are each independently H, methyl, or ethyl;

$R^5$ and $R^6$ are each independently selected from the group consisting of H, methyl, or ethyl Ligand is selected from the group consisting of citric acid, saccharine, gluconic acid, L-tyrosine methyl ester, alanine ethyl ester, L-cystine dimethyl ester, thiodipropionic acid, malic acid, and N,N,N',N'-tetraethylterephthalamide; and a pharmaceutically acceptable salt thereof.

2. The NCD of claim 1 wherein the compound of Formula I is selected from the group consisting of CuATSM, CuGTSM, CuPTSM, CuDTSM, ZnATSE, and ZnATSM.

3. The NCD of claim 1 which is CuATSM:gluconic acid.

4. A pharmaceutical composition comprising a therapeutically effective amount of an NCD of claim 1, and a pharmaceutically acceptable excipient or salt.

* * * * *